(12) United States Patent
Cleemann et al.

(10) Patent No.: US 8,906,847 B2
(45) Date of Patent: Dec. 9, 2014

(54) PRODRUG COMPRISING A DRUG LINKER CONJUGATE

(75) Inventors: Felix Cleemann, Heidelberg (DE); Ulrich Hersel, Heidelberg (DE); Silvia Kaden, Heidelberg (DE); Harald Rau, Heidelberg (DE); Thomas Wegge, Heidelberg (DE)

(73) Assignee: Ascendis Pharma A/S, Hellerup (DK)

( * ) Notice: Subject to any disclaimer, the term of this patent is extended or adjusted under 35 U.S.C. 154(b) by 820 days.

(21) Appl. No.: 12/865,693

(22) PCT Filed: Jan. 30, 2009

(86) PCT No.: PCT/EP2009/051079
§ 371 (c)(1),
(2), (4) Date: Oct. 8, 2010

(87) PCT Pub. No.: WO2009/095479
PCT Pub. Date: Aug. 6, 2009

(65) Prior Publication Data
US 2011/0053848 A1    Mar. 3, 2011

(30) Foreign Application Priority Data

Feb. 1, 2008  (EP) .................................... 08150973
Dec. 5, 2008  (EP) .................................... 08170872

(51) Int. Cl.
| | | |
|---|---|---|
| A61K 47/00 | (2006.01) | |
| A61K 47/06 | (2006.01) | |
| C40B 80/00 | (2006.01) | |
| A61K 39/395 | (2006.01) | |
| C07K 16/00 | (2006.01) | |
| A61K 47/48 | (2006.01) | |

(52) U.S. Cl.
CPC ..... *A61K 47/48338* (2013.01); *A61K 47/48215* (2013.01)
USPC ......... 514/1.3; 506/42; 424/130.1; 530/391.9

(58) Field of Classification Search
None
See application file for complete search history.

(56) References Cited

U.S. PATENT DOCUMENTS

2006/0115865 A1* 6/2006 Ouyang et al. ............... 435/7.92

FOREIGN PATENT DOCUMENTS

| JP | 1764360 | * | 7/2005 |
|---|---|---|---|
| WO | WO 00/69900 | | 11/2000 |
| WO | WO 2004/108070 | | 12/2004 |
| WO | WO 2006/003014 | | 1/2006 |
| WO | WO-2006/003014 | * | 1/2006 |
| WO | WO 2006/047451 | | 5/2006 |
| WO | WO-2006/073396 | * | 7/2006 |
| WO | WO 2006/115865 | | 11/2006 |
| WO | WO 2006/136586 | | 12/2006 |

OTHER PUBLICATIONS

Testa, Biochemical Pharmacology 68 (2004) 2097-2106.*
Bernkop-Schnu-rch, 1997, Journal of Controlled Release 47 (1997) 113-121.*
Gutniak, M. et al. Antidiabetogenic effect of glucagon-like peptide-1 (7-36)amide in normal subjects and patients with diabetes mellitus. N Engl J Med 1992;326:1316-22.
Sohma, Y. et al. Development of water-soluable prodrugs of the HIV-1 protease inhibitor KNI-727: Importance of the conversion time for higher gastrointestinal absorption of prodrugs based on spontaneous chemical cleavage. J Med Chem 2003;46:4124-4135.
Goke, R. et al. Exendin-4 is a high potency agonist and truncated exendin-(9-39)-amide an antagonist at the glucagon-like peptide 1-(7-36)-amide receptor of insulin-secreting β-Cells. J Bio Chem 1993; 26:19650-19655.
Na, D.H., et al. Monitoring of peptide acylation inside degrading PLGA microspheres by capillary electrophoresis and MALDI-TOF mass spectrometry. J Contr Rel 2003;92:291-299.
Shafer, J.A. et al. Participation of a neighboring amide group in the decomposition of esters and amides of substituted phthalamic acids. J Org Chem 1963;28:1899-1901.
Eng, J. et al. Isolation and characterization of exendin-4, and exendin-3 analogue, from *Heloderma suspectum* venom. J Biol Chem 1992;267:7402-7405.
Hayashi, Y. et al. Development of oligoarginine-drug conjugates linked to new peptidic self-cleavable spacers toward effective intestinal absorption. Bioorganic and Medicinal Chemistry Letters 2007;17:5129-5132.

(Continued)

*Primary Examiner* — Satyanarayana R Gudibande
(74) *Attorney, Agent, or Firm* — Frommer Lawrence & Haug LLP

(57) ABSTRACT

The present invention relates to a prodrug or a pharmaceutically acceptable salt thereof comprising a drug linker conjugate D-L, wherein -D is an amine containing biologically active moiety; and -L is a non-biologically active linker moiety -L$^1$ represented by formula (I), wherein the dashed line indicates the attachment to the amine of the biologically active moiety and wherein R$^1$, R$^{1a}$, R$^2$, R$^{2a}$, R$^3$, R$^{3a}$, X, X$^1$, X$^2$, X$^3$ have the meaning as indicated in the description and the claims and wherein L$^1$ is substituted with one to four groups L$^2$-Z and optionally further substituted, provided that the hydrogen marked with the asterisk in formula (I) is not replaced by a substituent; wherein L$^2$ is a single chemical bond or a spacer; and Z is a carrier group. The invention also relates to A-L, wherein A is a leaving group, pharmaceutical composition comprising said prodrugs and their use as medicaments.

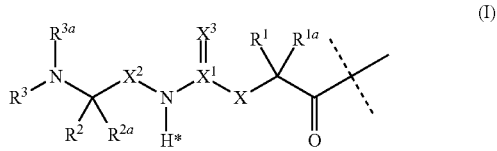

(I)

37 Claims, 9 Drawing Sheets

(56) References Cited

OTHER PUBLICATIONS

Gomes, P. et al. Cyclization-activated prodrugs. Molecules 2007;12:2484-2506.
Garman, A. et al. The preparation and properties of novel reversible polymer-protein conjugates. FEBS Lett 1987;223:361-365.
Young, A. et al. Glucose-lowering and insulin-sensitizing actions of exendin-4. Diabetes 1999;48:1026-1034.
Bundgaard, H. et al. Hydrolysis and rearrangement of phthalamic acid derivatives and assessment of their potential as prodrug forms for amines. Acta Pharmaceutica Nordica 1990;2:333-342.
Edwards, C.M.B. et al. Exendin-4 reduces fasting and postprandial glucose and decreases energy intake in healthy volunteers. Am J Physiol Endocrinol Metab 2001;281:155-161.
Shan, D. et al., "Prodrug Strategies Based on Intramolecular Cyclizaion Reactions", Journal of Pharmaceutical Sciences, vol. 86, No. 7, Jul. 1997, pp. 765-777, American Chemical Society & American Pharmaceutical Association.
Harkevich, D.A., "Farmakologiya", M., Medizina, 1987, str.47-48 (= Pharmacology, Moscow, Medicine, 1987, p. 47-48).
Belikov, V.G., "Farmazevticheskaya Khimiya", M., Vysshaya shoka, 1993, t. 1, str. 43-47 (= Pharmaceutical Chemistry, Moscow, High School, 1993, vol. 1, p. 43-47).
Kudiun, A.N., "Problemy vzaimodeistviya lekarstvennykh veshestv", Earmaziya, 1983, No. 2, str. 71 (= Problems of Interaction of medicinal substances, Pharmacy, 1983, No. 2, p. 71).
Harkevich, D.A., "Farmakologiya", M., Medizina, 1987, str.50-52 (= Pharmacology, Moscow, Medicine, 1987, p. 50-52).

* cited by examiner

| Compound | Structure | Starting materials | Synthesis method | MW (calc.) (g/mol) | m/z (ESI-MS) [M+3H]³⁺ |
|---|---|---|---|---|---|
| 38a | (phthalamide-Exendin with dimethylaminopropyl) | phthalic anhydride + dimethylaminopropylamine | A | 4404 | 1469.4 |
| 38b | (cyclohexane dicarboxamide-Exendin +E with dimethylaminopropyl) | cyclohexane-1,2-dicarboxylic anhydride + dimethylaminopropylamine | A | 4410 | 1471.5 |
| 38c | (cyclohexane dicarboxamide-Exendin +E with dimethylaminopropyl) | cyclohexane-1,2-dicarboxylic anhydride +E + dimethylaminopropylamine | A | 4410 | 1471.5 |
| 38d | (succinamide-Exendin with diaminobutyl) | succinic anhydride + diaminobutane | A | 4328 | 1443.8 |

Fig. 2A

PRODRUG COMPRISING A DRUG LINKER CONJUGATE

The present invention relates to a prodrug or a pharmaceutically acceptable salt thereof comprising a drug linker conjugate D-L. The invention also relates to pharmaceutical compositions comprising said prodrugs and their use as medicaments.

To enhance physicochemical or pharmacokinetic properties of a drug in vivo such drug can be conjugated with a carrier.

Typically, carriers in drug delivery are either used in a non-covalent fashion, with the drug physicochemically formulated into a solvent-carrier mixture, or by covalent attachment of a carrier reagent to one of the drug's functional groups.

However the non-covalent approach requires a highly efficient drug encapsulation to prevent uncontrolled, burst-type release of the drug. Restraining the diffusion of an unbound, water soluble drug molecule requires strong van der Waals contacts, frequently mediated through hydrophobic moieties. Many conformationally sensitive drugs, such as proteins or peptides, are rendered dysfunctional during the encapsulation process and/or during subsequent storage of the encapsulated drug. In addition, such amino-containing drugs readily undergo side reactions with carrier degradation products (see, for example, D. H. Lee et al., J. Contr. Rel., 2003, 92, 291-299). Furthermore, dependence of the release mechanism of the drug upon biodegradation may cause interpatient variability.

Alternatively, the drugs may be conjugated to a carrier through covalent bonds. This approach is applied to various classes of molecules, from so-called small molecules, through natural products up to larger proteins. Covalent drug carrier conjugates can be divided into two groups. Firstly, conjugates, where the covalent bond between carrier and drug is mostly present during the action of the drug ("permanent covalent bond"), i.e. a derivative of the drug exhibits its pharmacological effects as it is known for the drug as such. Secondly, the covalent bond is mostly previously cleaved to release the drug as such, which can exhibit its known pharmacological effects. In the latter case the covalent drug carrier conjugate is called carrier linked prodrug or carrier prodrug.

In order to ensure cleavage of the covalent bond between carrier and drug easy removal of said bond in vivo is required to release the drug (prodrug activation).

Prodrug activation may occur by enzymatic or non-enzymatic cleavage of the bond between the carrier and the drug molecule, or a sequential combination of both, i.e. an enzymatic step followed by a non-enzymatic rearrangement.

Enzymatically induced prodrug activation is characterized in that the cleavage in enzyme-free in-vitro environment such as an aqueous buffer solution, of, e.g., an ester or amide may occur, but the corresponding rate of hydrolysis may be much too slow and not therapeutically useful. In an in-vivo environment, esterases or amidases are typically present and the esterases and amidases may cause significant catalytic acceleration of the kinetics of hydrolysis from twofold up to several orders of magnitude. Therefore, the cleavage is predominantly controlled by the enzymatic reaction.

A major drawback of predominantly enzymatic cleavage is interpatient variability. Enzyme levels may differ significantly between individuals resulting in biological variation of prodrug activation by the enzymatic cleavage. The enzyme levels may also vary depending on the site of administration. For instance it is known that in the case of subcutaneous injection, certain areas of the body yield more predictable therapeutic effects than others. To reduce this unpredictable effect, non-enzymatic cleavage or intramolecular catalysis is of particular interest.

Therefore, enzyme-independent autocatalytic cleavage of carrier and biologically active moiety is preferred. In most cases this is achieved by an appropriately designed linker moiety between the carrier and the biologically active moiety, which is directly attached to the functional group of a biologically active moiety via covalent bond.

Specific linker types are known in the art.

Y. Sohma et al., J. Med. Chem. 46 (2003), 4124-4135 describe ester based prodrugs, where the carrier is water-soluble and the biologically active moiety is derived from HIV-1 protease inhibitor KNI-727. The linker used is attached to the biologically active moiety via ester group. The mechanism of this prodrug system is cyclization-activation by cyclic imide formation for the cleavage of ester bonds.

However this is disadvantageous because of the instability of the ester functional group. Furthermore, ester groups may be less chemoselectively addressable for the conjugation of the carrier or linker and the drug.

A. J. Garman et al. (A. J. Garman, S. B. Kalindjan, FEBS Lett. 1987, 223 (2), 361-365 1987) use PEG5000-maleic anhydride for the reversible modification of amino groups in tissue-type plasminogen activator and urokinase. Regeneration of functional enzyme from PEG-uPA conjugate upon incubation at pH 7.4 buffer by cleavage of the maleamic acid linkage follows first order kinetics with a half-life of 6.1 h. A disadvantage of the maleamic acid linkage is the lack of stability of the conjugate at lower pH values. This limits the applicability of the maleamic acid linkage to biologically active agents which are stable at basic (high) pH values, as purification of the biologically active agent polymer conjugate has to be performed under basic (high pH) conditions to prevent premature prodrug cleavage.

In WO-A 2004/108070 prodrug system based on N,N-bis-(2-hydroxyethyl)glycine amide (bicine) linker is described. In this system two PEG carrier molecules are linked to a bicine molecule coupled to an amino group of the drug molecule. The first two steps in prodrug activation is the enzymatic cleavage of the first linkages connecting both PEG carrier molecules with the hydroxy groups of the bicine activating group. Different linkages between PEG and bicine are described resulting in different prodrug activation kinetics. The second step in prodrug activation is the cleavage of the second linkage connecting the bicine activating group to the amino group of the drug molecule. The main disadvantage of this system is the connection of the polymer to the bicine linker resulting in a slow hydrolysis rate of this second bicine amide linkage (t1/2>3 h in phosphate buffer). Consequently the release of a bicine-modified prodrug intermediate may show different pharmacokinetic, immunogenic, toxicological and pharmacodynamic properties as compared to the parent native drug molecule.

Another bicine-based system is described in WO-A 2006/136586.

Accordingly, there is a need for alternative carrier-linked prodrugs, where the linker allows an autocatalytic cleavage to release a drug in an unmodified form without remaining residues originating from the linker.

BRIEF DESCRIPTION OF THE DRAWINGS

FIGS. 2A-2G, collectively referred to as FIG. 2, depict further details concerning compound numerals, starting materials, synthesis method, molecular weight (MW), and MS data.

DETAILED DESCRIPTION OF EMBODIMENTS

Figure 1:
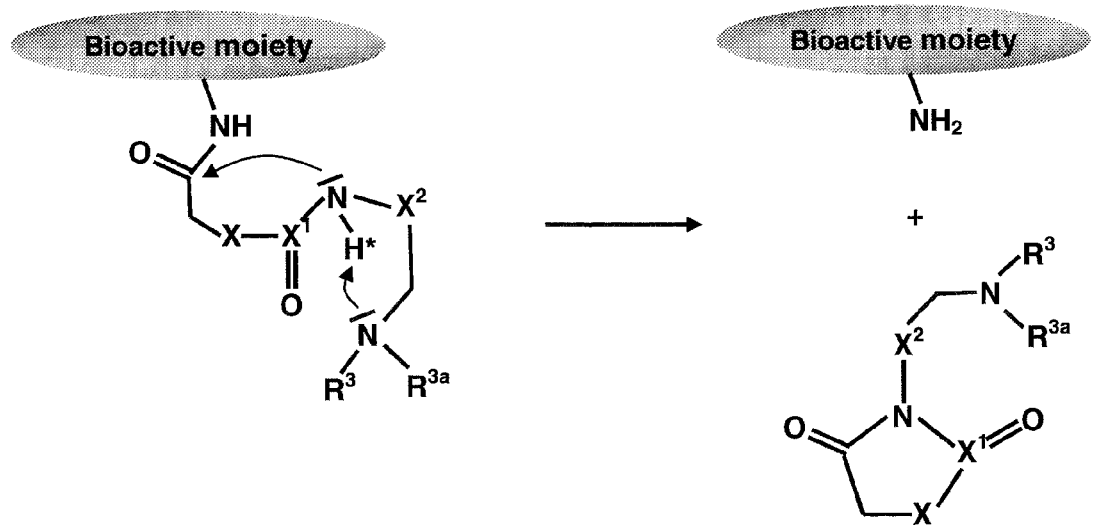
FIG. 1 shows an example of the cleavage resulting in a cyclic imide.
Figure 2B:
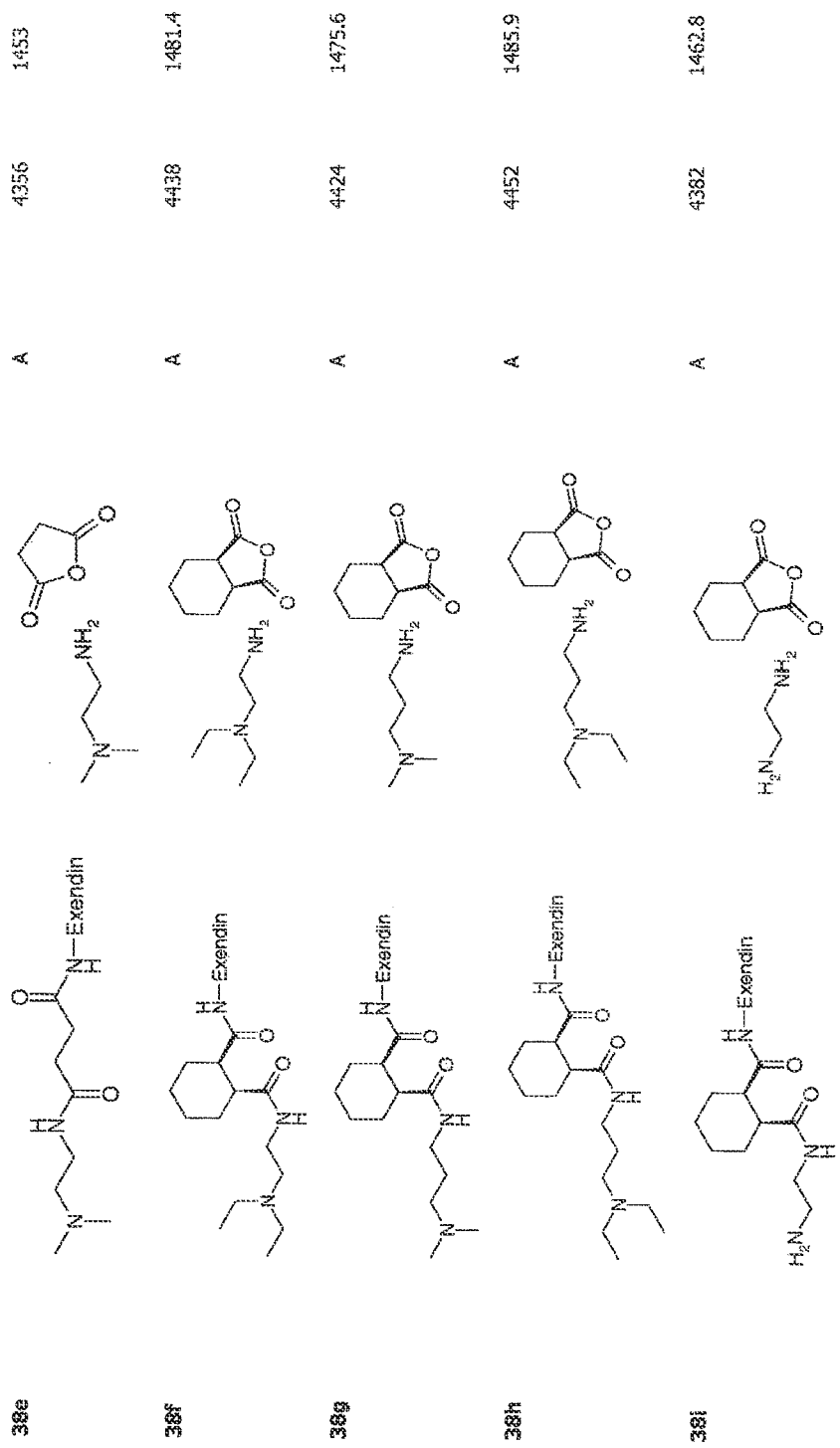
Figure 2C:
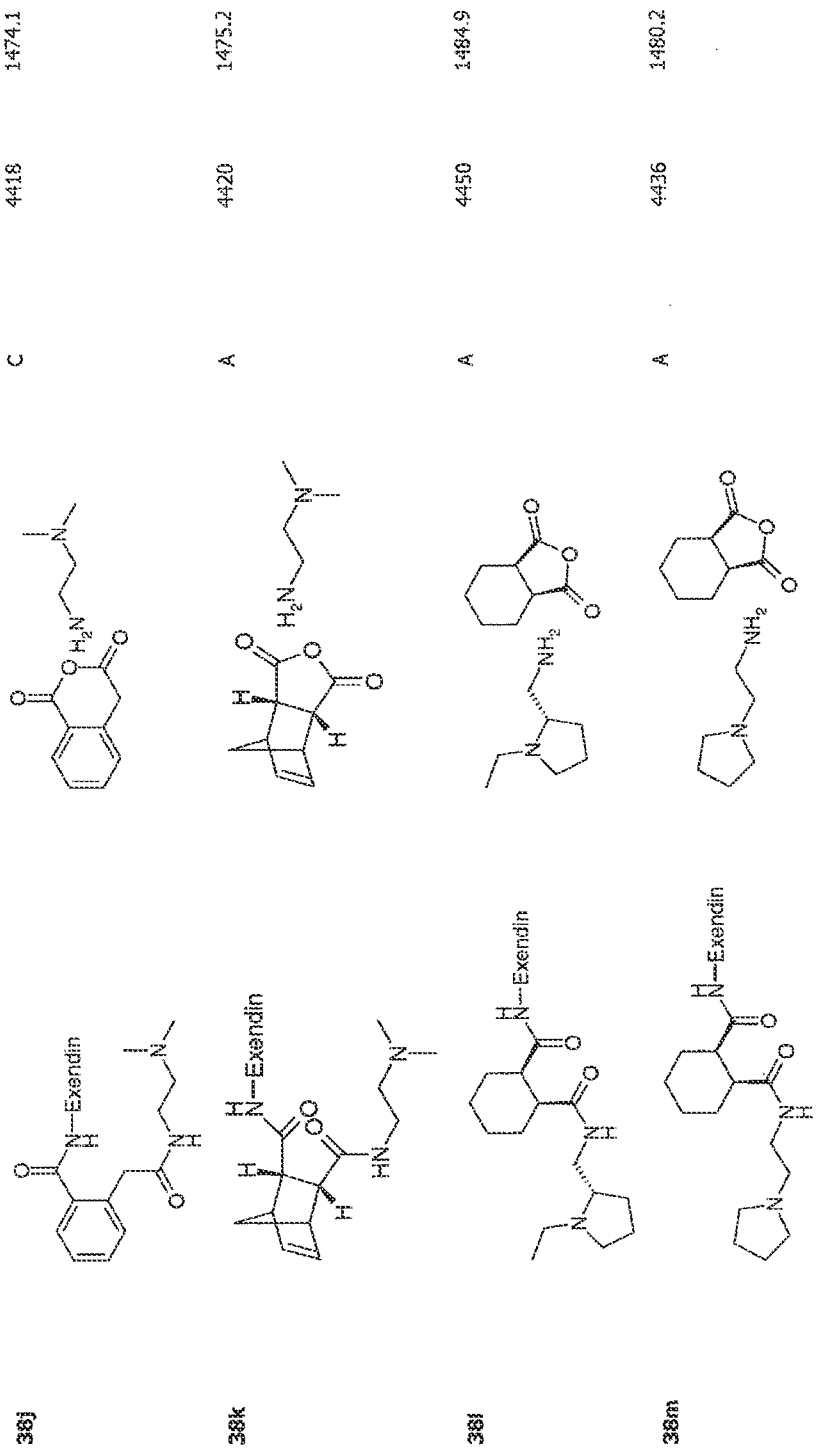
Figure 2D:
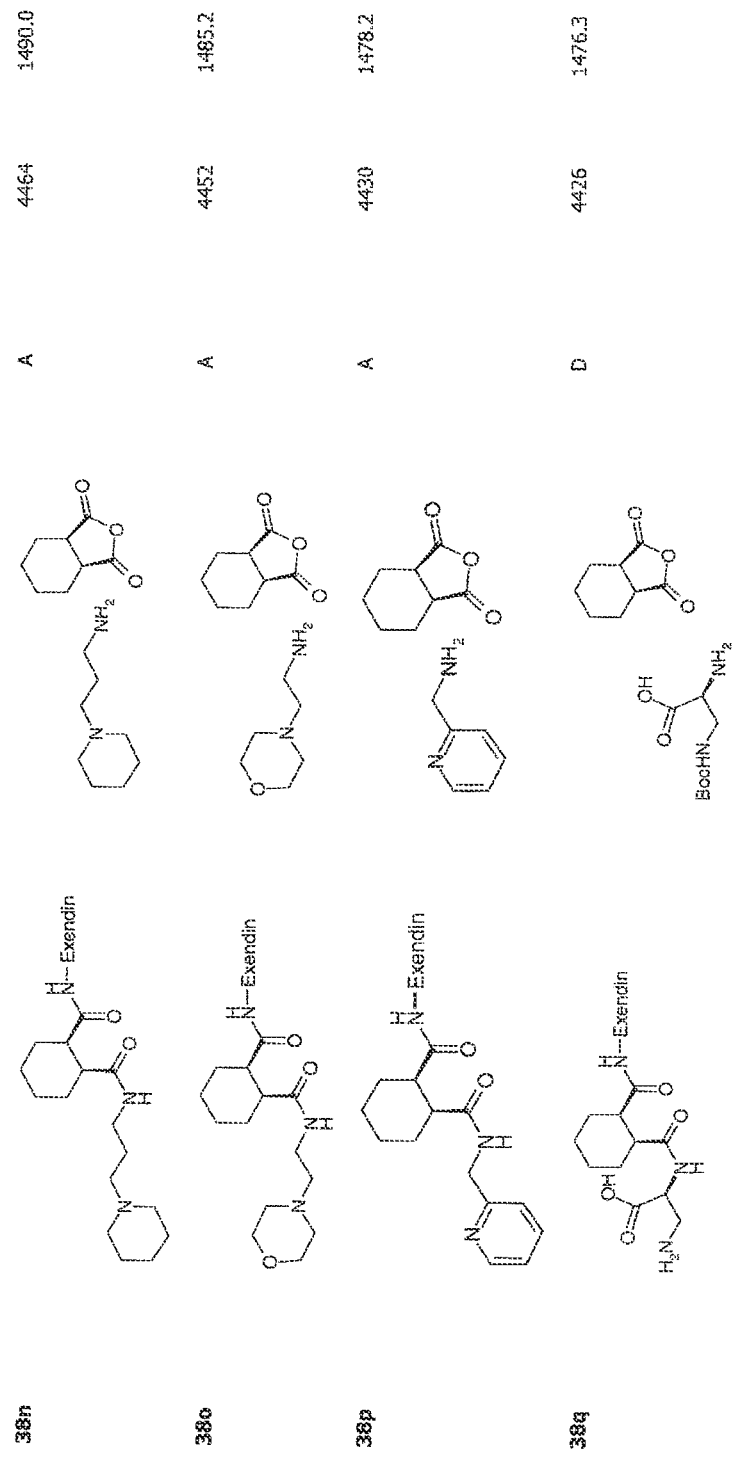
Figure 2E:
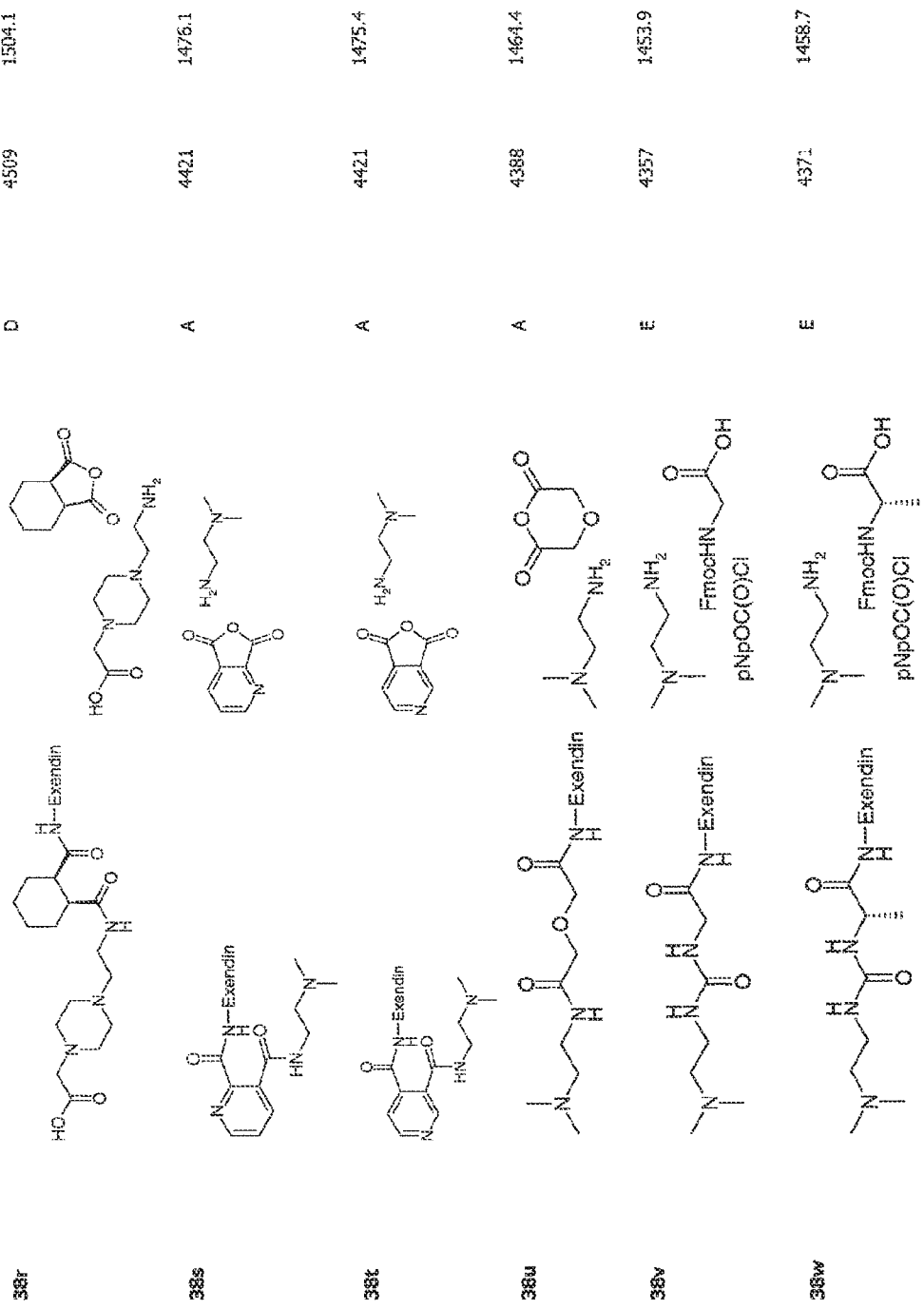
Figure 2F:
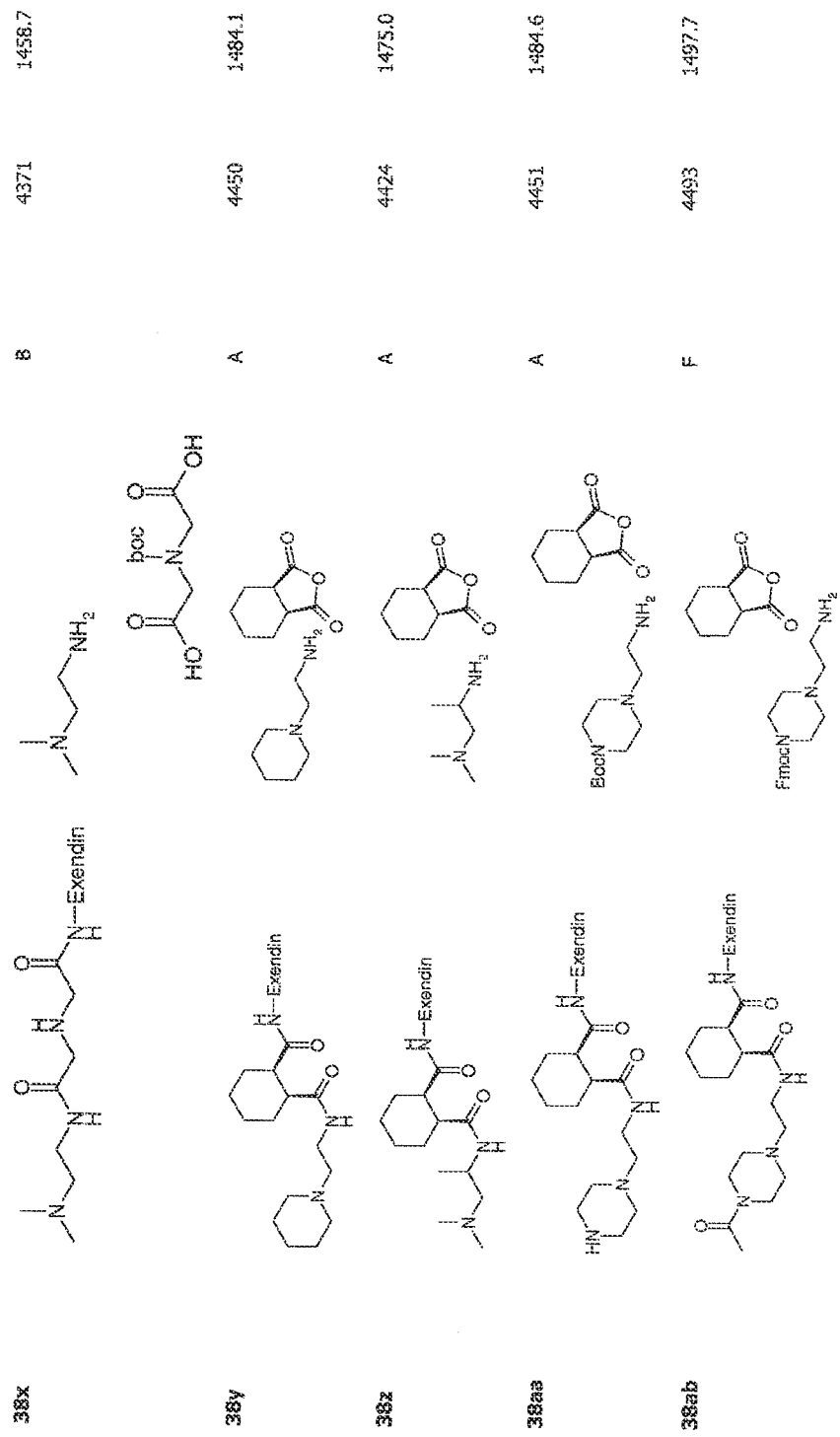
Figure 2G:
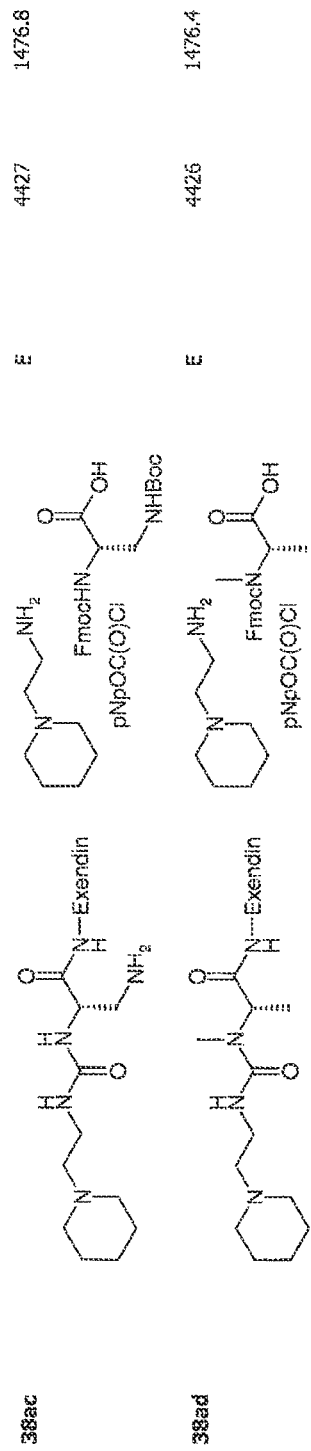

Thus, an object of the present invention is to provide such drug linker conjugates, where the linker is covalently attached via a cleavable bond to a biologically active moiety (representing the drug after release), and where the linker is further covalently attached via a permanent bond to a carrier directly or via a spacer to form the carrier-linked prodrug.

This object is achieved by a prodrug or a pharmaceutically acceptable salt thereof comprising a drug linker conjugate D-L, wherein -D is a nitrogen containing biologically active moiety; and
-L is a non-biologically active linker moiety -$L^1$ represented by formula (I),

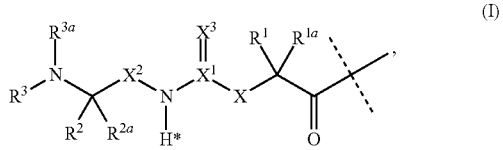

wherein the dashed line indicates the attachment to the nitrogen of the biologically active moiety by forming an amide bond;

X is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;

$X^1$ is C; or S(O);

$X^2$ is $C(R^7, R^{7a})$; or $C(R^7, R^{7a})$—$C(R^8, R^{8a})$;

$X^3$ is O; S; or N—CN;

$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl;

Optionally, one or more of the pairs $R^{1a}/R^{4a}$, $R^{1a}/R^{5a}$, $R^{4a}/R^{5a}$, $R^{7a}/R^{8a}$ form a chemical bond;

Optionally, one or more of the pairs $R^1/R^{1a}$, $R^2/R^{2a}$, $R^4/R^{4a}$, RS/$R^{5a}$, $R^7/R^{7a}$, $R^8/R^{8a}$ are joined together with the atom to which they are attached to form a $C_{3-7}$ cycloalkyl; or 4 to 7 membered heterocyclyl;

Optionally, $R^4/R^6$ are joined together with the atoms to which they are attached to form a saturated 4 to 7 membered heterocyclyl;

Optionally, one or more of the pairs $R^1/R^4$, $R^1/R^5$, $R^1/R^6$, $R^4/R^5$, $R^4/R^6$, $R^7/R^8$, $R^2/R^3$ are joined together with the atoms to which they are attached to form a ring A;

Optionally, $R^3/R^{3a}$ are joined together with the nitrogen atom to which they are attached to form a 4 to 7 membered heterocycle;

A is selected from the group consisting of phenyl; naphthyl; indenyl; indanyl; tetralinyl; $C_{3-10}$ cycloalkyl; 4 to 7 membered heterocyclyl; and 9 to 11 membered heterobicyclyl; and wherein $L^1$ is substituted with one to four groups $L^2$-Z and optionally further substituted, provided that the hydrogen marked with the asterisk in formula (I) is not replaced by a substituent; wherein $L^2$ is a single chemical bond or a spacer; and Z is a carrier group.

It was surprisingly found, that the scope of cyclization-activation by cyclic imide formation can be extended from ester to even carrier-linked amide prodrugs, despite the much greater stability of the amide bond under aqueous conditions. It was observed that N,N'-biscarboxamides linked to a nucleophile carrying moiety through one amide bond and to the drug molecule through the second amide bond exhibit autohydrolysis in a range that is useful for prodrug applications. In addition, it was discovered that linkers can be designed that include a carrier permanently attached to the N,N' biscarboxamide motif in such a fashion that cyclic imide formation can be employed as a self-activation principle in carrier-linked amide prodrug design.

Examples for such preferred cyclic cleavage products are substituted succinimide or glutarimide ring structures. Prerequisite for such cyclization activation is the presence of an amine-containing nucleophile in the linker structure and another amide bond which is not the amide prodrug bond but an amide bond substituted with a hydrogen atom.

In case of succinimide- or a glutarimide-activated prodrug cleavage, the amine-containing nucleophile serves as a neighbouring group to enhance the nucleophilicity of the nitrogen contained in the permanent amide bond which in turn attacks the prodrug amide carbonyl group and consequently induces intramolecular acylation of the permanent amide bond generating the cyclic imide ring.

Therefore preferred linker structures comprise a permanent linkage to a carrier, an amine-containing nucleophile, and a permanent amide bond with a hydrogen attached to the nitrogen of the amide bond. Corresponding carrier-linked prodrugs comprise a linker containing a permanent linkage to a carrier, an amine-containing nucleophile and said permanent amide bond, and a nitrogen containing biologically active moiety derived from the drug conjugated to the linker by means of a cleavable amide bond.

FIG. 1 shows an example of the cleavage resulting in a cyclic imide. The nitrogen of the biologically active moiety is shown as hydrogen containing amine, which results in a drug having a primary amine functional group. However also, e.g., a secondary amine may be part of the drug. For simplification reasons the one to four mandatory substituents $L^2$-Z including the carrier are not shown.

Preferred properties of the prodrug are given by a half-life of hydrolysis in aqueous buffer at pH 7.4 and 37° C. between 1 h and 3 months; similar rates of hydrolysis under physiological conditions in buffer and plasma.

The prodrug according to the present invention may show excellent in vivo/in vitro correlation of linker cleavage, a high degree of enzyme independence and can be stored at lower pH (pH dependent cleavage).

Within the meaning of the present invention the terms are used as follows.

"Biologically active moiety D" means the part of the drug linker conjugate, which results after cleavage in a drug D-H of known biological activity.

"Non-active linker" means a linker which does not show the pharmacological effects of the drug derived from the biologically active agent.

"Alkyl" means a straight-chain or branched carbon chain. Each hydrogen of an alkyl carbon may be replaced by a substituent.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl tert-butyl, or e.g. —$CH_2$—, —$CH_2$—$CH_2$—, —$CH(CH_3)$—, —$CH_2$—$CH_2$—

$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent.

Accordingly, "$C_{1-18}$ alkyl" means an alkyl chain having 1 to 18 carbon atoms and "$C_{8-18}$ alkyl" means an alkyl chain having 8 to 18 carbon atoms. Accordingly, "$C_{1-50}$ alkyl" means an alkyl chain having 1 to 50 carbon atoms.

"$C_{2-50}$ alkenyl" means a branched or unbranched alkenyl chain having 2 to 50 carbon atoms, e.g. if present at the end of a molecule: —$CH=CH_2$, —$CH=CH$—$CH_3$, —$CH_2$—$CH=CH_2$, —$CH=CH$—$CH_2$—$CH_3$, —$CH=CH$—$CH=CH_2$, or e.g. —$CH=CH$—, when two moieties of a molecule are linked by the alkenyl group. Each hydrogen of a $C_{2-50}$ alkenyl carbon may be replaced by a substituent as further specified. Accordingly, the term "alkenyl" relates to a carbon chain with at least one carbon carbon double bond. Optionally, one or more triple bonds may occur.

"$C_{2-50}$ alkynyl" means a branched or unbranched alkynyl chain having 2 to 50 carbon atoms, e.g. if present at the end of a molecule: —$C\equiv CH$, —$CH_2$—$C\equiv CH$, $CH_2$—$CH_2$—$C\equiv CH$, $CH_2$—$C\equiv C$—$CH_3$, or e.g. —$C\equiv C$— when two moieties of a molecule are linked by the alkynyl group. Each hydrogen of a $C_{2-50}$ alkynyl carbon may be replaced by a substituent as further specified. Accordingly, the term "alkynyl" relates to a carbon chain with at lest one carbon carbon triple bond. Optionally, one or more double bonds may occur.

"$C_{3-7}$ cycloalkyl" or "$C_{3-7}$ cycloalkyl ring" means a cyclic alkyl chain having 3 to 7 carbon atoms, which may have carbon-carbon double bonds being at least partially saturated, e.g. cyclopropyl, cyclobutyl, cyclopentyl, cyclohexyl, cyclohexenyl, cycloheptyl. Each hydrogen of a cycloalkyl carbon may be replaced by a substituent. The term "$C_{3-7}$ cycloalkyl" or "$C_{3-7}$ cycloalkyl ring" also includes bridged bicycles like norbonane or norbonene. Accordingly, "$C_{3-5}$ cycloalkyl" means a cycloalkyl having 3 to 5 carbon atoms.

Accordingly, "$C_{3-10}$ cycloalkyl" means a cyclic alkyl having 3 to 10 carbon atoms, e.g. $C_{3-7}$ cycloalkyl; cyclopropyl, cyclobutyl, cyclopentyl, cyclohexyl, cyclohexenyl, cycloheptyl, cyclooctyl, cyclononyl, cyclodecyl. The term "$C_{3-10}$ cycloalkyl" also includes at least partially saturated carbomono- and -bicycles.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —$S(O)$—, —$S(O)_2$—), oxygen and nitrogen (including =$N(O)$—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —$S(O)$—, —$S(O)_2$—), oxygen and nitrogen (including =$N(O)$—) and wherein the ring is linked to the rest of the molecule via a carbon or nitrogen atom. Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane.

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMEA (Europe) and/or the FDA (US) and/or any other national regulatory agency for use in animals, preferably in humans.

"Pharmaceutical composition" means one or more active ingredients, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable excipient (pharmaceutically acceptable carrier).

The term "excipient" refers to a diluent, adjuvant, or vehicle with which the therapeutic is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in "Remington's Pharmaceutical Sciences" by E. W. Martin. Such compositions will contain a therapeutically effective amount of the therapeutic, preferably in purified form, together with a suitable amount of excipient so as to provide the form for proper administration to the patient. The formulation should suit the mode of administration.

Preferably, $X^3$ is O.
Preferably, X is $N(R^4)$, $X^1$ is C and $X^3$ is O.
Preferably, $X^2$ is $C(R^7R^{7a})$.
Preferably, $L^1$ is selected from the group consisting of

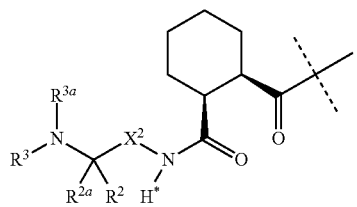

-continued

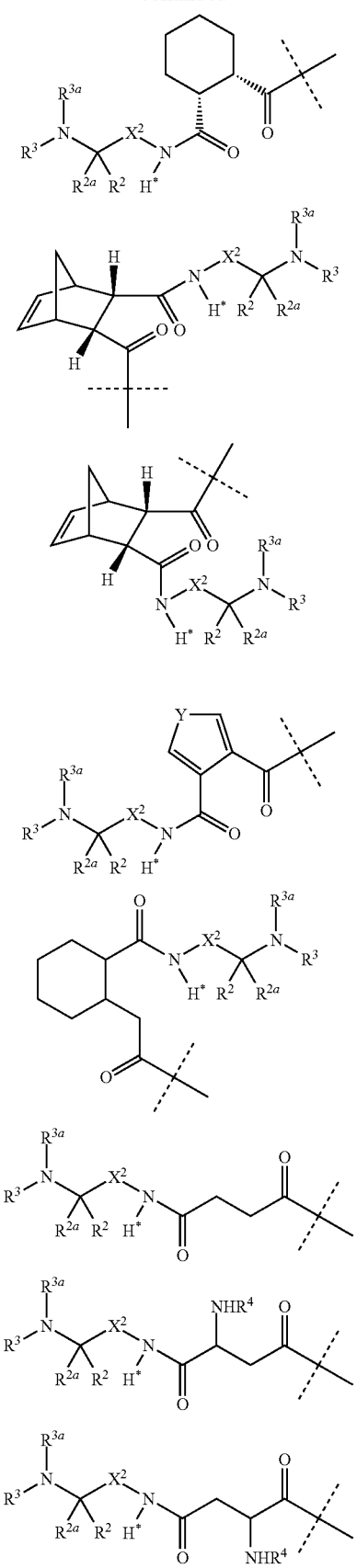

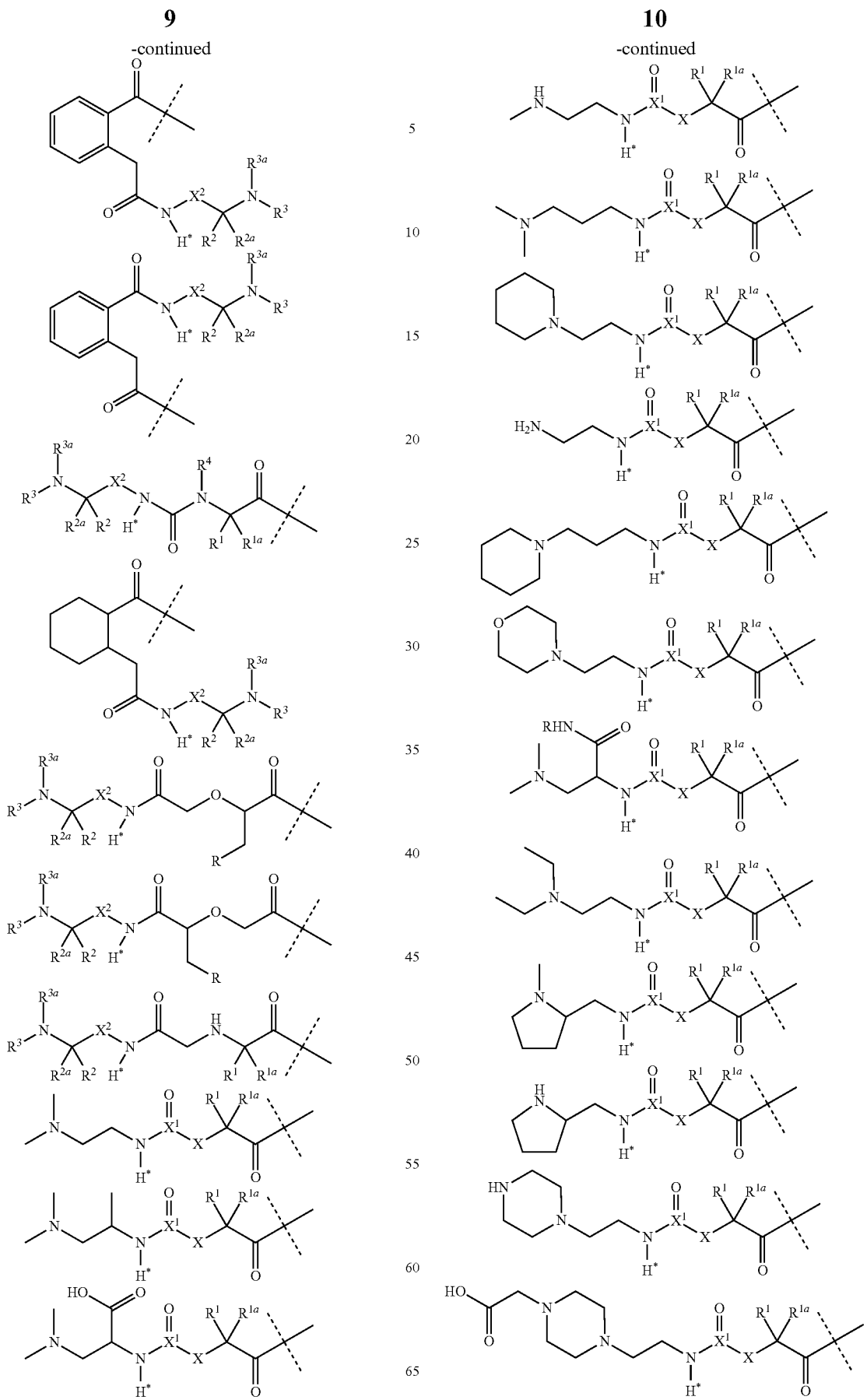

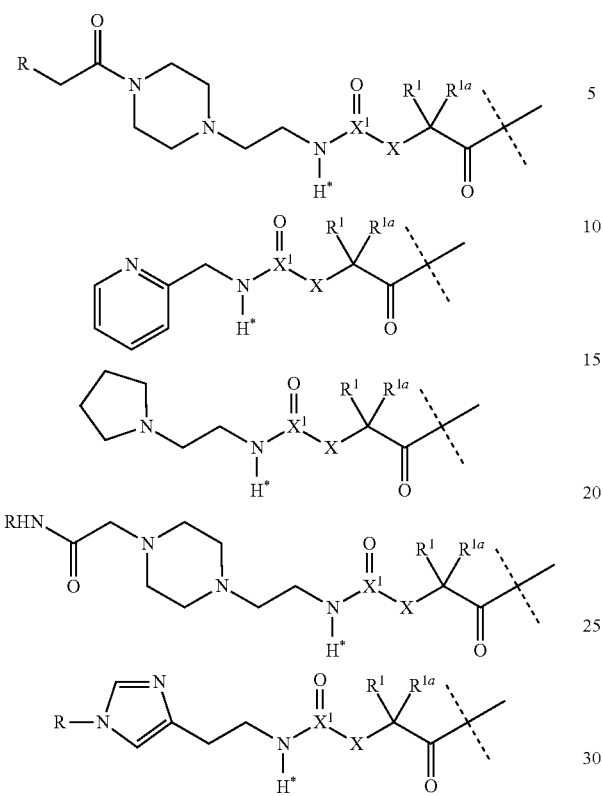
wherein R is H; or $C_{1-4}$ alkyl; Y is NH; O; or S; and $R^1$, $R^{1a}$, $R^2$, $R^{2a}$, $R^3$, $R^{3a}$, $R^4$, X, $X^1$, $X^2$ have the meaning as indicated above.
Even more preferred, $L^1$ is selected from the group consisting of
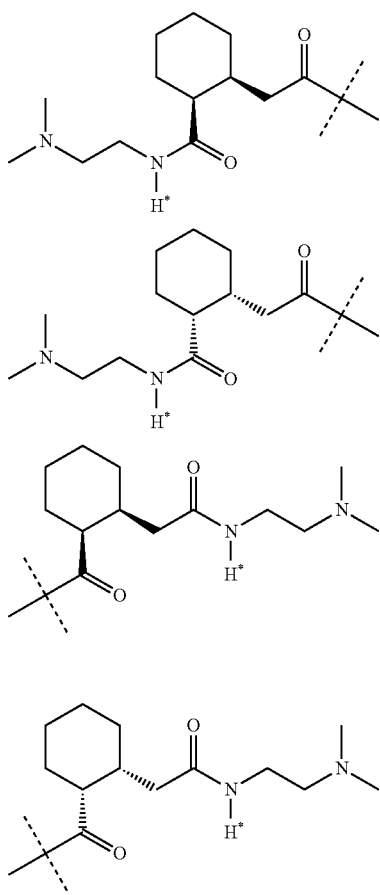
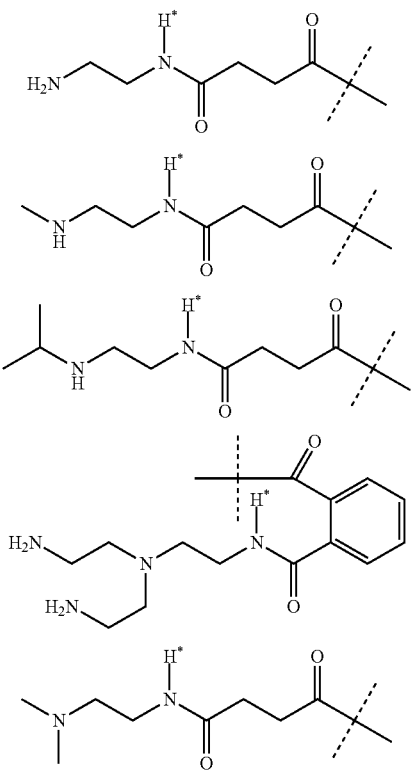
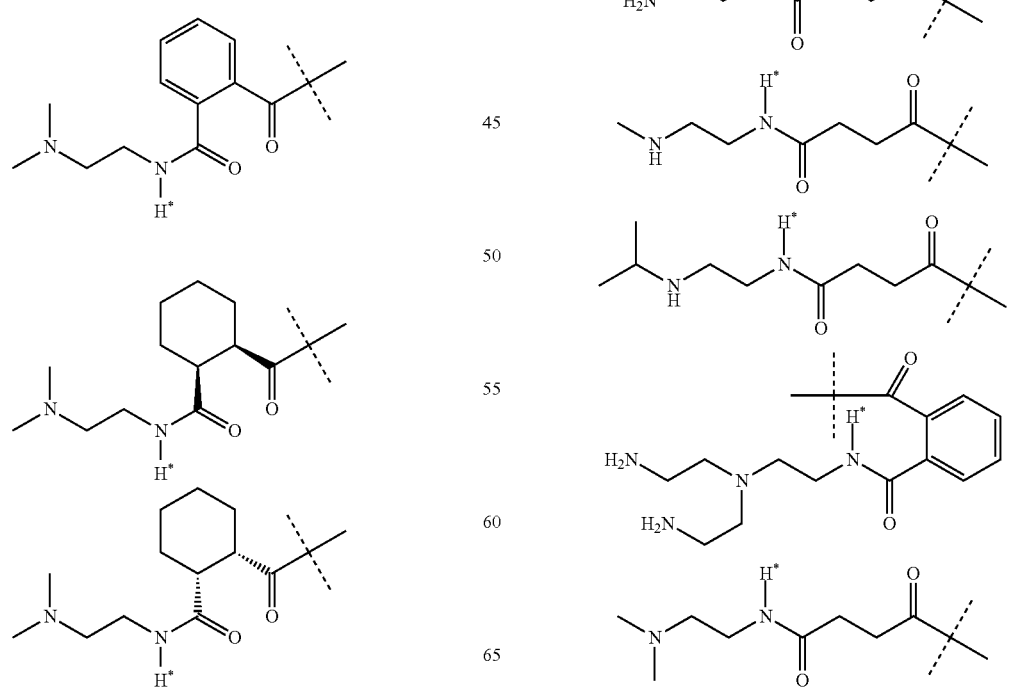

13
-continued
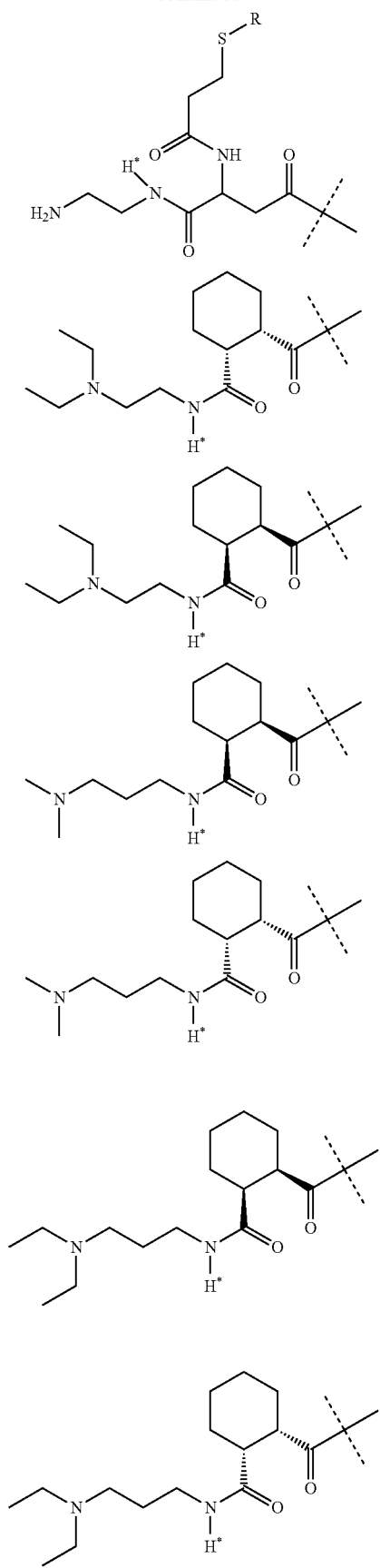
14
-continued
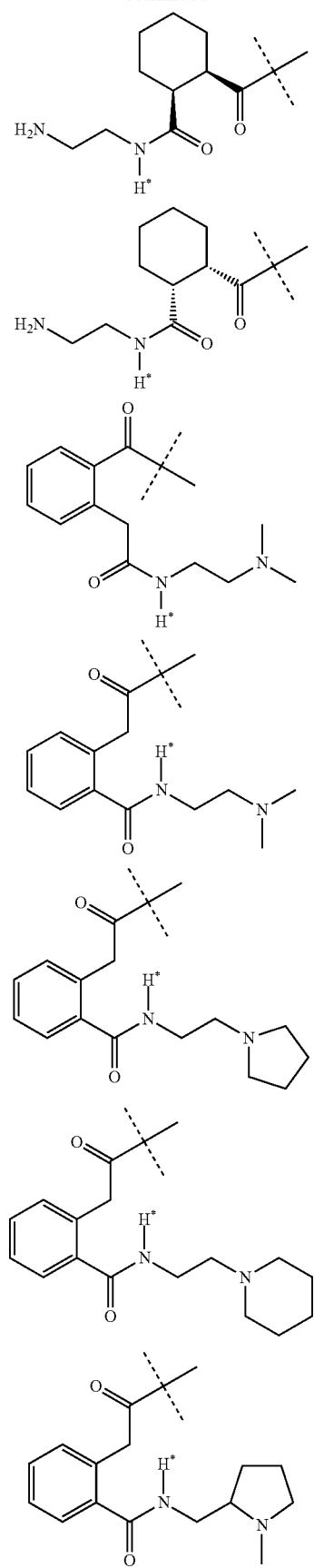

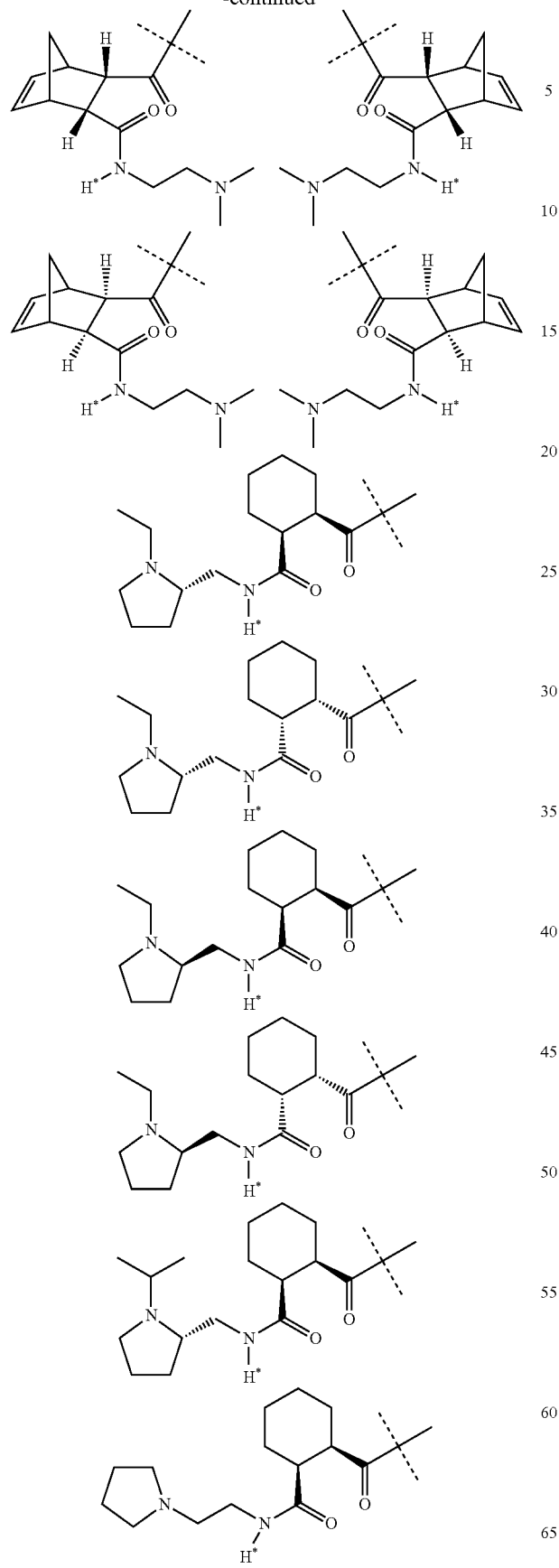
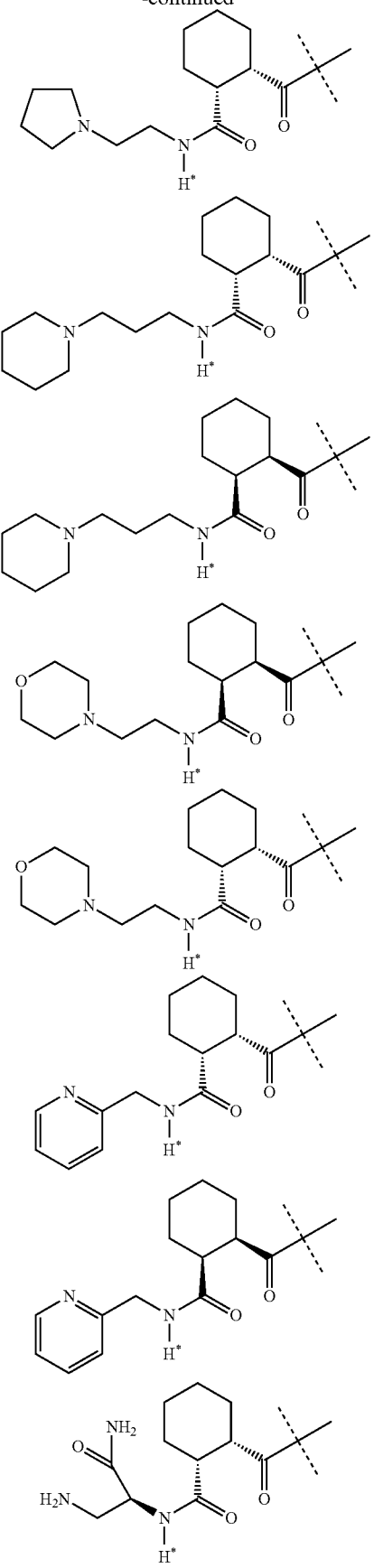

-continued
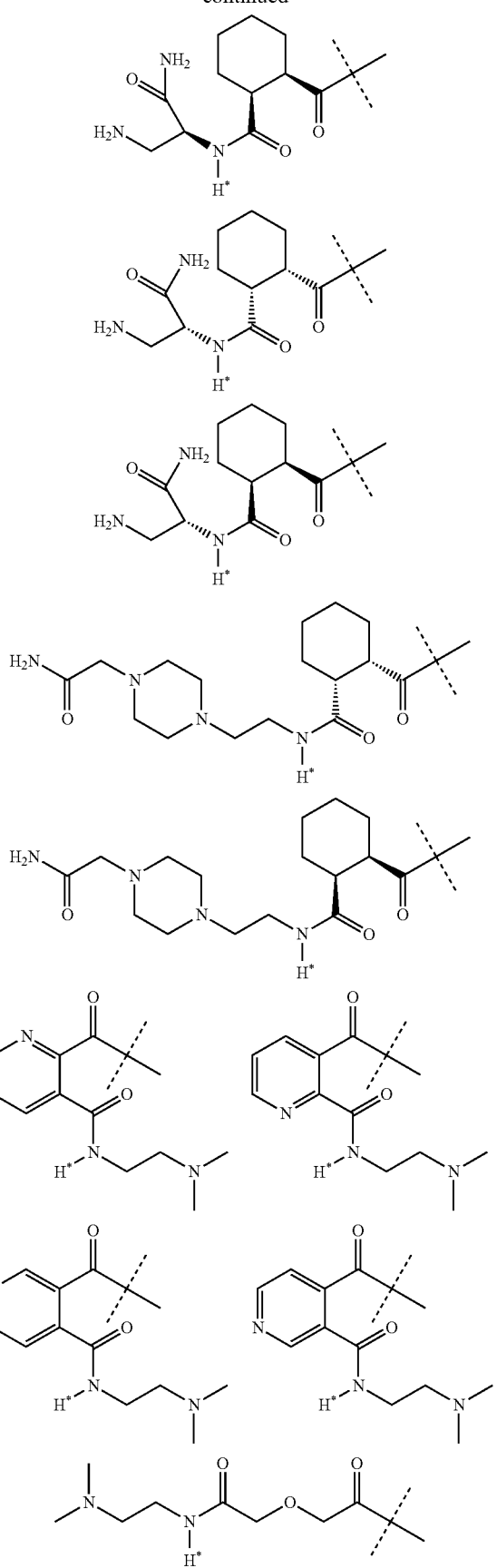
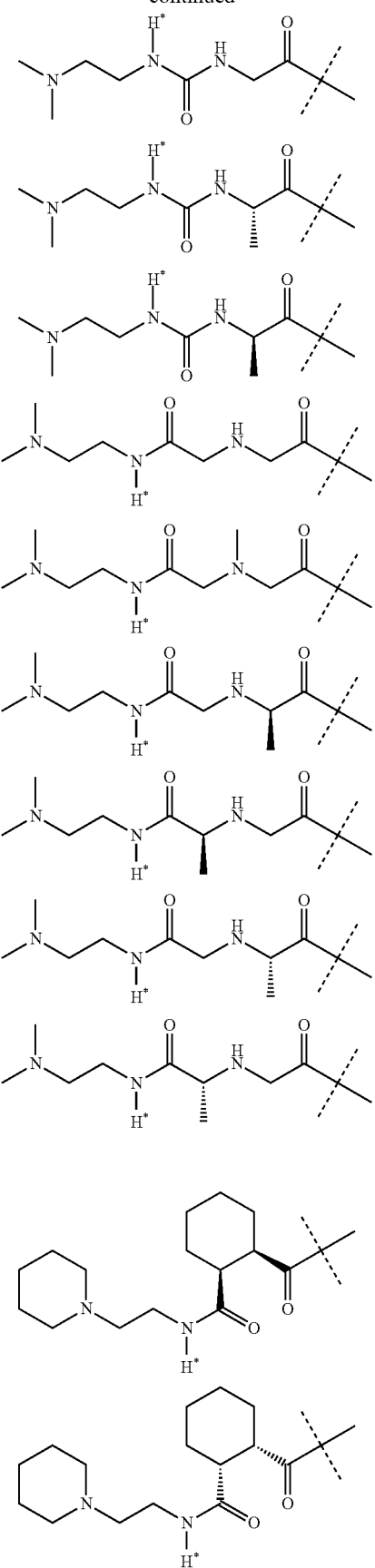

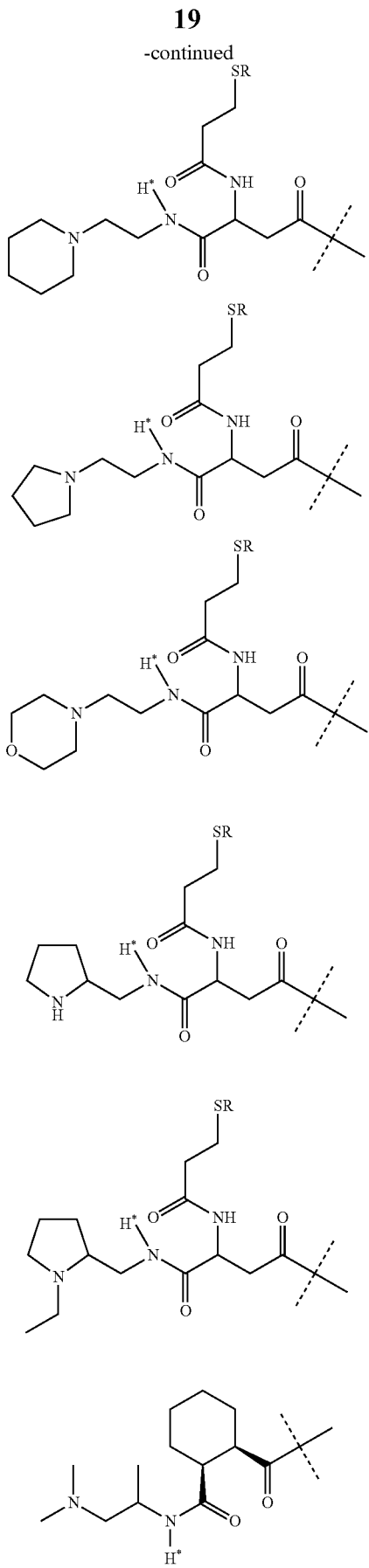
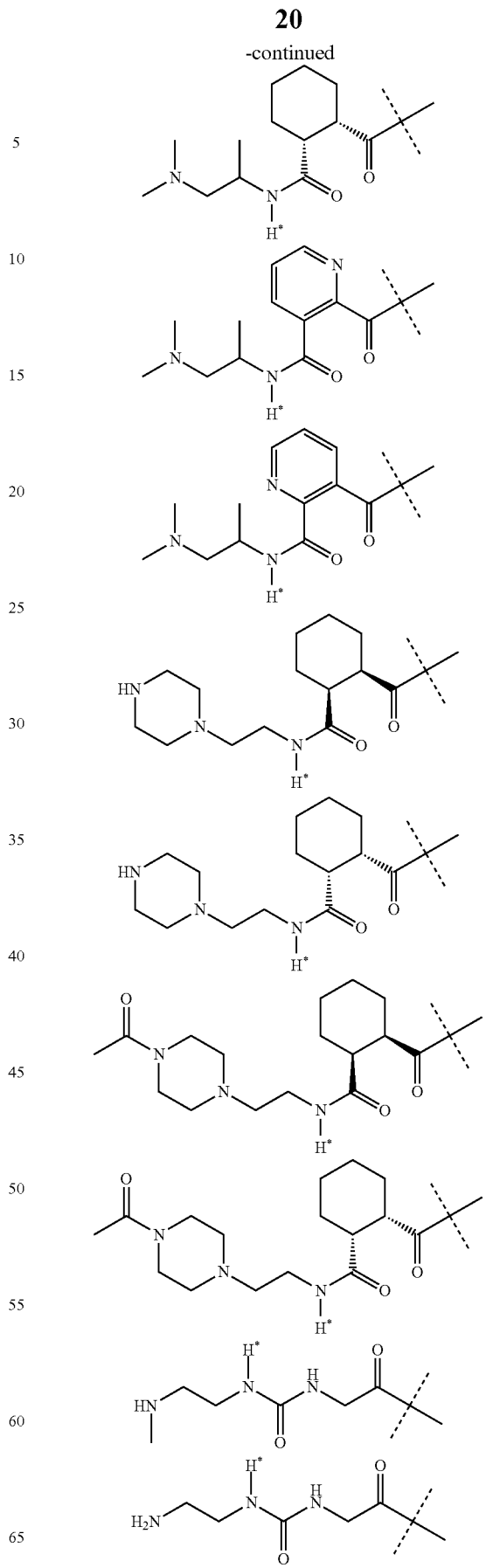

-continued

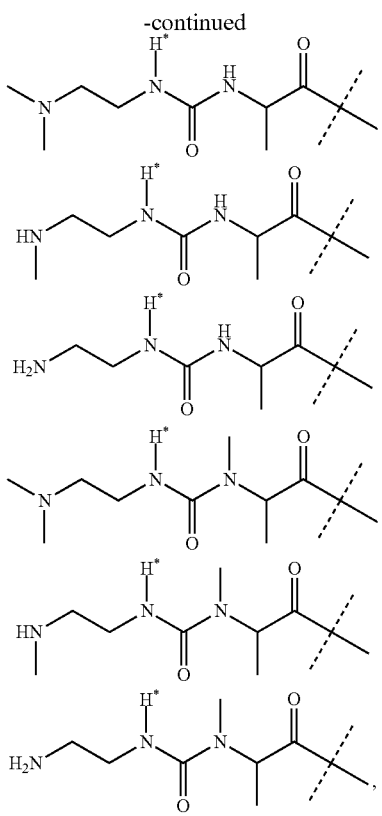

wherein R has the meaning as indicated above.

At least one (up to four) hydrogen is replaced by a group $L^2$-Z. In case more than one group $L^2$-Z is present each $L^2$ and each Z can be selected independently. Preferably, only one group $L^2$-Z is present resulting in the formula D-$L^1$-$L^2$-Z.

In general, $L^2$ can be attached to $L^1$ at any position apart from the replacement of the hydrogen marked with an asterisk in formula (I). Preferably, one to four of the hydrogen given by R, $R^1$ to $R^8$ directly or as hydrogen of the $C_{1-4}$ alkyl or further groups and rings given by the definition of R and $R^1$ to $R^8$ are replaced by $L^2$-Z.

Furthermore, $L^1$ may be optionally further substituted. In general, any substituent may be used as far as the cleavage principle is not affected.

Preferably, one or more further optional substituents are independently selected from the group consisting of halogen; CN; COOR$^S$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); SR$^9$; N(R$^9$R$^{9a}$); NO$_2$; OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)OR$^{9a}$; N(R$^9$)C(O)N(R$^{9a}$R$^{9b}$); OC(O)N(R$^9$R$^{9a}$); T; $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

R$^9$, R$^{9a}$, R$^{9b}$ are independently selected from the group consisting of H; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

T is selected from the group consisting of phenyl; naphthyl; indenyl; indanyl; tetralinyl; $C_{3-10}$ cycloalkyl; 4 to 7 membered heterocyclyl; or 9 to 11 membered heterobicyclyl, wherein T is optionally substituted with one or more $R^{10}$, which are the same or different;

$R^{10}$ is halogen; CN; oxo (=O); COOR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$R$^{12}$; S(O)R$^{12}$; N(R$^{12}$)S(O)$_2$N(R$^{12a}$R$^{12}$); SR$^{12}$; N(R$^{12}$R$^{12a}$); NO$_2$; OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O)OR$^{12a}$; N(R$^{12}$)C(O)N(R$^{12a}$R$^{12}$); OC(O)N(R$^{12}$R$^{12a}$); or $C_{1-6}$ alkyl, wherein $C_{1-6}$ alkyl is optionally substituted with one or more halogen, which are the same or different;

$R^{11}$, $R^{11a}$, $R^{12}$, $R^{12a}$, $R^{12b}$ are independently selected from the group consisting of H; or $C_{1-6}$ alkyl, wherein $C_{1-6}$ alkyl is optionally substituted with one or more halogen, which are the same or different.

The term "interrupted" means that between two carbons a group is inserted or at the end of the carbon chain between the carbon and hydrogen.

$L^2$ is a single chemical bond or a spacer. In case $L^2$ is a spacer, it is preferably defined as the one or more optional substituents defined above, provided that $L^2$ is substituted with Z.

Accordingly, when $L^2$ is other than a single chemical bond, $L^2$-Z is COOR$^S$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); SR$^9$; N(R$^9$R$^{9a}$); OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)OR$^{9a}$; N(R$^9$)C(O)N(R$^{9a}$R$^{9b}$); OC(O)N(R$^9$R$^{9a}$); T; $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of -T-, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

R$^9$, R$^{9a}$, R$^{9b}$ are independently selected from the group consisting of H; Z; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-so}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

T is selected from the group consisting of phenyl; naphthyl; indenyl; indanyl; tetralinyl; $C_{3-10}$ cycloalkyl; 4 to 7 membered heterocyclyl; or 9 to 11 membered heterobicyclyl, wherein t is optionally substituted with one or more $R^{10}$, which are the same or different;

$R^{10}$ is Z; halogen; CN; oxo (=O); $COOR^{12}$; $OR^{12}$; $C(O)R^{12}$; $C(O)N(R^{12}R^{12a})$; $S(O)_2N(R^{12}R^{12a})$; $S(O)N(R^{12}R^{12a})$; $S(O)_2R^{12}$; $S(O)R^{12}$; $N(R^{12})S(O)_2N(R^{12a}R^{12b})$; $SR^{12}$; $N(R^{12}R^{12a})$; $NO_2$; $OC(O)R^{12}$; $N(R^{12})C(O)R^{12a}$; $N(R^{12})S(O)_2R^{12a}$; $N(R^{12})S(O)R^{12a}$; $N(R^{12})C(O)OR^{12a}$; $N(R^{12})C(O)N(R^{12a}R^{12})$; $OC(O)N(R^{12a}R^{12a})$; or $C_{1-6}$ alkyl, wherein $C_{1-6}$ alkyl is optionally substituted with one or more halogen, which are the same or different;

$R^{11}, R^{11a}, R^{12}, R^{12a}, R^{11b}$ are independently selected from the group consisting of H; Z; or $C_{1-6}$ alkyl, wherein $C_{1-6}$ alkyl is optionally substituted with one or more halogen, which are the same or different;

provided that one of $R^9, R^{9a}, R^{9b}, R^{10}, R^{11}, R^{11a}, R^{12}, R^{12a}, R^{12b}$ is Z.

More preferably, $L^2$ is a $C_{1-20}$ alkyl chain, which is optionally interrupted by one or more groups independently selected from —O—; and $C(O)N(R^{3aa})$; optionally substituted with one or more groups independently selected from OH; and $C(O)N(R^{3aa}R^{3aaa})$; and wherein $R^{3aa}$, $R^{3aaa}$ are independently selected from the group consisting of H; and $C_{1-4}$ alkyl.

Preferably, $L^2$ has a molecular weight in the range of from 14 g/mol to 750 g/mol.

Preferably, $L^2$ is attached to Z via a terminal group selected from

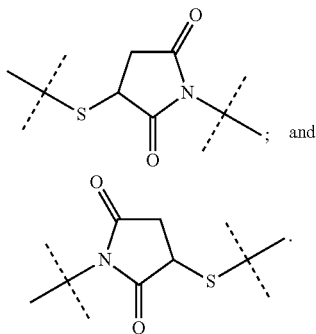
; and

In case $L^2$ has such terminal group it is furthermore preferred that $L^2$ has a molecular weight in the range of from 14 g/mol to 500 g/mol calculated without such terminal group.

Preferably, L is represented by formula (Ia)

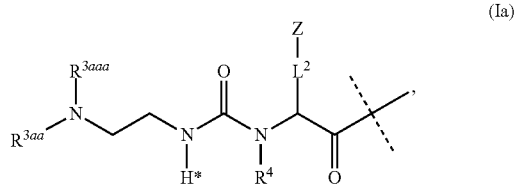
(Ia)

wherein $R^4$, $L^2$, and Z have the meaning as indicated above, and wherein $R^{3aa}$, $R^{3aaa}$ are independently selected from the group consisting of H; and $C_{1-4}$ alkyl; or are joined together with the nitrogen atom to which they are attached to form a 4 to 7 membered heterocycle. Preferably, $R^4$ is H; or methyl.

Preferably, L is represented by formula (Ib)

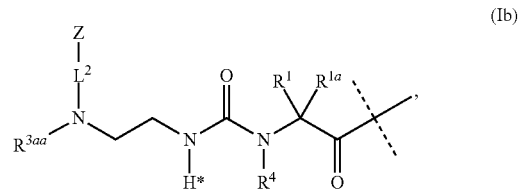
(Ib)

wherein $R^1$, $R^{1a}$, $R^4$, $L^2$ and Z have the meaning as indicated above, and wherein $R^{3aa}$ is H; or $C_{1-4}$ alkyl. Preferably, $R^4$ is H; or methyl.

Preferably, $R^1$ in formula (I) is $L^2$-Z.

Preferably, $R^3$ in formula (I) is $L^2$-Z.

Preferably, $R^3$, $R^{3a}$ in formula (I) are joined together with the nitrogen atom to which they are attached to form a 4 to 7 membered heterocycle, wherein the heterocycle is substituted with $L^2$-Z.

Preferably, D-H is a small molecule bioactive agent or a biopolymer.

Preferably, D-H is a biopolymer selected from the group of biopolymers consisting of proteins, polypeptides, oligonucleotides, and peptide nucleic acids.

"Oligonucleotides" means either DNA, RNA, single-stranded or double-stranded, siRNA, miRNA, aptamers, and any chemical modifications thereof with preferably 2 to 1000 nucleotides. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping and change of stereochemistry.

Preferably, D-H is a polypeptide selected from the group of polypeptides consisting of ACTH, adenosine deaminase, agalsidase, alfa-1 antitrypsin (AAT), alfa-1 proteinase inhibitor (API), alteplase, amylins (amylin, symlin), anistreplase, ancrod serine protease, antibodies (monoclonal or polyclonal, and fragments or fusions), antithrombin III, antitrypsins, aprotinin, asparaginases, atosiban, biphalin, bivalirudin, bone-morphogenic proteins, bovine pancreatic trypsin inhibitor (BPTI), cadherin fragments, calcitonin (salmon), collagenase, complement C1 esterase inhibitor, conotoxins, cytokine receptor fragments, DNase, dynorphine A, endorphins, enfuvirtide, enkephalins, erythropoietins, exendins, factor VII, factor VIIa, factor VIII, factor VIIIa, factor IX, fibrinolysin, fibroblast growth factor (FGF), growth hormone releasing peptide 2 (GHRP2), fusion proteins, follicle-stimulating hormones, gramicidin, ghrelin, desacyl-ghrelin, granulocyte colony stimulating factor (G-CSF), galactosidase, glucagon, glucagon-like peptides, glucocerebrosidase, granulocyte macrophage colony stimulating factor (GM-CSF), human heat shock proteins (HSP), phospho lipase-activating protein (PLAP), gonadotropin chorionic (hCG), hemoglobins, hepatitis B vaccines, hirudin, human serine protease inhibitor, hyaluronidases, idurnonidase, immune globulins, influenza vaccines, interleukins (1 alfa, 1 beta, 2, 3, 4, 6, 10, 11, 12, 13, 21), IL-1 receptor antagonist (rhIL-1ra), insulins, insulin like growth factors, insulin-like growth factor binding protein (rhIGFBP), interferons (alfa 2a, alfa 2b, alfa 2c, beta 1a, beta 1b, gamma 1a, gamma 1b), intracellular adhesion molecule, keratinocyte growth factor (KGF), P-selectin glycoprotein ligand (PSGL), transforming growth factors, lactase, leptin, leuprolide, levothyroxine, luteinizing hormone, lyme vaccine, natriuretic peptides (ANP, BNP, CNP and fragments), neuropeptide Y, pancrelipase, pancreatic polypeptide, papain, parathyroid hormone, PDGF, pepsin, peptide YY, platelet activating factor acetylhydrolase (PAF-AH), prolactin, protein C, thymalfasin, octreotide, secretin, sermorelin, soluble tumor necorsis factor receptor (TNFR), superoxide dismutase (SOD), somatropins (growth hormone), somatoprim, somatostatin, streptokinase, sucrase, terlipressin, tetanus toxin fragment, tilactase, thrombins, thymosin, thyroid stimulating hormone, thyrotropin, tumor necrosis factor (TNF), TNF receptor-IgG Fc, tissue plasminogen activator (tPA), TSH, urodilatin, urate oxidase, urokinase, vaccines, vascular endothelial growth factor (VEGF), vasoactive intestinal peptide, vasopressin, ziconotide, lectin and ricin.

Preferably, D-H is a protein prepared by recombinant DNA technologies.

Preferably, D-H is a protein selected from the group of proteins consisting of antibody fragments, single chain antigen binding proteins, catalytic antibodies and fusion proteins.

Preferably, D-H is a small molecule bioactive agent selected from the group of agents consisting of central nervous system-active agents, anti-infective, anti-allergic, immunomodulating, anti-obesity, anticoagulants, antidiabetic, anti-neoplastic, antibacterial, anti-fungal, analgesic, contraceptive, anti-inflammatory, steroidal, vasodilating, vasoconstricting, and cardiovascular agents with at least one primary or secondary amino group.

Preferably, D-H is a small molecule bioactive agent selected from the group of agents consisting of acarbose, alaproclate, alendronate, amantadine, amikacin, amineptine, aminoglutethimide, amisulpride, amlodipine, amotosalen, amoxapine, amoxicillin, amphetamine, amphotericin B, ampicillin, amprenavir, aminone, anileridine, apraclonidine, apramycin, articaine, atenolol, atomoxetine, avizafone, baclofen, benazepril, benserazide, benzocaine, betaxolol, bleomycin, bromfenac, brofaromine, carvedilol, cathine, cathinone, carbutamid, cefalexine, clinafloxacin, ciprofloxacin, deferoxamine, delavirdine, desipramine, daunorubicin, dexmethylphenidate, dexmethylphenidate, diaphenylsulfon, dizocilpine, dopamin, dobutamin, dorzolamide, doxorubicin, duloxetine, eflornithine, enalapril, epinephrine, epirubicin, ergoline, ertapenem, esmolol, enoxacin, ethambutol, fenfluramine, fenoldopam, fenoterol, fingolimod, flecamide, fluvoxamine, fosamprenavir, frovatriptan, furosemide, fluoexetine, gabapentin, gatifloxacin, gemiflocacin, gentamicin, grepafloxacin, hexylcaine, hydralazine, hydrochlorothiazide, icofungipen, idarubicin, imiquimod, inversine, isoproterenol, isradipine, kanamycin A, ketamin, labetalol, lamivudine, levobunolol, levodopa, levothyroxine, lisinopril, lomefloxacin, loracarbef, maprotiline, mefloquine, melphalan, memantine, meropenem, mesalazine, mescaline, methyldopa, methylenedioxymethamphetamine, metoprolol, milnacipran, mitoxantron, moxifloxacin, norepinephrine, norfloxacin, nortriptyline, neomycin B, nystatin, oseltamivir, pamidronic acid, paroxetine, pazufloxacin, pemetrexed, perindopril, phenmetrazine, phenelzine, pregabalin, procaine, pseudoephedrine, protriptyline, reboxetine, ritodrine, sabarubicin, salbutamol, serotonin, sertraline, sitagliptin, sotalol, spectinomycin, sulfadiazin, sulfamerazin, sertraline, sprectinomycin, sulfalen, sulfamethoxazol, tacrine, tamsulosin, terbutaline, timolol, tirofiban, tobramycin, tocamide, tosufloxacin, trandolapril, tranexamic acid, tranylcypromine, trimerexate, trovafloxacin, valaciclovir, valganciclovir, vancomycin, viomycin, viloxazine, and zalcitabine.

Preferably, Z is a polymer of at least 500 Da or a $C_{8-18}$ alkyl group.

Preferably, Z is selected from the group of optionally crosslinked polymers consisting of poly(propylene glycol), poly(ethylene glycol), dextran, chitosan, hyaluronic acid, alginate, xylan, mannan, carrageenan, agarose, cellulose, starch, hydroxyalkyl starch (HAS), poly(vinyl alcohols), poly(oxazolines), poly(anhydrides), poly(ortho esters), poly(carbonates), poly(urethanes), poly(acrylic acids), poly(acrylamides), poly(acrylates), poly(methacrylates), poly(organophosphazenes), polyoxazoline, poly(siloxanes), poly(amides), poly(vinylpyrrolidone), poly(cyanoacrylates), poly(esters), poly(iminocarbonates), poly(amino acids), collagen, gelatin, hydrogel or a blood plasma protein, and copolymers thereof.

Preferably, Z is a protein.

Preferably, Z is a protein selected from the group consisting of albumin, transferrin, immunoglobulin.

Preferably, Z is a linear or branched poly(ethylene glycol) with a molecular weight from 2,000 Da to 150,000 Da.

Even more preferred is a prodrug of the present invention, wherein D-H is a GLP-1 receptor agonist; L is $L^1$ represented by formula (I) as indicated above; and Z is a hydrogel. Even more preferably, in formula (I) X is $N(R^4)$, $X^1$ is C and $X^3$ is O. Even more preferably, L is represented by formula (Ia) as indicated above.

GLP-1 is one of the intestinal peptide hormones that are released into the circulatory system after food intake. It augments the postprandial release of insulin, when nutritions (especially carbohydrates) are absorbed and their level postprandially elevated. GLP-1 associates with GLP-1 receptor sites located on pancreatic β-cells and elevates endogenous cAMP levels in a dose dependent manner. In isolated rat islets in the presence of above normoglycemic glucose levels, GLP-1 stimulates the release of insulin. A therapeutic potential for GLP-1 in type 2 diabetes patients was suggested before, owing to the profound efficacy of this insulinotropic peptide to stimulate secretion of insulin when glucose levels are elevated and to cease doing so upon return to normoglycemia. The antidiabetogenic effect of glucagon-like peptide-1 (7-36) amide in normal subjects and patients with diabetes mellitus is described e.g. in N. Engl. J. Med. 326 (20):1316-1322. In vitro studies and animal experiments suggest that GLP-1 improves insulin sensitivity and has an anabolic effect on pancreatic β-cells. In humans, GLP-1 was also reported to suppress glucagon secretion, decelerate gastric emptying, and induce satiety, leading to weight loss if administered for weeks and months.

Exendin-4 is reported to associate with GLP-1 receptors located on pancreatic beta-cells with 2.5 times higher affinity than GLP-1. In isolated rat islets and beta-cells in presence of glucose, exendin enhances secretion of insulin in a dose-dependent fashion. Exendin-4 is a high potency agonist and truncated exendin-(9-39)-amide an antagonist at the glucagon-like peptide 1-(7-36)-amide receptor of insulin-secreting beta-cells (see J. Biol. Chem. 268(26):19650-19655). Studies in type 2 diabetic rodents revealed that exendin-4 is 5530-fold more potent than GLP-1 in lowering blood glucose levels. Also, the duration of glucose-lowering action after a single administration of exendin-4 is significantly longer compared to GLP-1 (see e.g. Diabetes 48(5):1026-1034). Plasma half-life of exendin-4 in humans was described to be only 26 minutes. Exendin-4 reduces fasting and postprandial glucose and decreases energy intake in healthy volunteers (see e.g. Am. J. Physiol. Endocrinol. Metab. 281(1):E155-61).

Accordingly in an even more preferred embodiment the GLP-1 receptor agonist is Exendin-4.

Hydrogels to be used are known in the art. Suitable hydrogels may be used which are described in WO-A 2006/003014. Accordingly, a hydrogel may be defined as a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water which allow them to swell in aqueous media. The chains of the network are connected in such a fashion that pores exist and that a substantial fraction of these pores are of dimensions between 1 nm and 1000 nm.

Another object of the present invention is a pharmaceutical composition comprising a prodrug of the present invention or a pharmaceutical salt thereof together with a pharmaceutically acceptable excipient.

Yet another object of the present invention is a prodrug of the present invention or a pharmaceutical composition of the present invention for use as a medicament.

Yet another object of the present invention is a method of treating, controlling, delaying or preventing in a mammalian patient in need of the treatment of one or more conditions comprising administering to said patient a therapeutically effective amount of a prodrug of the present invention or a pharmaceutical composition of the present invention or a pharmaceutically acceptable salt thereof.

Another object of the present invention is a prodrug precursor of formula Act-L, wherein L has the meaning as indicated above and Act is a leaving group.

Preferably, Act is chloride, bromide, fluoride, nitrophenoxy, imidazolyl, N-hydroxysuccinimidyl, N-hydroxybenzotriazolyl, N-hydroxyazobenzotriazolyl, pentafluorophenoxy, 2-thiooxo-thiazolidinyl, or N-hydroxysulfosuccinimidyl.

EXAMPLES

Materials and Methods

Materials: Side chain protected Exendin-4 (J. Eng et al., J. Biol. Chem. 1992, 267, 11, 7402-7405) on Rink amide resin, side chain protected BNP-32a (human, Cys10 and Cys26 exchanged for Ala) on chlorotrityl resin, side chain protected BNP-32b with ivDde side-chain protecting group on Lys 14 (human, Cys10 and Cys26 exchanged for Ala) on chlorotrityl resin, and side chain protected human growth hormone releasing factor fragment 1-29 amide (GRF(1-29)) on Rink amide (each synthesized by Fmoc-strategy) were obtained from Peptide Specialty Laboratories GmbH, Heidelberg, Germany. Standard side chain protecting groups were used except for Lys27 of Exendin-4 and Lys21 of GRF(1-29) where Mmt side-chain protecting groups were used.

40 kDa methoxy poly(ethylene glycol) maleimido-propionamide (PEG40 kDa-maleimide) was obtained from Chirotech Technology Ltd, Cambridge, UK.

2-Chlorotrityl chloride resin, Sieber amide resin and amino acids were from Merck Biosciences GmbH, Schwalbach/Ts, Germany, if not stated otherwise. Fmoc-D-Homocysteine (Trt)-OH and S-Trityl-3-mercaptopropionic acid (Trt-MPA) were obtained from Bachem AG, Bubendorf, Switzerland. O—(N-Fmoc-2-aminoethyl)-O'-(2-carboxyethyl)-undecaethyleneglycol (Fmoc-Pop-OH) was obtained from Polypure AS, Oslo, Norway. Fmoc-4-(2-aminoethyl)-1-carboxymethyl-piperazine (Fmoc-Acp-OH) was purchased from NeoMPS SA, Strasbourg, France. cis-Cyclohexane-1,2-dicarboxylic anhydride was obtained from Alfa Aesar GmbH & Co KG, Karlsruhe, Germany.

All other chemicals were from Sigma-ALDRICH Chemie GmbH, Taufkirchen, Germany.

Solid phase synthesis was performed on 2-Chlorotrityl chloride resin with a loading of 1.3 mmol/g or Sieber amide resin with a loading of 0.55 mmol/g. Syringes equipped with polypropylene frits were used as reaction vessels.

Loading of the first amino acid to resins was performed according to manufacturer's instructions.

Fmoc Deprotection:

For Fmoc protecting-group removal, the resin was agitated with Feb. 2, 1996 (v/v/v) piperidine/DBU/DMF (two times, 10 min each) and washed with DMF (ten times).

ivDde Deprotection:

For ivDde protecting-group removal, the resin was agitated with 98/2 (v/v) DMF/hydrazine hydrate (3 times, 10 min each) and washed with DMF (ten times).

Boc Protection:

The N-terminus of a peptide was boc-protected by agitating the resin with 30 eq $(boc)_2O$ and 60 eq pyridine in DCM. After 1 h the resin was washed with DCM (10 times).

Standard Coupling Condition for Acids:

Coupling of acids (aliphatic acids, Fmoc-amino acids) to free amino groups on resin was achieved by agitating resin with 3 eq of acid, 3 eq PyBOP and 6 eq DIEA in relation to free amino groups on resin (calculated based on theoretical loading of the resin) in DMF at room temperature. After 1 hour resin was washed with DMF (10 times).

3-Maleimido Propionic Acid Coupling:

Coupling of 3-maleimido propionic acid to free amino groups on resin was achieved by agitating resin with 2 eq of acid, 2 eq DIC and 2 eq HOBt in relation to free amino groups in DMF at room temperature. After 30 min, resin was washed with DMF (10 times).

Standard Protocol for Synthesis of Ureas on Resin:

Synthesis of ureas on resin was achieved by agitating resin with 2.5 eq of bis(pentafluorophenyl) carbonate, 5 eq DIEA, and 0.25 eq DMAP in relation to free amino groups in DCM/ACN 1/1 at room temperature. After 15 min resin was washed with DMF (10 times). 5 eq of amine was dissolved in DMF. Mixture was added to resin and agitated for 60 min at room temperature. Resin was washed with DMF (10 times).

Cleavage Protocol for Sieber Amide Resin:

Upon completed synthesis, the resin was washed with DCM (10 times), dried in vacuo and treated repeatedly (five times a 15 minutes) with 97/2/1 (v/v) DCM/TES/TFA. Eluates were combined, volatiles were removed under a nitrogen stream and product was purified by RP-HPLC. HPLC fractions containing product were combined and lyophilized.

Cleavage Protocol for 2-Chlorotrityl Chloride Resin:

Upon completed synthesis, the resin was washed with DCM, dried in vacuo and treated two times for 30 minutes with 6/4 (v/v) DCM/HFIP. Eluates were combined, volatiles were removed under a nitrogen stream and product was purified by RP-HPLC. HPLC fractions containing product were combined and lyophilized.

Cleavage Protocol for Rink Amide Resin:

Upon completed synthesis, the resin was washed with DCM, dried in vacuo and treated with 2 ml of TFA cleavage cocktail (TFA/TES/Water/DTT 95/2/2/1) per 100 mg resin for 60 min at room temperature. Volatiles were removed under a nitrogen stream. Unpolar side products and protecting groups were removed by precipitating peptide from diethyl ether. Precipitate was dried in vacuo and dissolved in ACN/water 1/1 and purified by RP-HPLC.

Amine containing products obtained as TFA salts were converted to the corresponding HCl salts using ion exchange resin (Discovery DSC-SAX, Supelco, USA). This step was performed in case the residual TFA was expected to interfere with e.g. a subsequent coupling reactions.

RP-HPLC Purification:

RP-HPLC was done on a 100×20 or a 100×40 mm C18 ReproSil-Pur 3000DS-3 5μ column (Dr. Maisch, Ammerbuch, Germany) connected to a Waters 600 HPLC System and Waters 2487 Absorbance detector. Linear gradients of solution A (0.1% TFA in H$_2$O) and solution B (0.1% TFA in acetonitrile) were used. HPLC fractions containing product were lyophilized.

Analytics: Electrospray ionization mass spectrometry (ESI-MS) was performed on a Waters ZQ 4000 ESI instrument and spectra were, if necessary, interpreted by Waters software MaxEnt.

Size exclusion chromatography (SEC) was performed using an Amersham Bioscience AEKTAbasic system equipped with a Superdex200 10/300 column (Amersham Bioscience/GE Healthcare), if not stated otherwise. 10 mM sodium phosphate, 140 mM NaCl, pH 7.4, 3 mM EDTA was used as mobile phase For Cation Exchange Chromatography, an Amersham Bioscience AEKTAbasic system was equipped with a Source 15S filled HR16/10 column (Amersham Bioscience/GE Healthcare).

Desalting was performed using an Amersham Bioscience AEKTAbasic system equipped with a HiPrep 26/10 Desalting column and 0.1% acetic acid in water as mobile phase.

In vitro linker hydrolysis and release of drug: Compounds were dissolved in buffer A (10 mM sodium phosphate, 140 mM NaCl, pH 7.4, 3 mM EDTA) or buffer B (0.1 M Acetat 3 mM EDTA, pH 4.0), and solution was filtered through a 0.2 μm filter and incubated at 37° C. Samples were taken at time intervals and analyzed by RP-HPLC at 215 nm and ESI-MS. UV-signals correlating to liberated drug molecule were integrated and plotted against incubation time. In case of identical retention times of prodrug and drug, ratio of mass signals was used to determine release kinetics.

For hydrogel conjugates, compounds were suspended in buffer A and incubated at 37° C. Samples were taken after centrifugation of the suspension and analyzed by RP-HPLC at 215 nm. UV-signals correlating to liberated drug molecule were integrated and plotted against incubation time.

Curve-fitting software was applied to estimate the corresponding halftime of release.

Example 1

Synthesis of Fatty Acid Carrier (1)

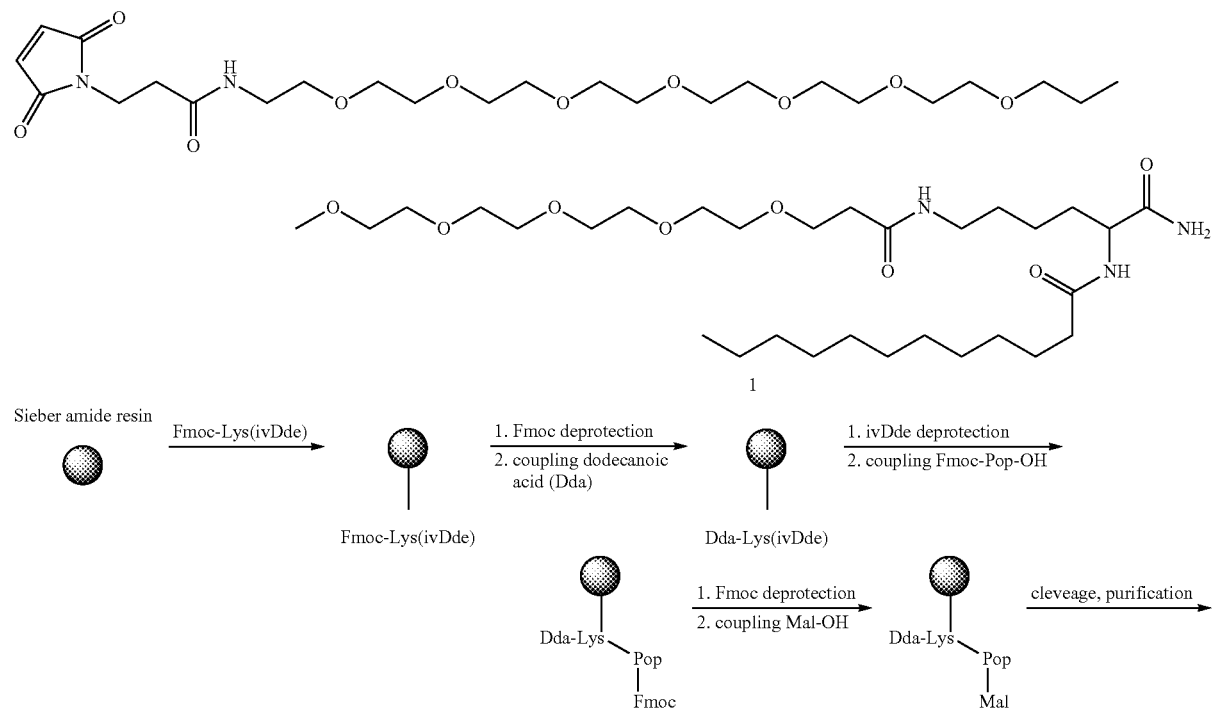

1 was synthesized on sieber amide resin (477 mg, 0.262 mmol) by coupling of Fmoc-Lys(ivDde)-OH, fmoc deprotection, coupling of dodecanoic acid, ivDde deprotection, coupling of Fmoc-Pop-OH, fmoc deprotection, coupling of 3-maleimido propionic acid, cleavage from resin and purification as depicted above and described in "Materials and Methods".

Yield: 128 mg (0.119 mmol).

MS: m/z 1101.0=[M+Na]$^+$ (MW calculated=1078.4 g/mol).

Example 2

Synthesis of Linker Reagent (2)

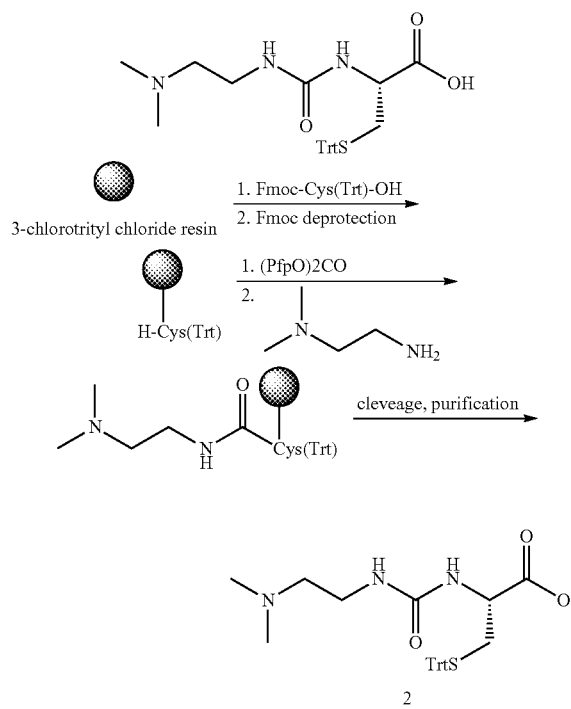

Linker reagent 2 was synthesized on 3-chlorotrityl chloride resin (300 mg, 0.39 mmol) by loading of resin with Fmoc-Cys(Trt)-OH, fmoc deprotection, and on-resin urea formation using N,N-dimethyl-ethylenediamine as amine, cleavage from resin as depicted above and described in "Materials and Methods". For RP-HPLC separation, 0.01% HCl in water was used as solution A and 0.01% HCl in acetonitrile was used as solution B.

Yield: 82 mg of HCl salt (0.16 mmol)

MS: m/z 478.2=[M+H]$^+$ (MW calculated=477.6 g/mol).

Example 3

Synthesis of Exendin-4 Linker Intermediate (3)

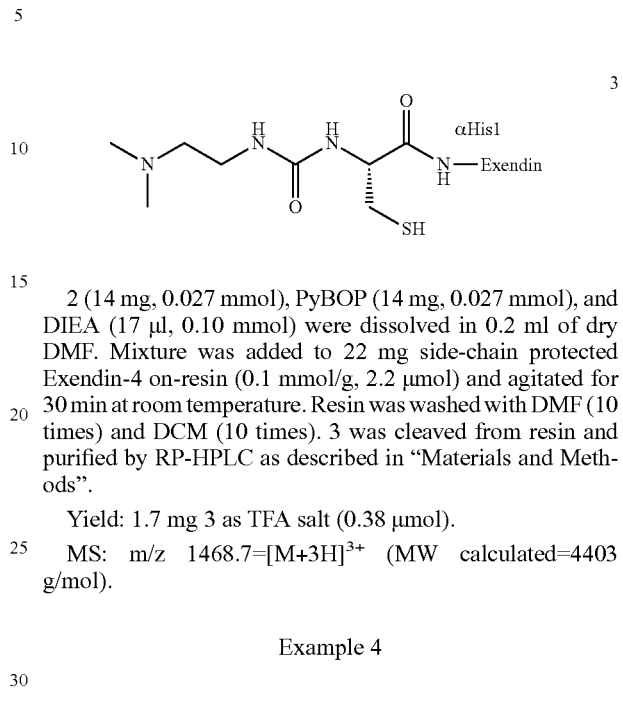

2 (14 mg, 0.027 mmol), PyBOP (14 mg, 0.027 mmol), and DIEA (17 µl, 0.10 mmol) were dissolved in 0.2 ml of dry DMF. Mixture was added to 22 mg side-chain protected Exendin-4 on-resin (0.1 mmol/g, 2.2 µmol) and agitated for 30 min at room temperature. Resin was washed with DMF (10 times) and DCM (10 times). 3 was cleaved from resin and purified by RP-HPLC as described in "Materials and Methods".

Yield: 1.7 mg 3 as TFA salt (0.38 µmol).

MS: m/z 1468.7=[M+3H]$^{3+}$ (MW calculated=4403 g/mol).

Example 4

Synthesis of Fatty Acid-PEG-Linker-Exendin-4 Conjugate (4)

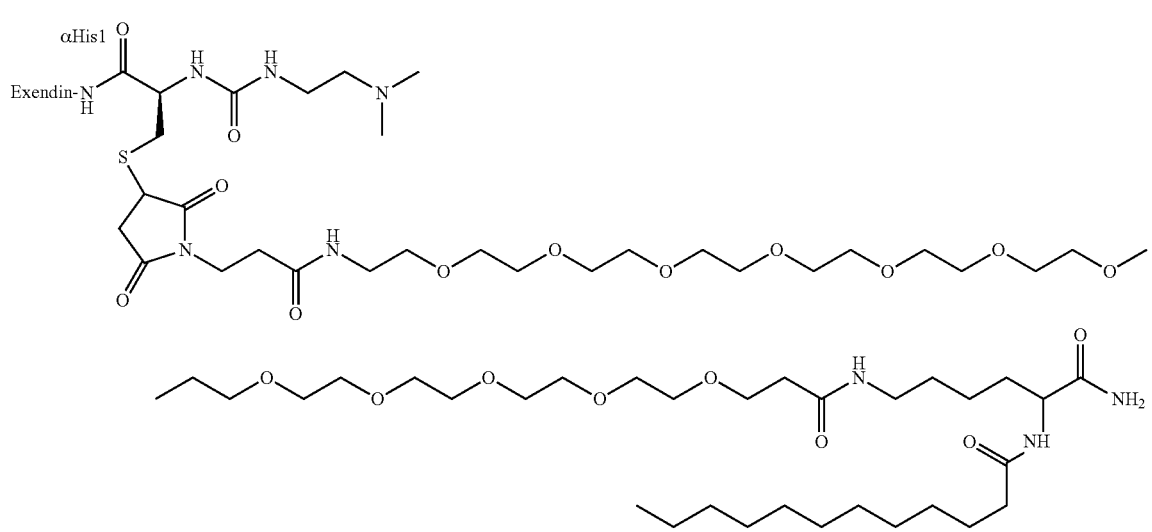

3 (1.7 mg, 0.38 µmol) and 1 (0.6 mg, 0.58 µmol) were dissolved in 500 µl of acetonitrile/water 7/3 (v/v). 40 µl of 0.5 M phosphate buffer (pH 7.4) were added and the mixture was incubated at RT for 10 min. Conjugate 4 was purified by RP-HPLC.

MS: m/z 1828.7=[M+3H]$^{3+}$ (MW calculated=5480 g/mol).

Example 5

Synthesis of Linker Intermediate (5a)

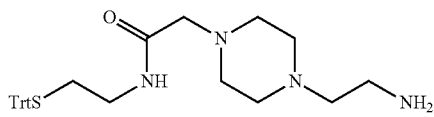

5a

Fmoc-Acp-OH.2HCl (100 mg, 0.21 mmol) was suspended in 400 µl DMF/DMSO 1/1 (v/v). S-tritylcysteamine.HCl (75 mg, 0.21 mmol), PyBOP (109 mg, 0.21 mmol) and DIEA (146 µl, 0.86 mmol) were added and mixture was agitated for 60 min at RT. Fmoc group was removed by adding 75 µl piperidine and 25 µl DBU. After 15 min mixture was hydrolyzed and acidified (AcOH) and compound was purified by RP-HPLC. After lyophilization 98 mg (0.14 mmol, double TFA salt) were obtained.

MS: m/z 511.6=[M+Na]$^+$ (MW calculated=488.7 g/mol).

Synthesis of cis-Cyclohexane Diacarboxylic Acid Amoxapine Monoamide (5b)

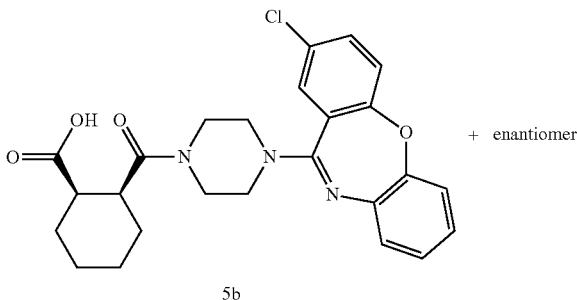 [SMILES: O=C(O)[C@@H]1CCCC[C@@H]1C(=O)N1CCN(C2=Nc3ccccc3Oc3ccc(Cl)cc32)CC1]

5b

Amoxapine (200 mg, 0.64 mmol) and cis-cyclohexane-1, 2-dicarboxylic anhydride (108 mg, 0.70 mmol) were dissolved in 700 µl of dry DMF. Pyridine (130 µl, 1.6 mmol) was added and mixture was stirred for 60 min at RT. Mixture was quenched with 2 ml of acetonitrile/acetic acid/water (1/1/1) and purified by RP-HPLC. After lyophilization 344 mg (0.49 mmol, double TFA salt) of 5b were obtained.

MS: m/z 468.5=[M+H]$^+$ (MW calculated=468.0 g/mol).

Synthesis of Linker-Amoxapine Conjugate (5c)

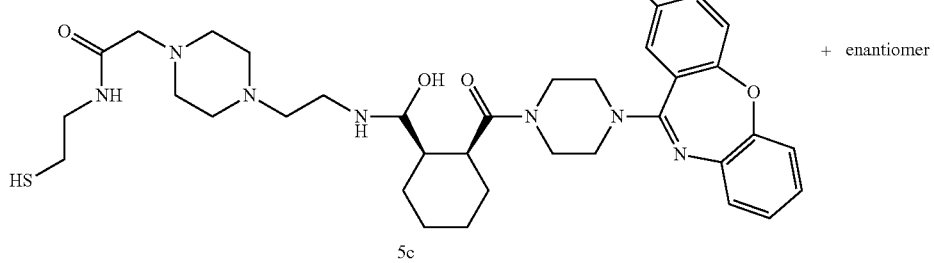

5c 5b (7 mg, 0.010 mmol) was preactivated by incubating with PyBOP (12.5 mg, 0.024 mmol) and DIEA (5 µl, 0.03 mmol) in 200 µl of dry DMF for 45 min at RT. 5a (20 mg, 0.028 mmol) and DIEA (15 µl, 0.09 mmol) were added and mixture was incubated for further 60 min. Mixture was quenched with 0.5 ml of acetonitrile/acetic acid/water (1/1/1) and purified by RP-HPLC. After lyophilization 3 mg (0.0026 mmol, double TFA salt) of 5c were obtained.

MS: m/z 939.3=[M+H]$^+$ (MW calculated=938.6 g/mol).

For trityl deprotection, lyophilisate was incubated in 1 ml HFIP and 3 µl TES for 30 min. Mixture was evaporated and thiol was purified by RP-HPLC. After lyophilization 2 mg (2.2 mmol, double TFA salt) of amoxapine-linker conjugate 5c were obtained.

MS: m/z 697.1=[M+H]$^+$ (MW calculated=696.3 g/mol).

Synthesis of Fatty Acid-PEG-Amoxapine Conjugate
(5)

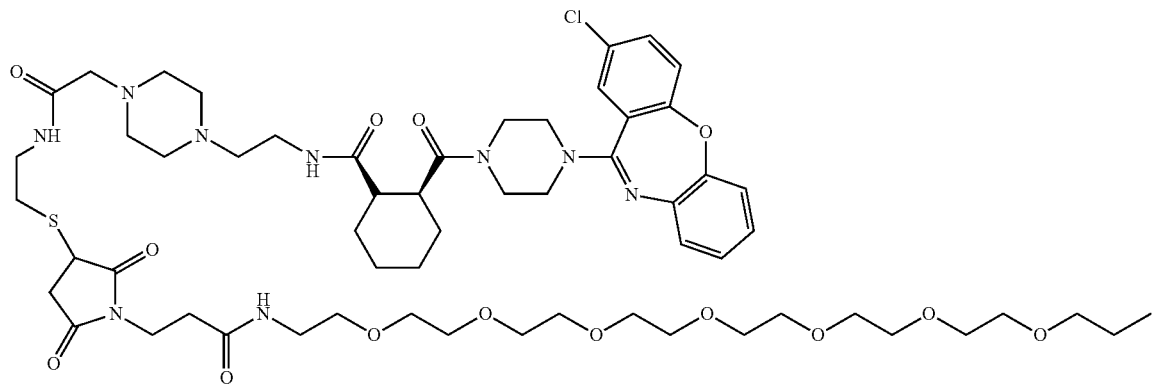

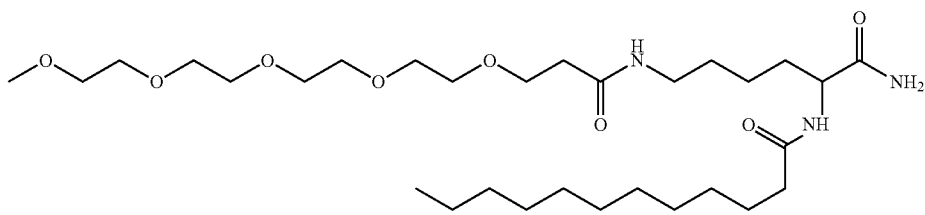

Amoxapine-linker conjugate 5c (2 mg, 2.2 µmol) and 1 (3.5 mg, 3.2 µmol) were dissolved in 900 µl of acetonitrile/water 7/3 (v/v). 60 µl of 0.5 M phosphate buffer (pH 7.4) were added and the mixture was incubated at RT for 10 min. 5 was purified by RP-HPLC.

MS: m/z 1774.9=[M+H]$^+$ (MW calculated=1774.7 g/mol).

Example 6

Synthesis of Linker Reagent (6)

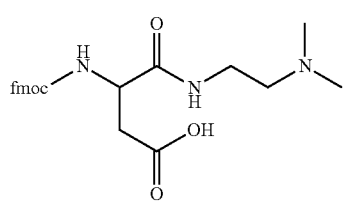

Fmoc-Asp(tBu)-OH (411 mg, 1 mmol), HOBt (153 mg, 1 mmol), and DIC (160 µl, 1 mmol) were dissolved in 2 ml of DMF and incubated for 10 min at RT. N,N-dimethyl ethylenediamine (160 µl, 1.5 mmol) was added and stirred at RT for 30 min. Acetic acid (300 µl) was added and Fmoc-Asp(tBu)-NH—(CH$_2$)$_2$—N(CH$_3$)$_2$ was purified by RP-HPLC.

Yield: 220 mg (0.46 mmol)

MS Fmoc-Asp(tBu)-NH—(CH$_2$)$_2$—N(CH$_3$)$_2$: m/z 504.6=[M+Na]$^+$ (MW calculated=481.6 g/mol).

Fmoc-Asp(tBu)-NH—(CH$_2$)$_2$—N(CH$_3$)$_2$ (220 mg, 0.46 mmol) was dissolved in 3 ml of 98/2 (v/v) TFA/TES. After 30 min the solvent was removed under a nitrogen stream and 6 was purified by RP-HPLC using 0.01% HCl in water as solvent A and 0.01% HCl in acetonitril as solvent B Yield: 146 mg (0.32 mmol, HCl salt)

MS: m/z 426.5=[M+H]$^+$ (MW calculated=425.5 g/mol).

Example 7

Synthesis of Linker Reagents 7a and 7b

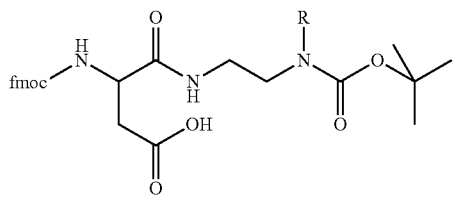

7a: R = H
7b: R = CH₃

Synthesis of 7a:

Fmoc-Asp(tBu)-OH (300 mg, 0.73 mmol), HOBt (1112 mg, 0.73 mmol), and DIC (117 µl, 0.73 mmol) were dissolved in 2 ml of DMF and incubated for 10 min at RT. Boc-ethylenediamine (230 mg, 1.44 mmol) was added and stirred at RT for 30 min. Acetic acid (300 µl) was added and Fmoc-Asp(tBu)-NH—(CH₂)₂—NH-boc was purified by RP-HPLC.

Yield: 205 mg (0.37 mmol)

MS intermediate: m/z 576.6=[M+Na]$^+$ (MW calculated=553.7 g/mol).

Fmoc-Asp(tBu)-NH—(CH₂)₂—NH-boc (205 mg, 0.37 mmol) was dissolved in 3 ml of 98/2 (v/v) TFA/TES. After 30 min the solvent was removed under a nitrogen stream and Fmoc-Asp(H)—NH—(CH₂)₂—NH₂ was purified by RP-HPLC.

Yield: 140 mg (0.27 mmol, TFA salt)

MS intermediate: m/z 398.8=[M+H]$^+$ (MW calculated=397.4 g/mol).

Fmoc-Asp(H)—NH—(CH₂)₂—NH₂ (140 mg, 0.27 mmol, TFA salt) was dissolved in 1 ml of DMF and DIEA (140 µl, 0.81 mmol) and boc₂O (100 mg, 0.46 mmol) added. The solution was stirred at RT for 15 min and then acidified with acetic acid (300 µl). 7a was purified by RP-HPLC.

Yield 7a: 120 mg (0.24 mmol)

MS 7a: m/z 520.5=[M+Na]$^+$ (MW calculated=497.6 g/mol).

7b was synthesized as described above except for the use of H₂N—(CH₂)₂—N(CH₃)-boc instead of boc-ethylenediamine as amine in the first step.

Yield 7b: 115 mg

MS 7b: m/z 534.5=[M+Na]$^+$ (MW calculated=511.6 g/mol).

Example 8

Synthesis of Exendin-Linker Conjugates 8a, 8b and 8c

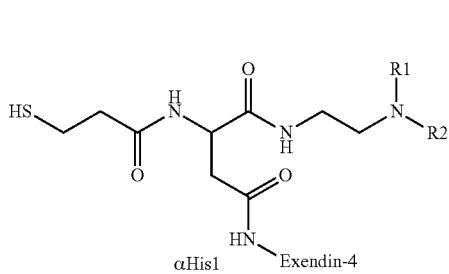

8a: R1 = H, R2 = H
8b: R1 = H, R2 = CH₃
8c: R1 = CH₃, R2 = CH₃

Synthesis of 8a:

7a (30 mg, 60 µmol), HOBt (9 mg, 60 µmol), DIEA (12 µl, 70 µmol), and DIC (10 µl, 63 mmol) were dissolved in 200 µl of DMF and immediately added to side-chain protected Exendin-4 on resin (40 mg, 4 µmol) and incubated for 1 h at room temperature. Resin was washed ten times with DMF and then incubated for 5 min with 500 µl of 1/1/2 acetic anhydride/pyridine/DMF. Resin was washed 10 times with DMF and fmoc group was removed. Trt-mercaptopropionic acid was coupled and 8a was cleaved from resin and purified by RP-HPLC.

Yield: 3.6 mg

MS 8a: m/z 1108.5=[M+4H]$^{4+}$; 1477.8=[M+3H]$^{3+}$ (MW calculated=4432 g/mol).

8b was synthesized as described above for 8a except for the use of 7b instead of 7a.

Yield: 3.5 mg

MS 8b: m/z 1112.5=[M+4H]$^{4+}$; 1482.5=[M+3H]$^{3+}$ (MW calculated=4446 g/mol).

8c was synthesized as described above for 8a except for the use of 6 instead of 7a.

Yield: 3.2 mg

MS 8c: m/z 1116.2=[M+4H]$^{4+}$; 1487.8=[M+3H]$^{3+}$ (MW calculated=4460 g/mol).

Example 9

Synthesis of PEG40 kDa-Linker-Exendin Conjugates 9a, 9b, and 9c

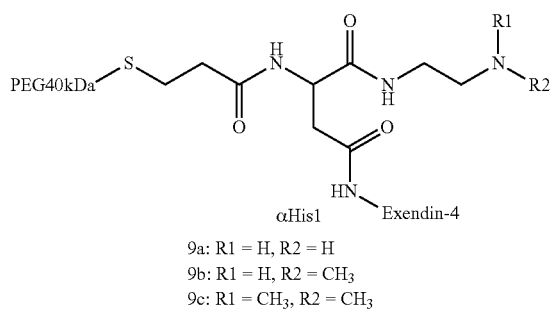

9a: R1 = H, R2 = H
9b: R1 = H, R2 = CH₃
9c: R1 = CH₃, R2 = CH₃

Synthesis of 9a:

8a (3.6 mg) was dissolved in 300 µl 2/1 water/acetonitrile and 50 mg PEG40 kDa-maleimide was added. 100 µl 0.25 M sodium phosphate buffer pH 7 were added and after 5 min the solution was acidified with 50 µl acetic acid.

9a was purified by ion exchange chromatography using 10 mM sodium citrate pH 3 as solvent A and 10 mM sodium citrate pH 3 and 1 M NaCl as solvent B and a step-gradient (0 to 40% B). Fractions containing 9a were desalted and lyophilized:

Yield: 14 mg 9b was synthesized as described above except for the use of 8b.

Yield: 15 mg 9c was synthesized as described above except for the use of 8c.

Yield: 13 mg

Example 10

Synthesis of Fatty Acid-Linker-Exendin Conjugate 10

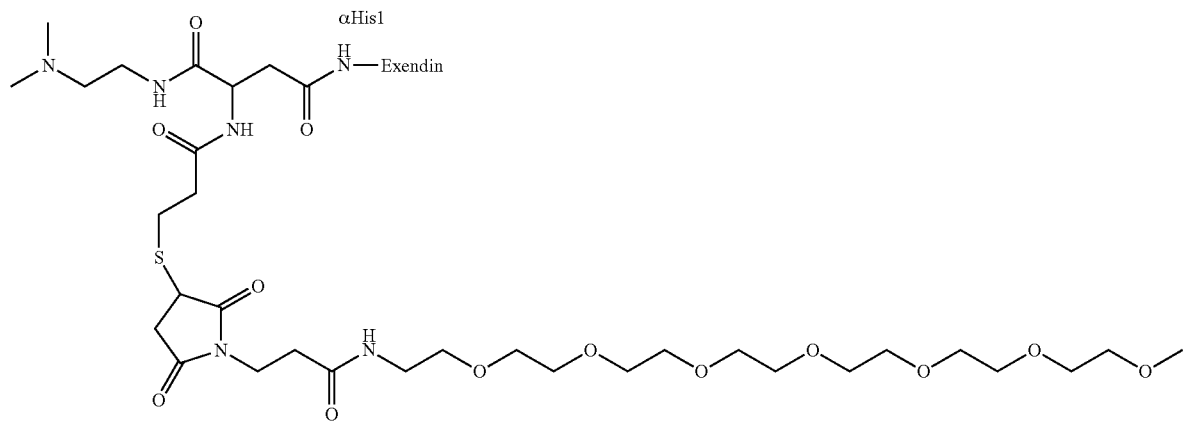

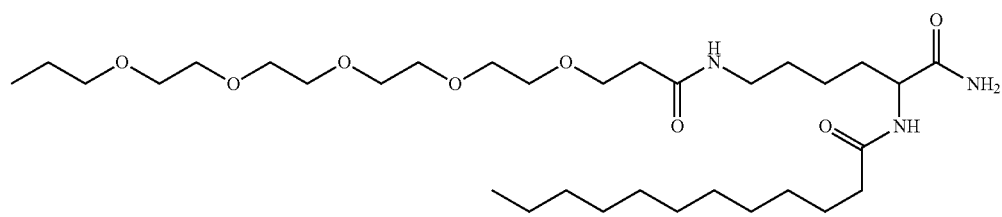

8c (1 mg) was dissolved in 100 µl 1/1 acetonitrile/water and 1 (1 mg) in 100 µl of 3/1 acetonitrile/water was added. 100 µl of 0.25 M sodium phosphate buffer was added, the reaction was stirred for 5 min, after which 10 was purified by RP-HPLC.

Yield: 1.3 mg

MS 10: m/z 1385.9=[M+4H]$^{4+}$; 1846.3=[M+3H]$^{3+}$ (MW calculated=5528.3 g/mol).

Example 11

Synthesis of NHS-Activated Linker Reagent 11

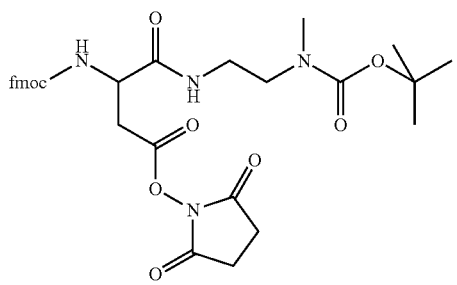

7b (20 mg, 40 µmol), N,N'-dicyclohexylcarbodiimide (10 mg, 48 µmol), and NHS (8 mg, 70 mmol) were dissolved in 300 µl of dry DCM and stirred at RT for 1 h. Solvent was removed under a nitrogen stream and 11 was purified by RP-HPLC and lyophilized.

Yield: 22 mg (36 µmol)

MS: m/z 631.5=[M+Na]$^+$ (MW calculated=608.7 g/mol).

Example 12

Synthesis of Linker-Exendin(Fluorescein) Conjugate (12a) and Linker-GRF(1-29)(Fluorescein) Conjugate (12b)

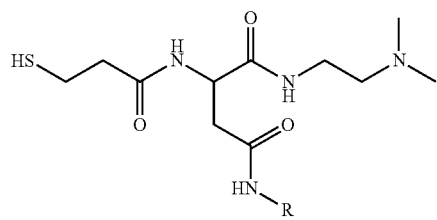

12a: R = Exendin(εK27-fluorescein)
12b: R = GRF(1-29)(εK21-fluorescein)

6 (60 mg, 130 µmol HCl salt), HOBt (20 mg, 130 µmol), DIEA (40 µl, 230 µmol), and DIC (20 µl, 126 µmol) were dissolved in 700 µl of DMF and immediately added to side-chain protected Exendin-4 on resin (120 mg, 12 µmol) and incubated for 1 h at room temperature. Resin was washed ten times with DMF and then incubated for 5 min with 1 ml of 1/1/2 (v/v/v) acetic anhydride/pyridine/DMF. Resin was washed ten times with DMF and fmoc group was removed. Trt-mercaptopropionic acid was coupled according to standard coupling method and resin was washed five times with DMF and ten times with DCM. Mmt protecting group of Lys27 was removed by incubation of resin five times in 2 ml of 9/1 (v/v) DCM/HFIP for 5 min. Resin was washed five times with DCM and five times with DMF and 5,6-carboxy-fluorescein-NHS ester (20 mg, 42 µmol) and DIEA (20 µl, 115 µl) in 300 µl DMF were added to resin and incubated for 30 min. 12a was cleaved from resin and purified by RP-HPLC Yield: 12 mg MS 12a: m/z 1205.9=[M+4H]$^{4+}$; 1607.0=[M+3H]$^{3+}$ (MW calculated=4818.3 g/mol). 12b was synthesized as described for 12a except for the use of GRF(1-29) on resin (120 mg, 12 µmol).

Yield: 11 mg

MS 12b: m/z 998.6=[M+4H]$^{4+}$; 1330.5=[M+3H]$^{3+}$ (MW calculated=3989.6 g/mol).

Synthesis of Mercaptopropionyl-Exendin(Fluorescein) (12c) and Mercaptopropionyl-GRF(1-29)(Fluorescein) (12d)

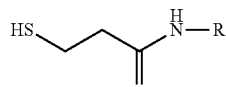

12c: R = Exendin(εK27-fluorescein)
12d: R = GRF(1-29)(εK21-fluorescein)

Trt-mercaptopropionic acid was coupled according to standard coupling method to side-chain protected Exendin-4 on resin (120 mg, 12 µmol). Mmt protecting group removal of Lys27 and 5,6-carboxy-fluorescein-NHS ester coupling was performed as described for 12a. 12c was cleaved from resin and purified by RP-HPLC Yield: 13 mg MS 12c: m/z 1545.6=[M+3H]$^{3+}$ (MW calculated=4633 g/mol). 12d was synthesized as described for 12c except for the use of GRF(1-29) on resin (120 mg, 12 µmol).

Yield: 11 mg

MS 12d: m/z 1269.1=[M+3H]$^{3+}$ (MW calculated=3804.3 g/mol).

Example 13

Synthesis of Reversible PEG40 kDa-Linker-Exendin (Fluorescein) Conjugate (13a) and Reversible PEG40 kDa-Linker-GRF(1-29)(Fluorescein) Conjugate (13b)

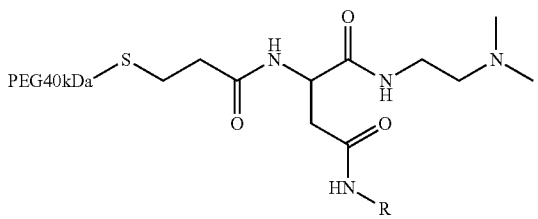

13a: R = Exendin(εK27-fluorescein)
13b: R = GRF(1-29)(εK21-fluorescein)

12a (12 mg) was dissolved in 500 µl of 1/1 acetonitrile/water and 120 mg PEG40 kDa-maleimide in 1 ml of 1/1 acetonitrile/water was added. 300 µl of 0.25 M sodium phosphate buffer pH 7.0 were added and solution was acidified after 10 min with 300 μl acetic acid. 13a was purified by cation exchange chromatography, desalted, and then lyophilized.

Yield: 51 mg 13b was synthesized as described for 13a except for the use of 12b instead of 12a.

Yield: 46 mg

Synthesis of Permanent PEG40 kDa-Exendin(Fluorescein) Conjugate (13c) and Permanent PEG40 kDa-GRF(1-29)(Fluorescein) Conjugate (13d)

PEG40kDa-S-CH2CH2-C(O)-NH-R    13

13c: R = Exendin(εK27-fluorescein)
13d: R = GRF(1-29)(εK21-fluorescein)

13c was synthesized as described for 13a except for the use of 12c instead of 12a.

Yield: 55 mg 13d was synthesized as described for 13a except for the use of 12d instead of 12a.

Yield: 45 mg

Example 14

Synthesis of Linker-GRF(1-29) Conjugate 14

[Structure 14: HS-CH2CH2-C(O)-NH-CH(CH2-C(O)-NH-GRF(1-29) at αTyr1)-C(O)-NH-CH2CH2-N(CH3)2]

14 was synthesized as described for 8c except for the use of side-chain protected GRF(1-29) resin.

Yield: 10 mg

MS 14: m/z 908.2=[M+4H]$^{4+}$; 1211.2=[M+3H]$^{3+}$ (MW calculated=3631.3 g/mol).

Example 15

Synthesis of PEG40 kDa-Linker-GRF(1-29) Conjugate (15)

[Structure 15: PEG40KDa-S-CH2CH2-C(O)-NH-CH(CH2-C(O)-NH-GRF(1-29) at αTyr1)-C(O)-NH-CH2CH2-N(CH3)2]

15 was synthesized as described for 9c except for the use of 14 and 10 mM sodium citrate pH 4 as solvent A and 10 mM sodium citrate pH 4 and 1 M sodium chloride as solvent B for cation exchange chromatography.

Yield: 11 mg

Example 16

Synthesis of Linker Intermediate 16

[Structure 16: (CH3)2N-CH2CH2-NH-Tmob]

N,N-dimethylethylenediamine (198 μL, 1.8 mmol) and NaCNBH$_3$ (58 mg, 0.9 mmol) were dissolved in methanol (5 mL) and brought to pH 5.5 by addition of AcOH (250 μL). A suspension of 2,4,6,-trimethoxybenzaldehyde (294 mg, 1.5 mmol) in EtOH (5 mL) was added and the reaction was stirred at RT for 1 h. 5 N HCl (0.5 mL) was added and the mixture was stirred for further 12 h. The solvent was removed under reduced pressure; the residue was dissolved in sat. NaHCO$_3$ and extracted 3× with DCM. The combined organic phases were dried over NaSO$_4$ and the solvent was evaporated under reduced pressure.

Yield: 303 mg (1.13 mmol)

MS: m/z 269.3=[M+H]$^+$ (MW calculated=268.4 g/mol)

Example 17

Synthesis of Linker 17a and 17b

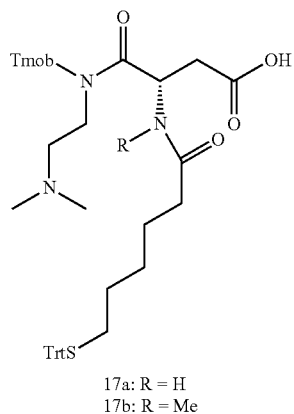

17a: R = H
17b: R = Me

Synthesis of 17a:

Fmoc-Asp(OtBu)-OH (322 mg, 0.78 mmol), Tmob-protected diamine 16 (150 mg, 0.56 mmol), HATU (255 mg, 0.67 mmol) and DIEA (290 µL, 1.68 mmol) were dissolved in DMF (1.5 mL). The mixture was stirred for 30 min, acidified with AcOH and purified by RP-HPLC.

Yield: 463 mg (5.97 mmol, TFA salt, ca. 90% pure)

MS Fmoc-Asp(OtBu)-N(TMOB)$CH_2CH_2N(CH_3)_2$: m/z 662.5=$[M+H]^+$ (MW calculated=661.8 g/mol)

Fmoc-Asp(OtBu)-N(Tmob)$CH_2CH_2N(CH_3)_2$ (225 mg, 0.29 mmol) was dissolved in a solution of piperidine (50 µL) and DBU (15 µL) in DMF (1.5 mL). The mixture was stirred at RT for 1.5 h. AcOH was added and H-Asp(OtBu)-N(TMOB)$CH_2CH_2N(CH_3)_2$ was purified by RP-HPLC.

Yield: 114 mg (0.21 mmol, TFA salt)

MS H-Asp(OtBu)-N(Tmob)$CH_2CH_2N(CH_3)_2$: m/z 462.4=$[M+Na]^+$ (MW calculated=439.6 g/mol)

The TFA salt of H-Asp(OtBu)-N(Tmob)$CH_2CH_2N(CH_3)_2$ (114 mg, 0.21 mmol) was dissolved in sat. $NaHCO_3$ (10 mL) and extracted 3× with DCM (3×10 mL). The combined organic layers were dried over $NaSO_4$ and the solvent was removed under reduced pressure. The residue was dissolved in DMF (1.0 mL), 6-tritylmercaptohexanoic acid (121 mg, 0.31 mmol), HATU (118 mg, 0.31 mmol) and DIEA (108 µL, 0.62 mmol) were added. The mixture was stirred for 30 min. AcOH was added (200 µL) and TrtS$(CH_2)_5$CONH-Asp(OtBu)—N(Tmob)$CH_2CH_2N(CH_3)_2$ was purified by RP-HPLC.

Yield: 95 mg (0.10 mmol, TFA salt)

MS TrtS$(CH_2)_5$CONH-Asp(OtBu)-N(Tmob)$CH_2CH_2N(CH_3)_2$: m/z 812.64=$[M+H]^+$ (MW calculated=812.1 g/mol)

TrtS$(CH_2)_5$CONH-Asp(OtBu)-N(Tmob)$CH_2CH_2N(CH_3)_2$ (95 mg, 0.10 mmol) was dissolved in a 3:1 mixture of MeOH/$H_2O$ (1.0 mL), LiOH (7.4 mg, 0.31 mmol) was added and the mixture was stirred for 5 h at 60° C. AcOH was added (100 µL) and 17a was purified by RP-HPLC.

Yield: 64 mg (0.07 mmol, TFA salt)

MS 17a: m/z 756.5=$[M+H]^+$ (MW calculated=756.0 g/mol)

17b was synthesized as described above except for the use of Fmoc-NMe-Asp(OtBu)-OH instead of Fmoc-Asp(OtBu)-OH in the first step.

Yield 17b: 16 mg (18 µmol, TFA salt)

MS 17b: m/z 770.5=$[M+H]^+$ (MW calculated=770.0 g/mol)

Example 18

Synthesis of Linker-BNP Conjugates 18a and 18b

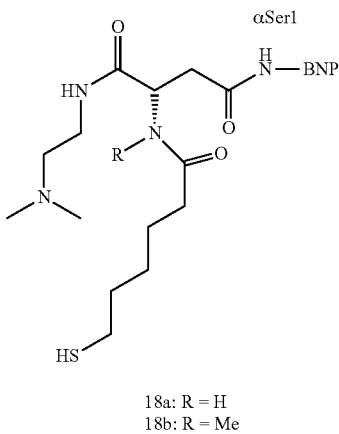

18a: R = H
18b: R = Me

Synthesis of 18a:

17a (8.0 mg, 0.01 mmol), PyBOP (5.2 mg, 10 µmol) and DIEA (7 µL, 40 µmol) were dissolved in DMF (400 µL) and immediately added to resin bound, side chain protected BNP-32a (50 mg, 5 µmol). After incubation for 2 h at RT, the resin was washed with 10×DMF, 10×DCM and dried in vacuo. The product was cleaved from the resin and purified by RP-HPLC.

Yield: 10.6 mg

MS 18a: m/z 930.4=$[M+4H]^{4+}$; 1240.1=$[M+3H]^{3+}$ (MW calculated=3717.2 g/mol)

18b was synthesized as described above except for the use of 17b instead of 17a.

Yield: 4.7 mg

MS 18b: m/z 933.9=$[M+4H]^{4+}$; 1244.7=$[M+3H]^{3+}$ (MW calculated=3731.0 g/mol)

Example 19

Synthesis of PEG40 kDa-linker-BNP conjugates 19a and 19b

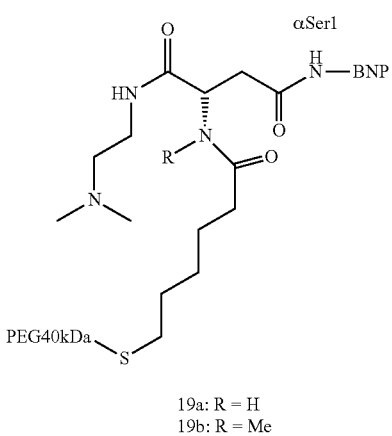

19a: R = H
19b: R = Me 18a (5.2 mg) was dissolved in 1:1 H₂O/acetonitrile containing 0.1% TFA (200 µL). A solution of PEG40 kDa-maleimide (70 mg) in 1:1 H₂O/acetonitrile (1.5 mL) and phosphate buffer (30 µL, pH 7.4, 0.5 M) was added. The solution was incubated at RT, after 5 min AcOH (30 µL) was added. 19a was purified by cation exchange chromatography, desalted, and lyophilized.

Yield: 19.2 mg 19b was synthesized as described for 19a except for the use of 18b instead of 18a.

Example 20

Synthesis of Linker 20

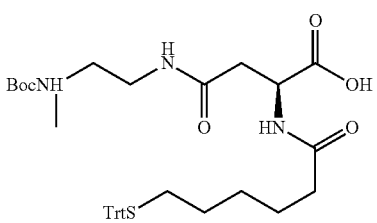

Fmoc-Asp(OH)OtBu (100 mg, 0.24 mmol), H₂N—(CH₂)₂—N(CH₃)-boc (36 µL, 0.20 mmol), HATU (92 mg, 0.24 mmol) and DIEA (105 µL, 0.60 mmol) were dissolved in 1 mL DMF. The mixture was stirred for 1 h at RT, acidified with AcOH (100 µL) and purified by HPLC.

Yield: 91 mg (0.13 mmol)

MS Fmoc-Asp(NH(CH₂)₂N(CH₃)-boc)OtBu: 590.3=[M+Na]⁺ (MW calculated=567.7 g/mol)

Fmoc-Asp(NH(CH₂)₂N(CH₃)-boc)OtBu (91 mg, 0.13 mmol) was dissolved in DMF (1.0 mL), piperidine (50 µL) and DBU (15 µL) were added and the mixture was stirred for 45 min at RT. AcOH (100 µL) was added and NH₂-Asp(NH(CH₂)₂N(CH₃)-boc)OtBu was purified by RP-HPLC.

Yield: 39 mg (0.09 mmol, TFA salt)

MS NH₂-Asp(NH(CH₂)₂N(CH₃)-boc)OtBu: m/z 368.1=[M+Na]⁺ (MW calculated=345.4 g/mol)

NH₂-Asp(NH(CH₂)₂N(CH₃)-boc)OtBu (36 mg, 0.09 mmol) was dissolved in DMF (0.5 mL), 6-tritylmercaptohexanoic acid (55 mg, 0.14 mmol), HATU (53 mg, 0.14 mmol) and DIEA (49 µL, 0.28 mmol) were added. The mixture was stirred for 45 min. AcOH was added (100 µL) and TrtS(CH₂)₅CONH-Asp(NH(CH₂)₂N(CH₃)-boc)OtBu was purified by RP-HPLC.

Yield: 41 mg (0.06 mmol)

MS TrtS(CH₂)₅CONH-Asp(NH(CH₂)₂N(CH₃)-boc)OtBu: m/z 740.6=[M+Na]⁺ (MW calculated=718.0 g/mol)

TrtS(CH₂)₅CONH-Asp(NH(CH₂)₂N(CH₃)-boc)OtBu (41 mg, 0.06 mmol) was dissolved in 1:1 dioxane/H₂O (1.0 mL), LiOH (4.1 mg, 0.17 mmol) was added and the mixture was stirred at 60° C. for 1 h. AcOH (50 µL) was added and 20 was purified by RP-HPLC.

Yield: 31 mg (0.05 mmol)

MS 20: m/z 684.5=[M+Na]⁺ (MW calculated=661.9 g/mol)

Example 21

Synthesis of Linker-Exendin Conjugate 21

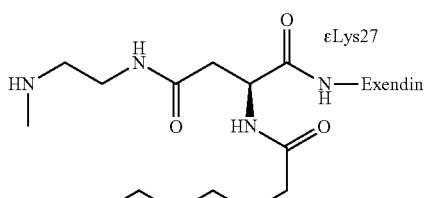

Resin bound, side chain protected exendin (50 mg, 5 µmol) with a Mmt protecting-group on Lys27 was first boc-protected at the N-terminus (see Materials and Methods) and then incubated five times (5 min) with 2 mL of 9/1 (v/v) DCM/HFIP to remove the Mmt protecting group from Lys27. 20 (6.6 mg, 10 µmol), PyBOP (5.2 mg, 10 µmol) and DIEA (7 µL, 40 µmol) were dissolved in DMF (400 µL) and immediately added to the resin. Incubation for 3 h at RT, the resin was washed with 10×DMF, 10×DCM and dried in vacuo. The product was cleaved from the resin and purified by RP-HPLC.

Yield: 2.4 mg

MS 21: m/z 1497.2=[M+3H]³⁺ (MW calculated=4488.0 g/mol)

Example 22

Synthesis of Fatty Acid-Linker-Exendin Conjugate 22

21 (2.6 mg) was dissolved in 200 µl 1/1 acetonitrile/water and 1 (0.8 mg) in 400 µl of 7/3 acetonitrile/water was added. 100 µl of 0.25 M sodium phosphate buffer was added, the reaction was stirred for 5 min after which 22 was purified by RP-HPLC.

Yield: 2.4 mg

MS 22: m/z 1388.3=[M+4H]$^{4+}$; 1857.1=[M+3H]$^{3+}$ (MW calculated=5566.4 g/mol).

Example 23

Synthesis of Precursor 23

6-Tritylmercaptohexanoic acid (200 mg, 0.51 mmol), (PfpO)$_2$C0 (202 mg, 0.51 mmol) and collidine (340 µL, 2.65 mmol) were dissolved in DMSO (1 mL) and stirred for 30 min at RT. The mixture was added to a solution of Fmoc-Lys-OH (170 mg, 0.46 mmol) in H$_2$O/pyridine/tBuOH (3:3:1, 6 mL). The reaction was heated at 60° C. for 2 h, diluted with EtOAc, extracted 2× with 0.1M H$_2$SO$_4$, 2× with brine and dried over Na$_2$SO$_4$. The solvent was evaporated under reduced pressure and the residue was purified by RP-HPLC.

Yield: 109 mg

MS 23: m/z 741.3 [M+H]$^+$ (MW calculated=741.0 g/mol)

Example 24

Synthesis of Linker 24a-24c

24a: R1 = H, R2 = boc
24b: R1 = Me, R2 = boc
24c: R1 = R2 = Me 23 (186 mg, 0.25 mmol) and DIEA (160 µL, 0.92 mmol) were dissolved in DCM (2 mL), added to 2-chlorotrityl chloride resin (312 mg, 1.3 mmol/g) and agitated for 45 min at RT. MeOH (0.6 mL) was added and the resin was incubated for another 15 min. The resin was washed with DCM (10×) and DMF (10×). Fmoc-deprotection and urea formation was achieved according to general procedures (see Materials and Methods) by reaction with N-boc-ethylenediamine (57 µL, 0.34 mmol), the product was cleaved from the resin and purified by RP-HPLC.

Yield: 14 mg

MS 24a: m/z 705.4 [M+H]$^+$, 727.3 [M+Na]$^+$ (MW calculated=704.9 g/mol)

24b was synthesized as described for 24a except for the use of N-boc-N-methylethylenediamine instead of instead of N-boc-ethylenediamine.

Yield: 21 mg

MS 24b: m/z 719.3 [M+H]$^+$, 741.4 [M+Na]$^+$ (MW calculated=719.0 g/mol)

24c was synthesized as described for 24a except for the use of N,N-dimethylethylenediamine instead of N-boc-ethylenediamine.

Yield: 10 mg

MS 24c: m/z 633.2 [M+H]$^+$ (MW calculated=632.9 g/mol)

Example 25

Synthesis of Exendin-Linker Conjugates 25a-25c

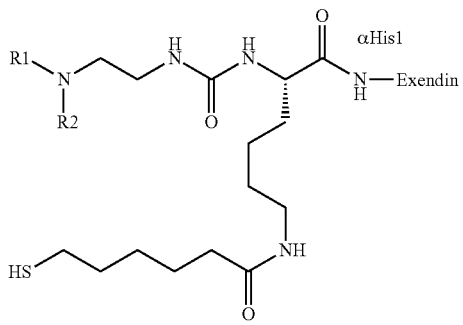

25a: R1 = R2 = H
25b: R1 = Me, R2 = H
25c: R1 = R2 = Me 24a (7.0 mg, 0.01 mmol), PyBOP (5.2 mg, 10 µmol) and DIEA (7 µL, 40 µmol) were dissolved in DMF (250 µL), immediately added to resin bound, side chain protected exendin (50 mg, 5 µmol) and incubated for 2 h at RT. The resin was washed with DMF (10×), DCM (10×) and dried in vacuo. The product was cleaved from the resin and purified by RP-HPLC.

Yield: 1.6 mg
MS 25a: m/z 1511.8=$[M+3H]^{3+}$ (MW calculated=4530.8 g/mol)

25b was synthesized as described for 25a except for the use of 24b instead of 24a.
Yield: 4.3 mg
MS 25b: m/z 1516.3=$[M+3H]^{3+}$ (MW calculated=4544.8 g/mol)

25c was synthesized as described for 25a except for the use of 24c instead of 24a.
Yield: 1.3 mg
MS 25c: m/z 1520.4=$[M+3H]^{3+}$ (MW calculated=4558.8 g/mol)

Example 26

Synthesis of Fatty Acid-Linker Conjugates 26a-26c 25a (1.6 mg) was dissolved in 200 µl 1/1 acetonitrile/water and 1 (0.11 mg) in 200 µl of 7/3 acetonitrile/water was added. 30 µl of 0.25 M sodium phosphate buffer was added, the reaction was stirred for 5 min, after which 26a was purified by RP-HPLC.

MS 26a: m/z 1870.0=$[M+3H]^{3+}$ (MW calculated=5609.2 g/mol).

26b was synthesized as described for 26a except for the use of 25b instead of 25a.
MS 26b: m/z 1875.9=$[M+3H]^{3+}$, 1406.7=$[M+4H]^{4+}$ (MW calculated=5623.2 g/mol)

26c was synthesized as described for 26a except for the use of 25c instead of 25a.
MS 26c: m/z 1879.4=$[M+3H]^{3+}$, 1410.5=$[M+4H]^{4+}$ (MW calculated=5637.2 g/mol)

Example 27

Synthesis of 20 KDa-PEG-Linker-Exendin Conjugates 27a-27c

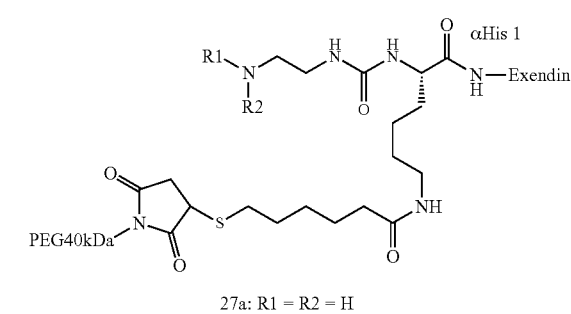

27a: R1 = R2 = H
27b: R1 = Me, R2 = H
27c: R1 = R2 = Me 25a (2.0 mg) was dissolved in 1:1 $H_2O$/MeCN containing 0.1% TFA (200 µl). A solution of PEG40 KDa-maleimide (18 mg) in 1:1 $H_2O$/MeCN (1 ml) and phosphate buffer (15 µl, pH 7.4, 0.5 M) was added. The solution was incubated at RT, after 5 min AcOH (20 µl) was added and 27a was purified by cation exchange chromatography, desalted and lyophilized.

27b was synthesized as described for 27a except for the use of 25b instead of 25a.

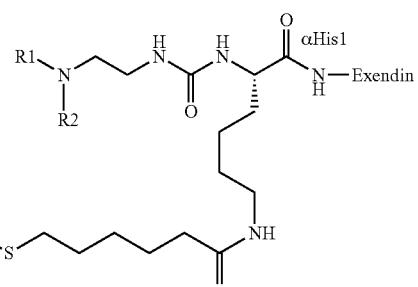

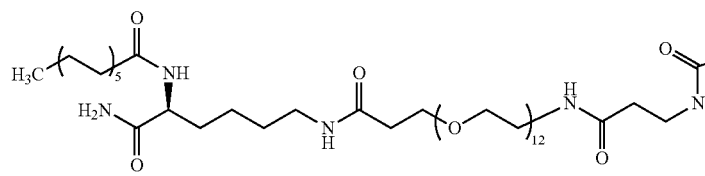

26a: R1 = R2 = H
26b: R1 = Me, R2 = H
26c: R1 = R2 = Me 27c was synthesized as described for 27a except for the use of 25c instead of 25a.

Example 28

Synthesis of Linker 28

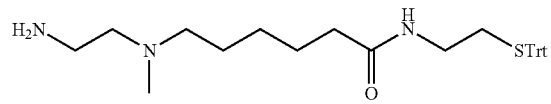

6-Bromohexanoyl chloride (46 µl, 0.31 mmol) was dissolved in 0.2 ml $CH_2Cl_2$ and added to a solution of $H_2N$—$CH_2$—$CH_2$-STrt (100 mg, 0.28 mmol), DIEA (97 µl, 0.56 mmol) in $CH_2Cl_2$ (0.8 ml). The mixture was stirred for 2 h at RT. The reaction mixture was acidified with AcOH (50 µl) and the solvent was removed in vacuo. The residue was purified on silica gel (heptane/EtOAc=1:1) to obtain Br—$(CH_2)_5$—CONH—$(CH_2)_2$-STrt.

Yield: 137 mg (0.276 mmol, 98%)

MS Br—$(CH_2)_5$—CONH—$(CH_2)_2$-STrt: 518.9=$[M+Na]^+$, (MW calculated=496.5 g/mol)

N-Boc-ethylenediamine (81 µl, 0.51 mmol) was added to a solution of Br—$(CH_2)_5$—CONH—$(CH_2)_2$-STrt (230 mg, 0.46 mmol) and $Na_2CO_3$ (196 mg, 1.85 mmol) in DMF (0.8 ml). The reaction mixture was stirred for 10 h at 70° C. After cooling to RT the mixture was diluted with 4 ml (MeCN/$H_2O$=25:75, with 0.1% TFA) and purified by RP-HPLC to get Boc-NH—$(CH_2)_2$—NH—$(CH_2)_5$—CONH—$(CH_2)_2$-STrt.

Yield: 189 mg (0.27 mmol, 59%, TFA-salt)

MS Boc-NH—$(CH_2)_2$—NH—$(CH_2)_5$—CONH—$(CH_2)_2$-STrt: 576.5=$[M+H]^+$, (MW calculated=575.5 g/mol)

Boc-NH—$(CH_2)_2$—NH—$(CH_2)_5$—CONH—$(CH_2)_2$-STrt (189 mg, 0.27 mmol) and HCHO (35% aqueous, 113 µl) were dissolved in MeCN (1.5 ml) and $NaCNBH_3$ (34 mg, 0.54 mmol) was added. The reaction mixture was stirred for 5 h at RT. After completion of the reaction (MS) the solution was diluted with $H_2O$ (5 ml) and extracted with $CH_2Cl_2$ (3×5 ml). The combined organic layers were dried over $MgSO_4$, filtered and the solvent was removed in vacuo. The residue was purified by RP-HPLC to get Boc-NH—$(CH_2)_2$—N($CH_3$)—$(CH_2)_5$—CONH—$(CH_2)_2$-STrt.

Yield: 62.8 mg (0.11 mmol, 39%)

MS Boc-NH—$(CH_2)_2$—N($CH_3$)—$(CH_2)_5$—CONH—$(CH_2)_2$-STrt: 590.6=$[M+H]^+$, (MW calculated=589.0 g/mol)

Boc-NH—$(CH_2)_2$—N($CH_3$)—$(CH_2)_5$—CONH—$(CH_2)_2$-STrt (62.8 mg, 0.11 mmol) was dissolved in THF (6 ml) and HCl in dioxane (130 µl, 4 M solution) was added. The reaction mixture was stirred for 12 h at RT. 200 µl HCl in dioxane was added and the solvent was removed in vacuo. The residue was purified by RP-HPLC to give $H_2N$—$(CH_2)_2$—N($CH_3$)—$(CH_2)_5$—CONH—$(CH_2)_2$-STrt and not consumed starting material Boc-NH—$(CH_2)_2$—N($CH_3$)—$(CH_2)_5$—CONH—$(CH_2)_2$-STrt.

Yield: 32.8 mg (0.062 mmol, 44%, HCl-salt) 28 and 14.7 mg (0.025 mmol, 23%, TFA-salt) starting material MS 28: 490.5=$[M+H]^+$, (MW calculated=489.0 g/mol)

Example 29

General Procedure for the Synthesis Carboxylic Acid Substituted BNP Precursors 29a and 29b

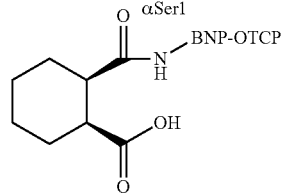

Cis-cyclohexane-1,2-dicarboxylic anhydride (231 mg, 1.5 mmol) and pyridine (271 µl, 2 mmol) were dissolved in DCM (2 ml) and added to resin bound, side chain protected BNP-32a (300 mg). Incubation for 1 h at RT, washed with 10×DCM and dried in vacuo.

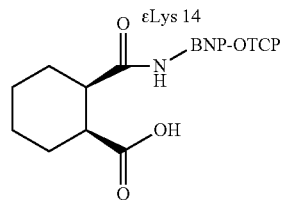

Resin bound, side chain protected BNP-32b, carrying an ivDde protecting group at Lys14, was first boc-protected at the N-terminus, deprotected at Lys14 position (see Materials and Methods) and then reacted with cis-cyclohexane-1,2-dicarboxylic anhydride as described above for 29a.

Example 30

Synthesis of BNP-Linker-Thiols 30a and 30b

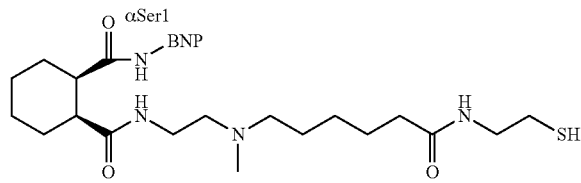

$H_2N$—$(CH_2)_2$—N($CH_3$)—$(CH_2)_5$—CONH—$(CH_2)_2$-STrt 28 (5.2 mg, 0.01 mmol), PyBOP (5.2 mg, 0.01 mmol) and DIEA (7.0 µl, 0.04 mmol) were dissolved in DMF (300 µl) and added to resin bound, side chain protected BNP 29a (50 mg, 0.005 mmol). Incubation for 2 h at RT, the resin was washed with DMF (10×), DCM (10×) and dried in vacuo. The product was cleaved from the resin and purified by RP-HPLC.

Yield: 9.8 mg

MS 30a: m/z 947.6=$[M+4H]^{4+}$, 1263.1=$[M+3H]^{3+}$ (MW calculated=3786.3 g/mol)

55

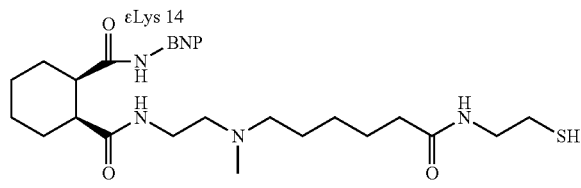

30b 30b was synthesized as described above except for the use of resin bound BNP derivative 29b instead of 29a.

Yield: 7.4 mg

MS 30b: m/z 947.5=[M+4H]$^{4+}$, 1263.0=[M+3H]$^{3+}$ (MW calculated=3786.3 g/mol)

Example 31

Synthesis of 40 KDa-PEG-Linker-BNP Conjugates 31a and 31b

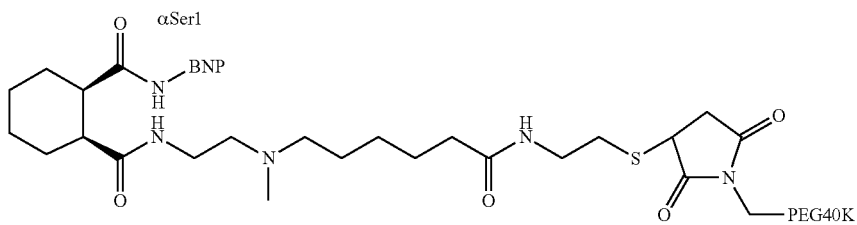

31a 30a (4 mg) was dissolved in 1:1 H$_2$O/MeCN containing 0.1% TFA (200 µl). A solution of PEG40 KDa-maleimide (42.2 mg) in 1:1 H$_2$O/MeCN (1 ml) and phosphate buffer (15 µl, pH 7.4, 0.5 M) was added. The solution was incubated at RT, after 5 min AcOH (20 µl) was added and 31a was purified by cation exchange chromatography, desalted and lyophilized.

Yield: 2.0 mg

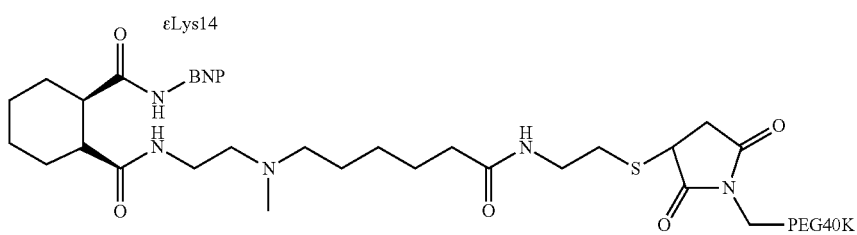

31b 31b was synthesized as described for 31a except for the use of 30b instead of 30a.

Yield: 16.8 mg

56

Example 32

Synthesis of Linker 32

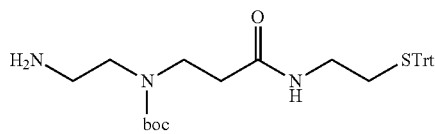

32

3-Bromopropionylchloride (62.5 µl, 0.62 mmol) was dissolved in 0.5 ml CH$_2$Cl$_2$ and added to a solution of H$_2$N—CH$_2$—CH$_2$-STrt (200 mg, 0.56 mmol), DIEA (196 µl, 1.1 mmol) in CH$_2$Cl$_2$ (1 ml). The mixture was stirred for 1 h at RT. The reaction mixture was acidified with AcOH (100 µl) and the solvent was removed in vacuo. The residue was purified over silica gel (heptane/EtOAc=1:1) to obtain Br—(CH$_2$)$_2$CONH—(CH$_2$)$_2$-STrt.

Yield: 223 mg (0.49 mmol, 87%)

MS Br—(CH$_2$)$_2$CONH—(CH$_2$)$_2$-STrt: 478.7=[M+Na]$^+$, (MW calculated=454.7 g/mol)

N-Alloc-ethylenediamine HCl-salt (43.5 mg, 0.24 mmol) and DIEA (38 µl, 0.22 mmol) were added to a solution of Br—(CH$_2$)$_2$CONH—(CH$_2$)-STrt (100 mg, 0.22 mmol) and Na$_2$CO$_3$ (93 mg, 0.87 mmol) in DMF (1 ml). The reaction mixture was stirred for 10 h at 70° C. After cooling down to RT the reaction mixture was diluted with 4 ml (MeCN/

H₂O=25:75, with 0.1% TFA) and purified by HPLC to get Alloc-NH—(CH₂)₂—NH—(CH₂)₂—CONH—(CH₂)₂-STrt.

Yield: 61 mg (0.096 mmol, 44%, TFA salt)

MS Alloc-NH—(CH₂)₂—NH—(CH₂)₂—CONH—(CH₂)₂-STrt: 540.8=[M+Na]⁺, (MW calculated=517.8. g/mol)

Alloc-NH—(CH₂)₂—NH—(CH₂)₂—CONH—(CH₂)₂-STrt (60.9 mg, 0.096 mmol) was dissolved in CH₂Cl₂ and Boc₂O (42 mg, 0.19 mmol) was added. The solution was stirred for 20 h at RT. After completion the reaction was quenched by addition of 70 µl AcOH and the solvent was removed in vacuo. The residue was diluted with 4 ml MeCN/H₂O (25:75, with 0.1% TFA) and purified by RP-HPLC to give Alloc-NH—(CH₂)₂—N(Boc)-(CH₂)₂—CONH—(CH₂)₂-STrt.

Yield: 53.3 mg (0.086 mmol, 89%)

MS Alloc-NH—(CH₂)₂—N(Boc)-(CH₂)₂—CONH—(CH₂)₂-STrt: 640.6=[M+Na]⁺, (MW calculated=617.9. g/mol)

Alloc-NH—(CH₂)₂—N(Boc)-(CH₂)₂—CONH—(CH₂)₂-STrt (48.3 mg, 0.078 mmol) was dissolved in THF, triethylammoniumformate (62 µl) and Pd(PPh₃)₄ (16 mg) were added. The solution was stirred for 12 h at RT and monitored by MS. After completion the solvent was removed in vacuo. The residue was dissolved in MeCN/H₂O (50:50, with 0.1% TFA) and purified by RP-HPLC to give H₂N—(CH₂)₂—N(Boc)-(CH₂)₂—CONH—(CH₂)₂-STrt (31).

Yield: 20.1 mg (0.031 mmol, 40%, TFA-salt)

MS 31: 534.6=[M+H]⁺, 556.6=[M+Na]⁺, (MW calculated=533.5 g/mol)

Example 33

Synthesis of BNP-Linker-Thiols 33a and 33b

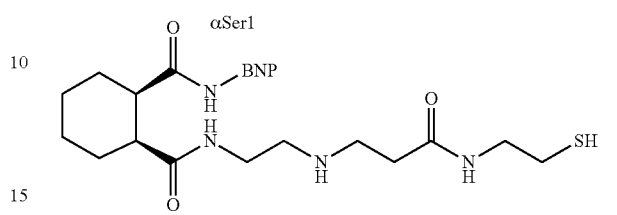

33a 33a was synthesized as described for 30a except for the use of 32 instead of 28.

Yield: 8.0 mg

MS 33a: m/z 933.5=[M+4H]⁴⁺, 1244.3=[M+3H]³⁺ (MW calculated=3729.9 g/mol)

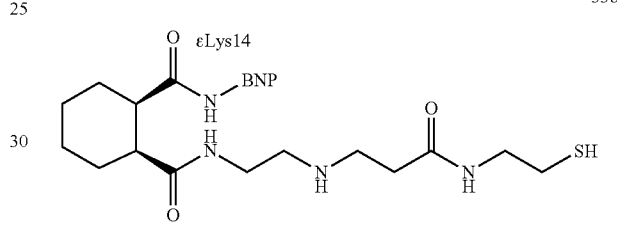

33b 33b was synthesized as described for 30b except for the use of 32 instead of 28.

Yield: 5.0 mg

MS 33b: m/z 933.5=[M+4H]⁴⁺, 1244.3=[M+3H]³⁺ (MW calculated=3715.9 g/mol)

Example 34

Synthesis of 40 KDa-PEG-Linker-BNP Conjugates 34a and 34b

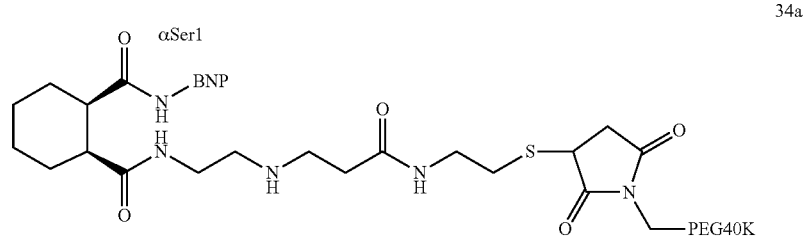

34a 33a (4.3 mg) was dissolved in 1:1 H₂O/MeCN containing 0.1% TFA (200 µl). A solution of PEG40 KDa-maleimide (46.8 mg) in 1:1 H₂O/MeCN (1 ml) and phosphate buffer (20 µl, pH 7.4, 0.5 M) was added. The solution was incubated at RT, after 5 min AcOH (20 µl) was added and 34a was purified by cation exchange chromatography, desalted and lyophilized.

Yield: 9.7 mg

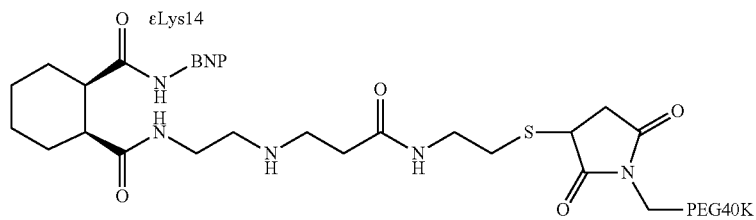

34b was synthesized as described for 34a except for the use of 33b instead of 33a.

Yield: 11.5 mg

Example 35

Synthesis of Linker 35

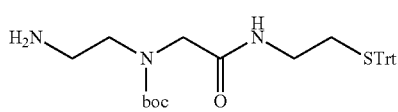

Bromoacetylbromide (54 µl, 0.62 mmol) was dissolved in 0.5 ml $CH_2Cl_2$ and added to a solution of $H_2N$—$CH_2$—$CH_2$-STrt (200 mg, 0.56 mmol) and DIEA (196 µl, 1.1 mmol) in $CH_2Cl_2$ (1 ml). The mixture was stirred for 1 h at RT. The reaction mixture was acidified with AcOH (100 µl) and the solvent was removed in vacuo. The residue was purified over silica gel (heptane/EtOAc=1:1) to obtain product Br—$CH_2$—CONH—$(CH_2)_2$-STrt.

Yield: 245 mg (0.55 mmol, 99%)

MS Br—$CH_2$—CONH—$(CH_2)_2$-STrt: 462.4=$[M+Na]^+$, (MW calculated=440.4 g/mol)

N-Alloc-ethylenediamine HCl-salt (45 mg, 0.25 mmol) and DIEA (79 µl, 0.45 mmol) was added to a solution of Br—$CH_2$—CONH—$(CH_2)_2$-STrt (100 mg, 0.23 mmol) in DMF (1 ml). The reaction mixture was stirred for 10 h at 70° C. After cooling down to RT the reaction mixture was diluted with $H_2O/Et_2O$ (1:1, 40 ml) and the layers were separated. The aqueous layer was extracted several times with $Et_2O$. The combined organic layers were dried with $MgSO_4$, filtered and the solvent was removed in vacuo. The residue was purified over silica gel (DCM/MeOH=95:5) to give Alloc-NH—$(CH_2)_2$—NH—$CH_2$—CONH—$(CH_2)_2$-STrt.

Yield: 94 mg (0.186 mmol, 82%, contains residual DMF)

MS Alloc-NH—$(CH_2)_2$—NH—$CH_2$—CONH—$(CH_2)_2$-STrt: 526.8=$[M+Na]^+$, (MW calculated=503.8. g/mol)

Alloc-NH—$(CH_2)_2$—NH—$CH_2$—CONH—$(CH_2)_2$-STrt (94 mg, 0.186 mmol, with DMF)) was dissolved in $CH_2Cl_2$ and $Boc_2O$ (81 mg, 0.37 mmol) was added. The solution was stirred for 20 h at RT. After completion the reaction was quenched by addition of 100 µl AcOH and the solvent was removed in vacuo. The residue was diluted with 4 ml MeCN/$H_2O$ (25:75, with 0.1% TFA) and purified by RP-HPLC to give Alloc-NH—$(CH_2)_2$—N(Boc)-$CH_2$—CONH—$(CH_2)_2$-STrt.

Yield: 34.7 mg (0.057 mmol, 26%)

MS Alloc-NH—$(CH_2)_2$—N(Boc)-$CH_2$—CONH—$(CH_2)_2$-STrt: 603.9=$[M+Na]^+$, (MW calculated=603.9. g/mol)

Alloc-NH—$(CH_2)_2$—N(Boc)-$CH_2$—CONH—$(CH_2)_2$-STrt (34.7 mg, 0.048 mmol) was dissolved in THF, triethylammoniumformate (38 µl) and $Pd(PPh_3)_4$ (5 mg) were added. The solution was stirred for 12 h at RT and monitored by MS. After completion the solvent was removed in vacuo. The residue was dissolved in MeCN/$H_2O$ (50:50, with 0.1% TFA) and purified by RP-HPLC to give $H_2N$—$(CH_2)_2$—N(Boc)-$CH_2$—CONH—$(CH_2)_2$-STrt 35.

Yield: 12.6 mg (0.019 mmol, 42%, TFA-salt)

MS 35: 520.1=$[M+H]^+$, 542.2=$[M+Na]^+$, (MW calculated=519.2 g/mol)

Example 36

Synthesis of BNP-Linker-Thiols 36a and 36b

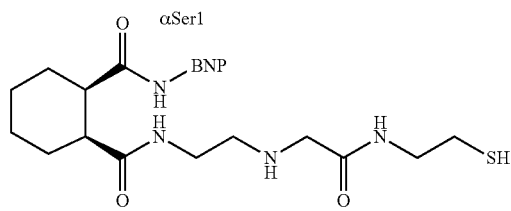

36a was synthesized as described for 30a except for the use of 35 instead of 28.

Yield: 9.1 mg

MS 36a: m/z 930.0=$[M+4H]^{4+}$, 1239.6=$[M+3H]^{3+}$ (MW calculated=3715.9 g/mol)

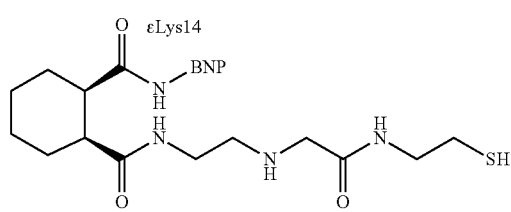

36b was synthesized as described for 30b except for the use of 35 instead of 28.

Yield: 8.0 mg

MS 36b: m/z 929.9=$[M+4H]^{4+}$, 1239.5=$[M+3H]^{3+}$ (MW calculated=3715.9 g/mol)

Example 37

Synthesis of 40 KDa-PEG-Linker-BNP Conjugates 37a and 37b

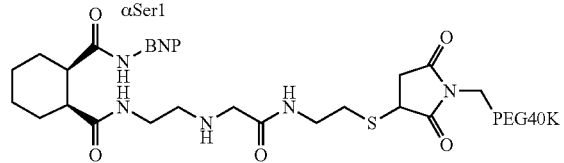

37a 36a (4.2 mg) was dissolved in 1:1 H₂O/MeCN containing 0.1% TFA (200 µl). A solution of PEG40 KDa-maleimide (68 mg) in 1:1 H₂O/MeCN (1 ml) and phosphate buffer (20 µl, pH 7.4, 0.5 M) was added. The solution was incubated at RT, after 5 min AcOH (20 µl) was added and 37a was purified by ion exchange chromatography, desalted and lyophilized.

Yield: 16 mg

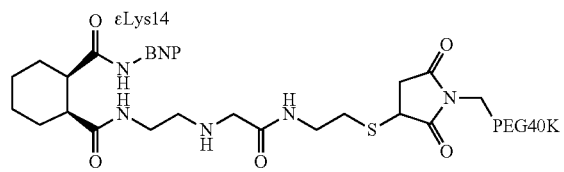

37b 37b was synthesized as described for 37a except for the use of 36b instead of 36a.

Yield: 18.5 mg

Example 38

Synthesis of Linker-Exendin Conjugates

Linker-exendin conjugates were synthesized according to general synthesis method A, B, C, D, E or F.

Method A

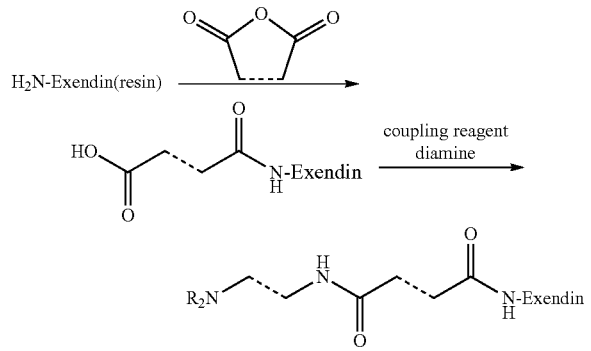

Method B

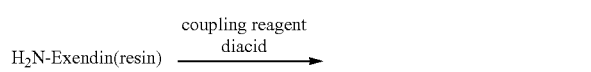

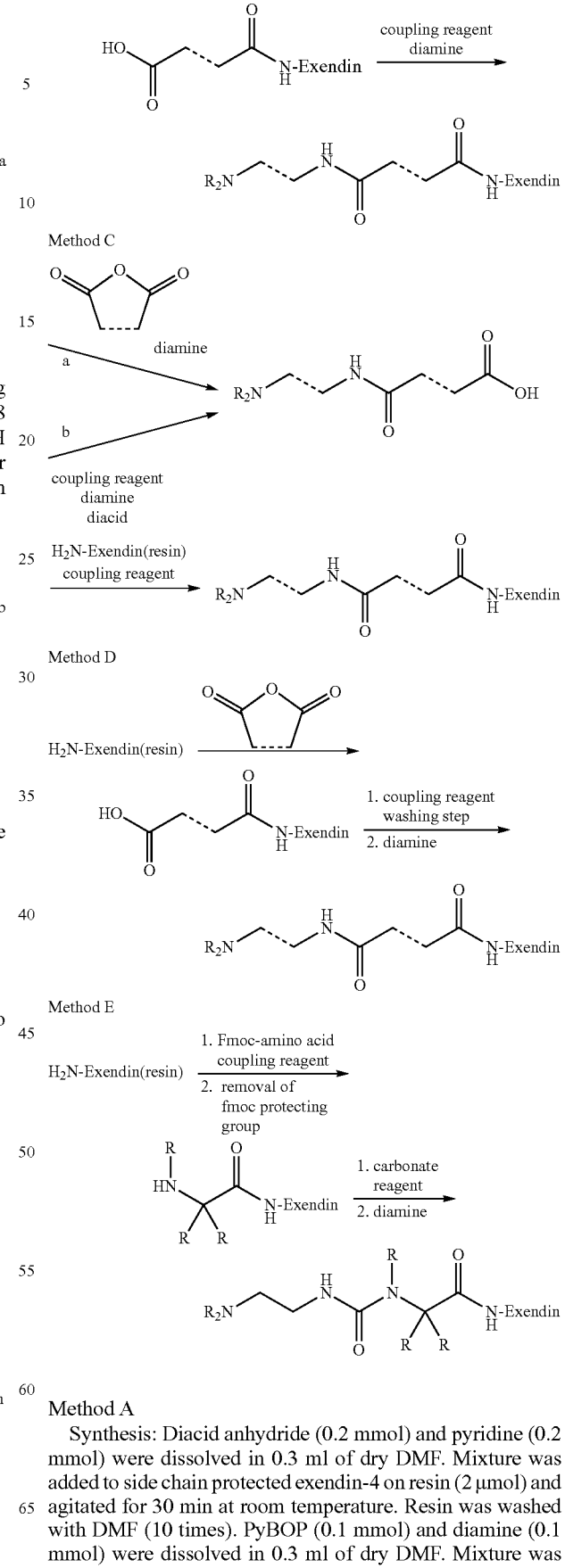

Method A

Synthesis: Diacid anhydride (0.2 mmol) and pyridine (0.2 mmol) were dissolved in 0.3 ml of dry DMF. Mixture was added to side chain protected exendin-4 on resin (2 µmol) and agitated for 30 min at room temperature. Resin was washed with DMF (10 times). PyBOP (0.1 mmol) and diamine (0.1 mmol) were dissolved in 0.3 ml of dry DMF. Mixture was added to resin and agitated for 30 min at room temperature. Resin was washed with DMF (10 times). Exendin-linker conjugates were cleaved and purified by RP-HPLC as described in "Materials and Methods".

Method B

Synthesis: As described for Method A except that diacid anhydride and pyridine are replaced by diacid (0.2 mmol), HOBt (0.2 mmol), DIC (0.2 mmol), and collidine (0.4 mmol).

Method C

Synthesis. Diamine (0.6 mmol) was dissolved in 1 ml of dry DCM and diacid anhydride (0.4 mmol) was added. Mixture was stirred for 60 min at room temperature. DCM was removed, the residue was dissolved in ACN/water/AcOH, and amino acid was purified by RP-HPLC and lyophilized.

Amino acid (0.1 mmol), HOBt (0.1 mmol), DIC (0.1 mmol), and collidine (0.2 mmol) were dissolved in 0.3 ml of dry DMF. Mixture was added to exendin-4 on resin (2 µmol) and agitated for 30 min at room temperature. Resin was washed with DMF (10 times). Exendin-linker conjugates were cleaved and purified by RP-HPLC as described in "Materials and Methods".

Method D

Synthesis: Diacid anhydride (0.2 mmol) and pyridine (0.2 mmol) were dissolved in 0.3 ml of dry DMF. Mixture was added to exendin-4 on resin (2 µmol) and agitated for 30 min at room temperature. Resin was washed with DMF (10 times). PyBOP (0.1 mmol), HOBt (0.1 mmol), and collidine (0.4 mmol) were dissolved in 0.3 ml of dry DMF. Mixture was added to resin and agitated for 30 min at room temperature. Resin was washed with DMF (10 times). Diamine (0.1 mmol) and DIEA (0.3 mmol) were dissolved in a mixture of 0.4 ml of DMF and 0.4 ml of EtOH. Mixture was added to resin and agitated for 30 min at room temperature. Resin was washed with DMF (10 times).

Exendin-linker conjugates were cleaved and purified by RP-HPLC as described in "Materials and Methods".

Method E

Synthesis: Fmoc amino acid (0.1 mmol), PyBOP (0.1 mmol) and DIEA (0.2 mmol) were dissolved in 0.3 ml of dry DMF. Mixture was added to exendin-4 on resin (2 µmol) and agitated for 30 min at room temperature. Fmoc protecting group was removed by incubating resin in DMF/piperidine 4/1 (v/v) for 2×10 min. Resin was washed with DMF (10 times) and DCM (10 times). p-Nitrophenyl chloroformate (0.1 mmol) was dissolved in 0.3 ml of dry THF and DIEA (0.2 mmol). Mixture was added to resin and agitated for 30 min at room temperature. Resin was washed with DCM (10 times). Diamine (0.1 mmol) was dissolved in 0.3 ml of DMF. Mixture was added to resin and agitated for 30 min at room temperature. Resin was washed with DMF (10 times).

Exendin-linker conjugates were cleaved and purified by RP-HPLC as described in "Materials and Methods".

Method F

Synthesis: as described for Method A, followed by fmoc-deprotection and acetylation: Fmoc protecting group was removed as by incubating resin in DMF/piperidine 4/1 (v/v) for 2×10 min. Resin was washed with DMF (10 times). Acetylation was performed by incubating resin with acetic anhydride/pyridine/DMF 1/1/2 (v/v/v) for 30 min. Resin was washed with DMF (10 times).

Exendin-linker conjugates were cleaved and purified by RP-HPLC as described in "Materials and Methods".

Further details concerning compound numerals, starting materials, synthesis method, molecular weight (MW) and MS data are given in FIG. 2.

Example 39

Synthesis of Hydrogel-Linker-Exendin Conjugates 39

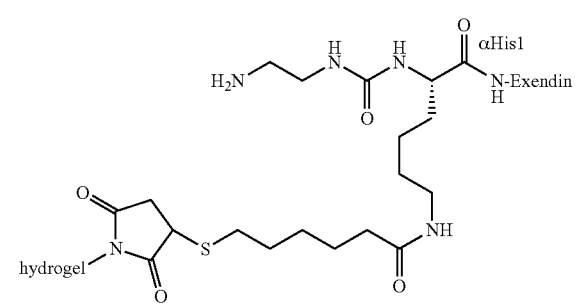

Maleimide-functionalized hydrogel microparticles were synthesized as described in EP 1 625 856 A1.

30 mg of maleimide-derivatized hydrogel microparticles (loading 40 mmol/g, 1.2 µmol) were reacted with 6 mg of compound 25a (1.32 µmol, 1.1 eq) in 600 µl 20/80 (v/v) acetonitrile/50 mM phosphate buffer (pH 7.4) for 10 min to give exendin-linker loaded hydrogel microparticles 39. The loaded hydrogel 39 was washed 5 times with 50/50 (v/v) acetonitrile/water and three times with water.

Example 40

Synthesis of Linker 40

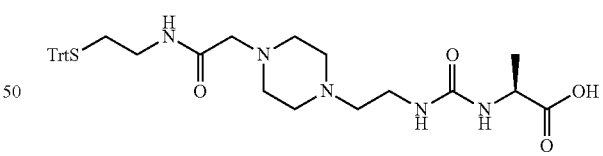

Fmoc-Ala-OH (250 mg, 0.8 mmol) and DIEA (170 µL, 1.0 mmol) were dissolved in DCM (2 mL), added to 2-chlorotrityl chloride resin (312 mg, 1.3 mmol/g) and agitated for 45 min at RT. Methanol (0.6 mL) was added and the resin was incubated for another 15 min. The resin was washed with DCM (10×) and DMF (10×). Fmoc-deprotection and urea formation was achieved according to general procedures (see Materials and Methods) by reaction with linker intermediate 5a, the product was cleaved from the resin and purified by RP-HPLC.

Yield: 53 mg

MS 40: m/z 604.4 [M+H]$^+$ (MW calculated=603.8 g/mol)

Example 41

Synthesis of Exendin-Linker Conjugate 41

40 (HCl salt, 14.0 mg, 0.02 mmol), PyBOP (10.2 mg, 0.02 mmol) and DIEA (17 μL, 0.1 mmol) were dissolved in DMF (300 μL), immediately added to resin bound, side chain protected exendin (100 mg, 10 μmol) and incubated for 4 h at RT. The resin was washed with DMF (10×), DCM (10×) and dried in vacuo. The product was cleaved from the resin and purified by RP-HPLC.

Yield: 5.4 mg

MS 40: m/z 1510.9=$[M+3H]^{3+}$ (MW calculated=4530.1 g/mol)

Example 42

Synthesis of Fatty Acid-Linker Conjugate 42

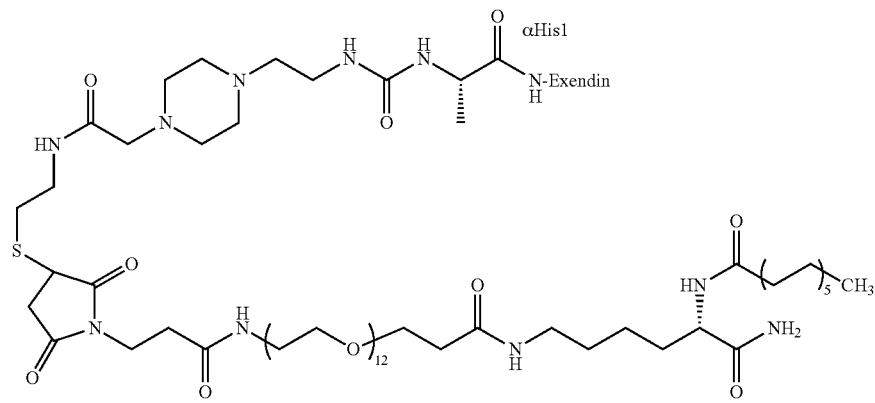

41 (1.6 mg) was dissolved in 200 μl 3/1 acetonitrile/water and 1 (0.11 mg) in 200 μl of 3/1 acetonitrile/water was added. 30 μl of 0.25 M sodium phosphate buffer was added, the reaction was stirred for 5 min, after which 42 was purified by RP-HPLC.

MS 42: m/z 1870.2=$[M+3H]^{3+}$ (MW calculated=5608.4 g/mol).

Example 43

Synthesis of Hydrogel-Linker-Exendin Conjugate 43

43 was synthesized as described for 39 except for the use of 41 instead of 25a.

Example 44

Synthesis of Linker 44

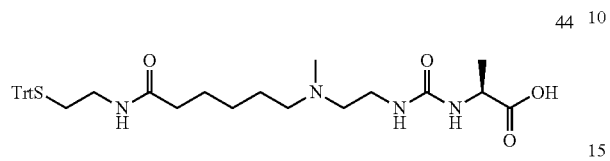

44

44 was synthesized as described for 40 except for the use of 28 instead of 5a.
Yield: 74 mg
MS 44: m/z 605.4 [M+H]$^+$ (MW calculated=604.8 g/mol)

Example 45

Synthesis of Exendin-Linker Conjugate 45

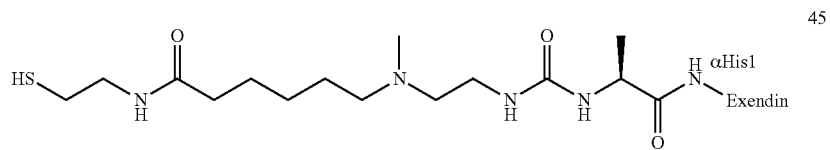

45

45 was synthesized as described for 41 except for the use of 44 instead of 40.
Yield: 6.0 mg
MS 45: m/z 1511.3=[M+3H]$^{3+}$ (MW calculated=4531.1 g/mol)

Example 46

Synthesis of Fatty Acid-Linker Conjugate 46

46 was synthesized as described for 42 except for the use of 45 instead of 41.
MS 46: m/z 1870.5=[M+3H]$^{3+}$ (MW calculated=5609.5 g/mol).

Example 47

Synthesis of Linker Intermediate 47

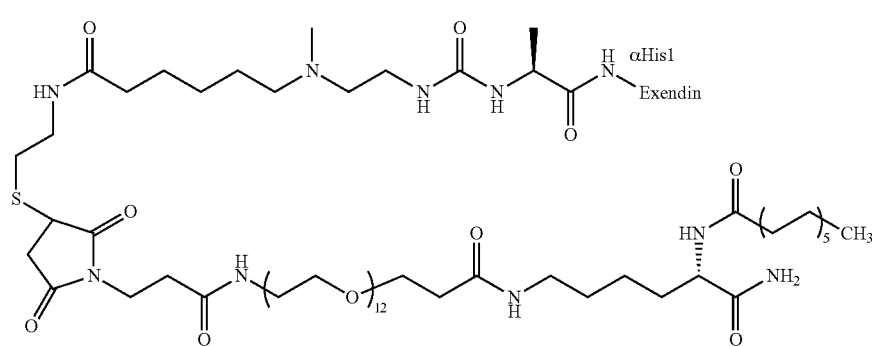

47

Tritylsulfide (247 mg, 0.89 mmol) was suspended in 1 ml DMSO. DBU (152 μl, 1.02 mmol) and 6-bromohexan-1-ol (173 mg, 0.96) were added and mixture was stirred for 5 min at RT. Reaction mixture was dissolved in 20 ml ethylacetate and washed with 1 NH$_2$SO$_4$ (2×) and brine (3×). Organic layer was dried (Na$_2$SO$_4$) and volatiles were removed in vacuo. Product was purified by flash chromatography on silica (heptane/AcOEt 1/1).
Yield 283 mg (S-trityl)-6-mercaptohexan-1-ol

46

(S-Trityl)-6-mercaptohexan-1-ol (466 mg, 1.24 mmol) was dissolved in 3.5 ml DCM, 0.5 ml DMSO and 0.6 ml NEt₃, and cooled in an ice bath. SO₃-pyridine (408 mg, 2.57 mmol) was suspended in 0.5 ml DMSO and added to reaction mixture. Ice bath was removed and reaction was stirred for 60 min at RT. Reaction mixture was dissolved in 20 ml Et₂O and extracted with 1 NH₂SO₄ (2×) and brine (3×). Organic layer was dried (Na₂SO₄) and volatiles were removed in vacuo. Product was purified by flash chromatography on silica (heptane/AcOEt 1/1).

Yield: 390 mg (S-trityl)-6-mercaptohexan-1-al 47

MS 47: m/z 243.1=[Trt]⁺, 413.1=[M+K]⁺ (MW calculated=374.4 g/mol)

Example 48

Synthesis of Linker 48

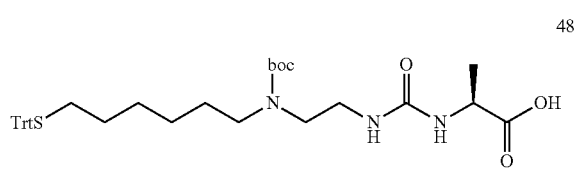

Fmoc-Ala-OH (250 mg, 0.8 mmol) and DIEA (170 μL, 1.0 mmol) were dissolved in DCM (2 mL), added to 2-chlorotrityl chloride resin (312 mg, 1.3 mmol/g) and agitated for 45 min at RT. Methanol (0.6 mL) was added and the resin was incubated for another 15 min. The resin was washed with DCM (10×) and DMF (10×). Fmoc-deprotection and urea formation was achieved according to general procedures (see Materials and Methods) by reaction with ethylene diamine. For reductive alkylation 47 (299 mg, 0.8 mmol) and Na(OAc)₃BH (340 mg, 1.6 mmol) were dissolved in 0.5 mL DMF, 0.5 ml MeOH and 10 μL AcOH, added to resin and agitated for 2 h at RT. Resin was washed with DMF (10×) and DCM (10×). Boc protection was performed by agitating resin in a solution of boc anhydride (218 mg, 1.0 mmol) and DIEA (170 μL, 1.0 mmol) in DCM. Resin was washed with DCM (10×) and product was cleaved from the resin and purified by RP-HPLC.

Yield: 34 mg

MS 48: m/z 634.2 [M+H]⁺ (MW calculated=633.9 g/mol)

Example 49

Synthesis of Exendin-Linker Conjugate 49

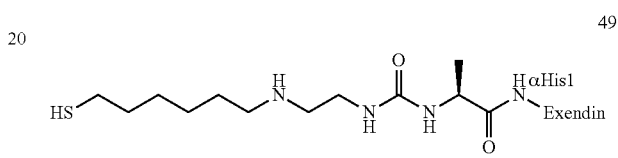

49 was synthesized as described for 41 except for the use of 48 instead of 40.

Yield: 4.8 mg

MS 49: m/z 1487.3=[M+3H]³⁺ (MW calculated=4460.0 g/mol)

Example 50

Synthesis of Hydrogel-Linker-Exendin Conjugate 50

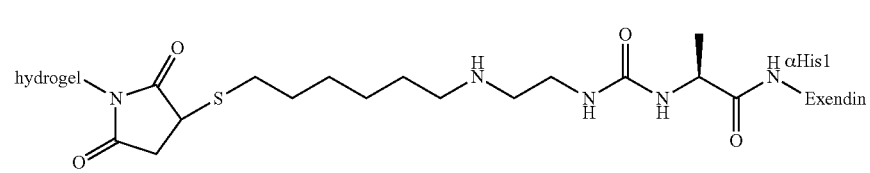

50 was synthesized as described for 39 except for the use of 49 instead of 25a.

Example 51

Release Kinetics In Vitro

Release of drug molecule from 38a to 38z, 38aa to 38ab, 4, 5, 9a, 9b, 9c, 10, 13a, 15, 19a, 19b, 22, 26a to 26c, 31a, 31b, 34a, 34b, 37a, 37b, 42, 43, 46, and 50 was effected by hydrolysis in buffer at pH 7.4 and 37° C. or pH 4 and 37° C. as described in "Materials and Methods".

| Compound | t₁/₂ buffer A (pH 7.4) | t₁/₂ buffer B (pH 4.0) |
|---|---|---|
| 38a | <1 h | 13 h |
| 38b | 20 h | 72 d |
| 38c | >3 m | >3 m |
| 38d | 58 d | n.d. |
| 38e | 41 d | n.d. |
| 38f | 23 h | 114 d |
| 38g | 19 d | none |
| 38h | 47 d | none |
| 38i | 69 h | 108 d |
| 38j | 16 d | n.d. |
| 38k | 40 min | 6 d |
| 38l | 16 h | n.d. |
| 38m | 17 h | 66 d |
| 38n | 18 d | n.d. |
| 38o | 11-12 h | 22 d |
| 38p | 26 d | 178 d |
| 38q | 26 d | 210 d |
| 38r | 26 h | 47 d |
| 38s | 80 min | 80 h |
| 38t | 96 min | 67 h |
| 38u | 51 d | none |
| 38v | 47 d | none |
| 38w | 8 d | 3.2 a |
| 38x | 72 d | n.d. |
| 38y | 11-14 h | 105 d |
| 38z | 11 d | 1.6 a |
| 38aa | 40 h | 65 d |
| 38ab | 20 h | 20 d |
| 38ac | 14 h | n.d. |
| 38ad | 18 h | n.d. |
| 4 | 15 d | n.d. |
| 5 | 22 h | n.d. |
| 9a | 340 h | n.d |
| 9b | 360 h | n.d |
| 9c | 120 h | n.d |
| 10 | 130 h | n.d |
| 13a | 120 h | n.d |
| 13b | 160 h | n.d. |
| 15 | 160 h | n.d |
| 19a | 31 h | n.d. |
| 19b | 18 h | n.d. |
| 22 | 40 d | n.d. |
| 26a | 34 d | n.d. |
| 26b | 40 d | n.d. |
| 26c | 18 d | n.d. |
| 31a | 22 h | n.d. |
| 31b | 95 h | n.d. |
| 34a | 42 h | n.d. |
| 34b | 205 h | n.d. |
| 37a | 138 h | n.d. |
| 37b | 639 h | n.d. |
| 42 | 10 d | n.d. |
| 43 | 17 d | n.d. |
| 46 | 13 d | n.d. |
| 50 | 35 d | n.d. |

Example 52

Release Kinetics In vivo—In vitro/In vivo Correlation

Release kinetics in vivo were determined by comparing the pharmacokinetics of 13a with the pharmacokinetics of 13c and 13b with 13d, respectively, after intravenous injection into rat. Animal studies were performed at Heidelberg Pharma AG, Heidelberg, Germany.

13a (27 mg) was dissolved in 3.5 ml PBS and 500 µl of the resulting solution were injected intravenously into six rats each. Male SD rats with approximately 270 g weight were used. Blood samples were drawn at t=0, 2 h, 24 h, 32 h, 48 h, 72 h, 96 h, 120 h, and 168 h, plasma was prepared, and plasma was analyzed for fluorescein fluorescence using a Perkin-Elmer LS 50B spektrometer.

Pharmacokinetics of 13c were determined as described for 13a. Pharmacokinetics of 13b and 13d were determined as described for 13a, except for the use of 20 mg 13 b and 13d each in 2.5 ml PBS and four rats.

Linker hydrolysis half-life was calculated from the ratio of fluorescence of 13a compared to fluorescence of 13c and 13b compared to 13d, respectively, at the respective time points.

Half-life of in vivo linker hydrolysis was determined to be 115 h and 160 h for 13a and 13b, respectively, which is in excellent correlation to the half-life of in vitro linker hydrolysis of 120 h and 160 h for 13a and 13b, respectively.

Figure 3:
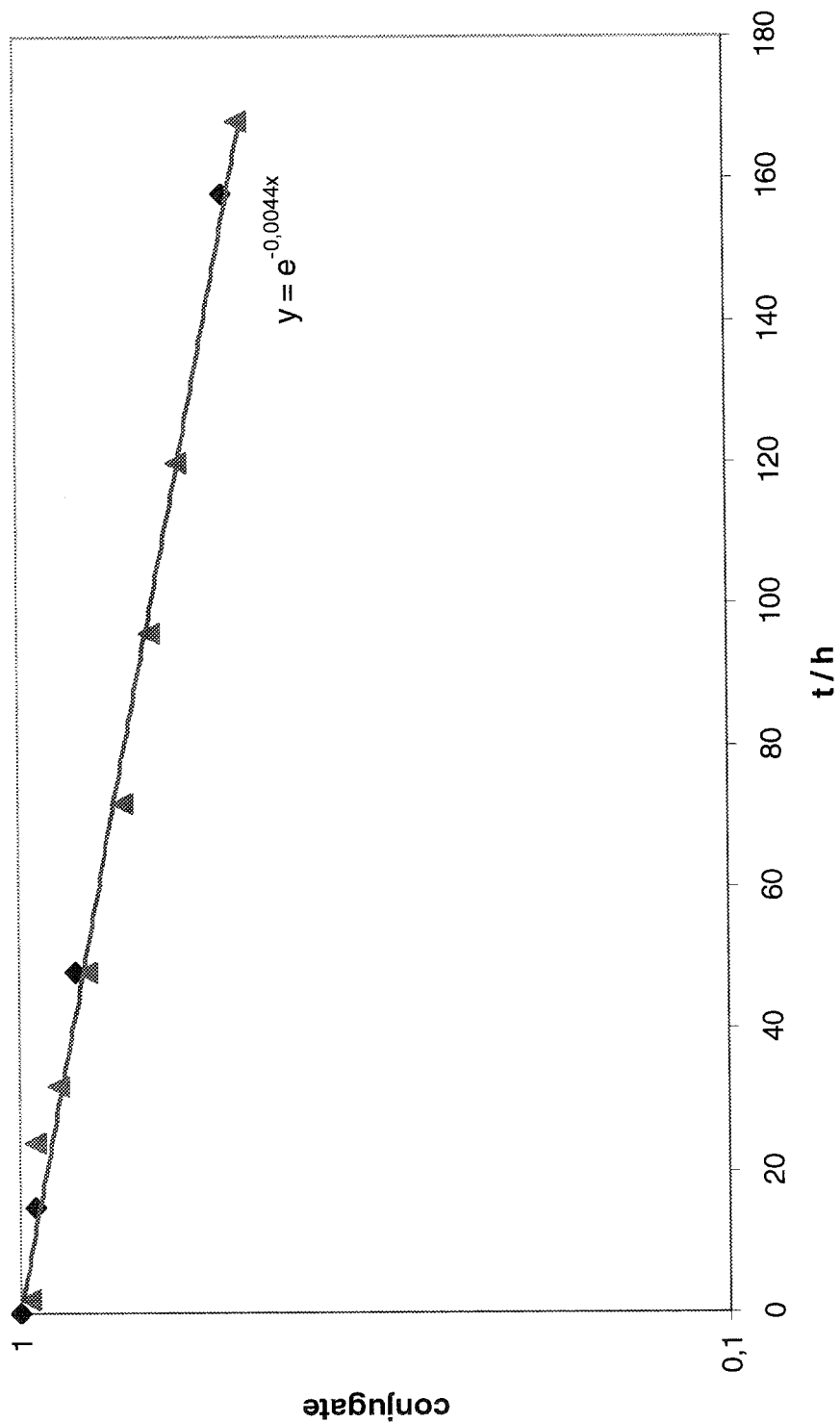
FIG. 3 shows in vivo and in vitro linker cleavage data of 13b, wherein in vivo (triangles) and in vitro (diamonds) cleavage kinetics are shown by semilogarithmic representation.

FIG. 3 shows in vivo and in vitro linker cleavage data of 13b, wherein in vivo (triangles) and in vitro (diamonds) cleavage kinetics are shown by semilogarithmic representation.

ABBREVIATIONS

Acp 4-(2-aminoethyl)-1-carboxymethyl-piperazine
AcOH acetic acid
Boc t-butyloxycarbonyl
Dab 2,4-diaminobutyric acid
DBU 1,3-diazabicyclo[5.4.0]undecene
DCM dichloromethane
Dda dodecanoic acid
DIC diisopropylcarbodiimide
DIEA diisopropylethylamine
DMAP dimethylamino-pyridine
DMF N,N-dimethylformamide
DMSO dimethylsulfoxide
EDTA ethylenediaminetetraacetic acid
eq stoichiometric equivalent
Fmoc 9-fluorenylmethoxycarbonyl
HATU O-(7-Azabenzotriazol-1-yl)-N,N,N',N'-tetramethyluronium hexafluorophosphate
HFIP hexafluoroisopropanol
HEPES N-(2-hydroxyethyl)piperazine-N'-(2-ethanesulfonic acid)
HOBt N-hydroxybenzotriazole
ivDde 1-(4,4-Dimethyl-2,6-dioxo-cyclohexylidene)-3-methylbutyl
LCMS mass spectrometry-coupled liquid chromatography
Mal 3-maleimido propionyl
Mmt 4-methoxytrityl
MS mass spectrum
MW molecular mass
n.d. not determined
PfpOH pentafluorophenol
PyBOP benzotriazole-1-yl-oxy-tris-pyrrolidino-phosphonium hexafluorophosphate
RP-HPLC reversed-phase high performance liquid chromatography
RT room temperature
SEC size exclusion chromatography
Suc succinimidopropionyl
TCP 2-chlorotrityl chloride resin
TES triethylsilane
TMOB 2,4,6-trimethoxybenzyl
TFA trifluoroacetic acid
THF tetrahydrofurane
UV ultraviolet
VIS visual

The invention claimed is:
1. A prodrug or a pharmaceutically acceptable salt thereof comprising:
   a cleavable drug-linker conjugate D-L, which is configured so that the bond between the moiety D and the moiety L is cleaved after the drug-linker conjugate D-L is administered so as to release a drug D-H;

wherein:
- -D is a nitrogen containing biologically active moiety;
- -L is a non-biologically active linker moiety -$L^1$; and
- -$L^1$ comprises an amine-containing nucleophile, and is represented by formula (I):

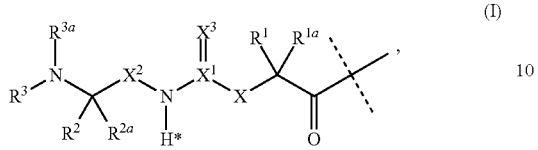

wherein:
the dashed line indicates the attachment to the nitrogen of the biologically active moiety by forming an amide bond;

X is $C(R^4R^{4a})$, $N(R^4)$, O, $C(R^4R^{4a})$, —$C(R^5R^{5a})C(R^5R^{5a})$—$C(R^4R^{4a})$, $C(R^4R^{4a})$—$N(R^6)$, $N(R^6)$—$C(R^4R^{4a})$, $C(R^4R^{4a})$—O, or O—C$(R^4R^{4a})$;

$X^1$ is C, or S(O);

$X^2$ is $C(R^7R^{7a})$, or $C(R^7R^{7a})$—$C(R^8R^{8a})$;

$X^3$ is O, S, or N—CN;

$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, and $R^8$ are independently selected from the group consisting of H, and $C_{1-4}$ alkyl;

optionally, one or more of the pairs $R^{1a}/R^{4a}$, $R^{1a}/R^{5a}$, $R^{4a}/R^{5a}$, and $R^{7a}/R^{8a}$ form a chemical bond;

optionally, one or more of the pairs $R^1/R^{1a}$, $R^2/R^{2a}$, $R^4/R^{4a}$, $R^5/R^{5a}$, $R^7/R^{7a}$, and $R^8/R^{8a}$ joined together with the atom to which they are attached to form a $C_{3-7}$ cycloalkyl, or 4 to 7 membered heterocyclyl;

optionally, one or more of the pairs $R^1/R^4$, $R^1/R^5$, $R^1/R^5$, $R^4/R^6$, $R^7/R^8$, and $R^2/R^3$ are joined together with the atoms to which they are attached to form a ring A;

optionally, $R^3/R^{3a}$ are joined together with the nitrogen atom to which they are attached to form a 4 to 7 membered heterocycle;

A is selected from the group consisting of:
phenyl, naphthyl, indenyl, indanyl, tetralinyl, $C_{3-10}$ cycloalkyl, 4 to 7 membered heterocyclyl, and 9 to 11 membered heterobicyclyl; and
—$N(R^3R^{3a})$ is the amine-containing nucleophile;

wherein $L^1$ is substituted with one to four groups $L^2$-Z and optionally further substituted, provided that the hydrogen marked with the asterisk in formula (I) is not replaced by a substituent, and wherein one or more further optional substituents are independently selected from the group consisting of:

halogen, CN, $COOR^9$, $OR^9$, $C(O)R^9$, $C(O)N(R^9R^{9a})$, $S(O)_2N(R^9R^{9a})$, $S(O)N(R^9R^{9a})$, $S(O)_2R^9$, $S(O)R^9$, $N(R^9)S(O)_2N(R^{9a}R^{9b})$, $SR^9$, $N(R^9R^{9a})$, $NO_2$, $OC(O)R^9$, $N(R^9)C(O)R^{9a}$, $N(R^9)S(O)_2R^{9a}$, $N(R^9)S(O)R^{9a}$, $N(R^9)C(O)OR^{9a}$, $N(R^9)C(O)N(R^{9a}R^{9b})$, $OC(O)N(R^9R^{9a})$, T, $C_{1-50}$ alkyl, $C_{2-50}$ alkenyl, and $C_{2-50}$ alkynyl;

wherein T, $C_{1-50}$ alkyl, $C_{2-50}$ alkenyl, and $C_{2-50}$ alkynyl are optionally substituted with one or more $R^{10}$, which are the same or different;

wherein $C_{1-50}$ alkyl, $C_{2-50}$ alkenyl, and $C_{2-50}$ alkynyl are optionally interrupted by one or more groups selected from the group consisting of:

T, —C(O)O—, —O—, —C(O)—, —C(O)N($R^{11}$)—, —S(O)$_2$N($R^{11}$)—, —S(O)N ($R^{11}$)—, —S(O)$_2$—, —S(O)—, —N($R^{11}$)S(O)$_2$N ($R^{11a}$)—, —S—, —N($R^{11}$)—, —OC(O)$R^{11}$, —N($R^{11}$)C(O)—, —N($R^{11}$)S(O)$_2$—, —N($R^{11}$)S(O)—, —N($R^{11}$)C(O)O—, —N($R^{11}$)C(O)N ($R^{11a}$)—, and —OC(O)N($R^{11}R^{11a}$);

wherein $R^9$, $R^{9a}$, $R^{9b}$ are independently selected from the group consisting of:
H, T, $C_{1-50}$ allkyl, $C_{2-50}$ alkenyl, and $C_{2-50}$ alkynyl;

wherein T, $C_{1-50}$ alkyl, $C_{2-50}$ alkenyl, and $C_{2-50}$ alkynyl are optionally substituted with one or more $R^{10}$, which are the same or different; and wherein $C_{1-50}$ alkyl, $C_{2-50}$ alkenyl, and $C_{2-50}$ alkynyl are optionally interrupted by one or more groups selected from the group consisting of:

T, —C(O)O—, —O—, —C(O)—, —C(O)N($R^{11}$)—, —S(O)$_2$N($R^{11}$)—, —S(O)N($R^{11}$)—, —S(O)$_2$—, —S(O)—, —N($R^{11}$)S(O)$_2$N ($R^{11a}$)—, —S—, —N($R^{11}$)—, —OC(O)$R^{11}$, —N($R^{11}$)C(O)—, —N($R^{11}$)S(O)$_2$—, —N($R^{11}$) S(O)—, —N($R^{11}$)C(O)O—, —N($R^{11}$)C(O)N ($R^{11a}$)—, and —OC(O)N($R^{11}R^{11a}$);

wherein T is selected from the group consisting of:
phenyl, naphthyl, indenyl, indanyl, tetralinyl, $C_{3-10}$ cycloalkyl, 4 to 7 membered heterocyclyl, and 9 to 11 membered heterobicyclyl;

wherein T is optionally substituted with one or more $R^{10}$, which are the same or different;

wherein $R^{10}$ is:
halogen, CN, oxo (=O), $COOR^{12}$, $OR^{12}$, $C(O)R^{12}$, $C(O)N(R^{12}R^{12a})$, $S(O)_2N(R^{12}R^{12a})$, $S(O)N(R^{12}R^{12a})S(O)_2R^{12}$, $S(O)R^{12}$, $N(R^{12})S(O)_2N(R^{12a}R^{12b})$, $SR^{12}$, $N(R_{12}R^{12a})$, $NO_2$, $OC(O)R^{12}$, $N(R^{12})C(O)R^{12a}$, $N(R^{12})S(O)_2R^{12a}$, $N(R^{12})S(O)R^{12a}$, $N(R^{12})C(O)OR^{12a}$, $N(R^{12})C(O)N(R^{12a}R^{12b})$, $OC(O)N(R^{12}R^{12a})$, or $C_{1-6}$ alkyl;

wherein $C_{1-6}$ alkyl is optionally substituted with one or more halogen, which are the same or different; and wherein $R^{11}$, $R^{11a}$, $R^{12}$, $R^{12a}$, and $R^{12b}$ are independently selected from the group consisting of:
H and $C_{1-6}$ alkyl;

wherein $C_{1-6}$ alkyl is optionally substituted with one or more halogen, which are the same or different;

wherein $L^2$ is a single chemical bond or a spacer; and wherein Z is a carrier group.

2. The prodrug of claim 1;
wherein $X^3$ is O.

3. The prodrug of claim 1;
wherein:
X is $N(R^4)$;
$X^1$ is C; and
$X^3$ is O.

4. The prodrug of claim 1;
wherein $X^2$ is $C(R^7R^{7a})$.

5. The prodrug of claim 1;
wherein $L^1$ is selected from the group consisting of:
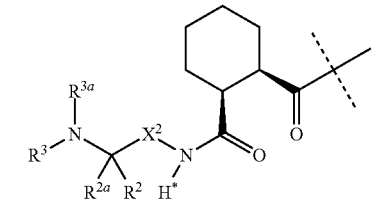
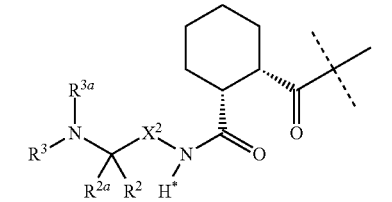
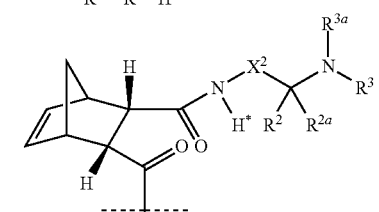
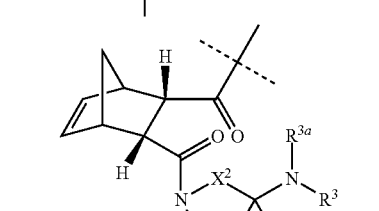
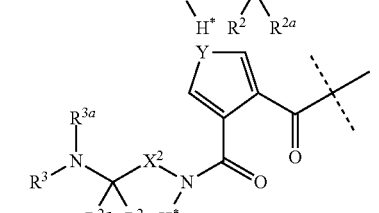
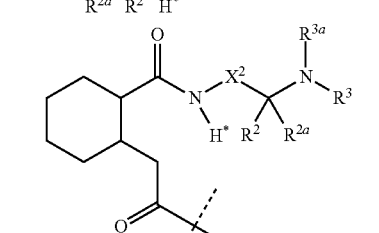
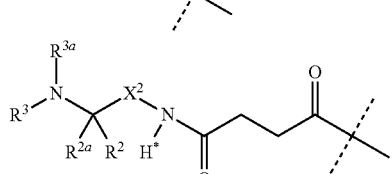
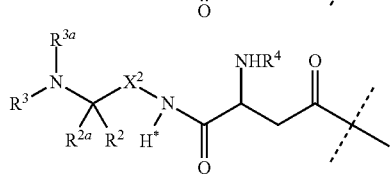
-continued
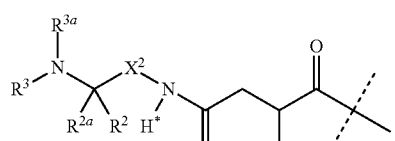
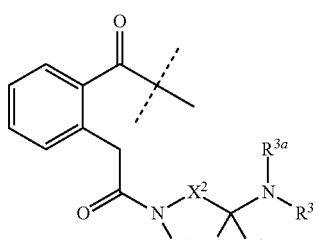
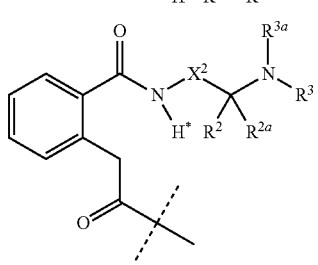
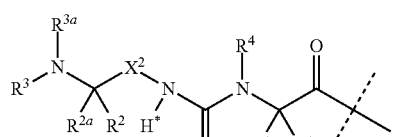
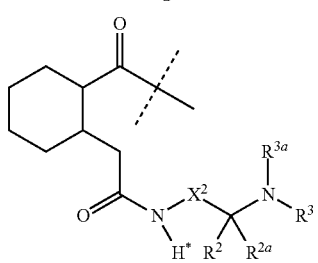
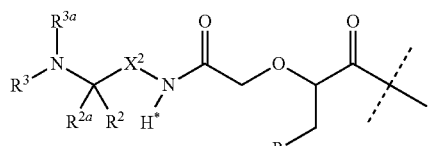
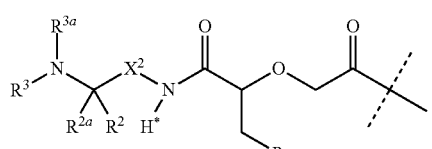
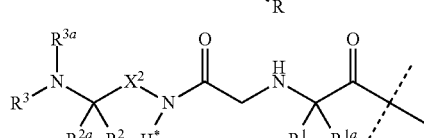
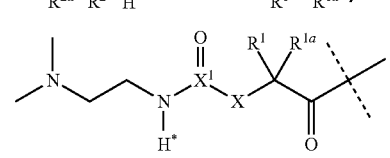

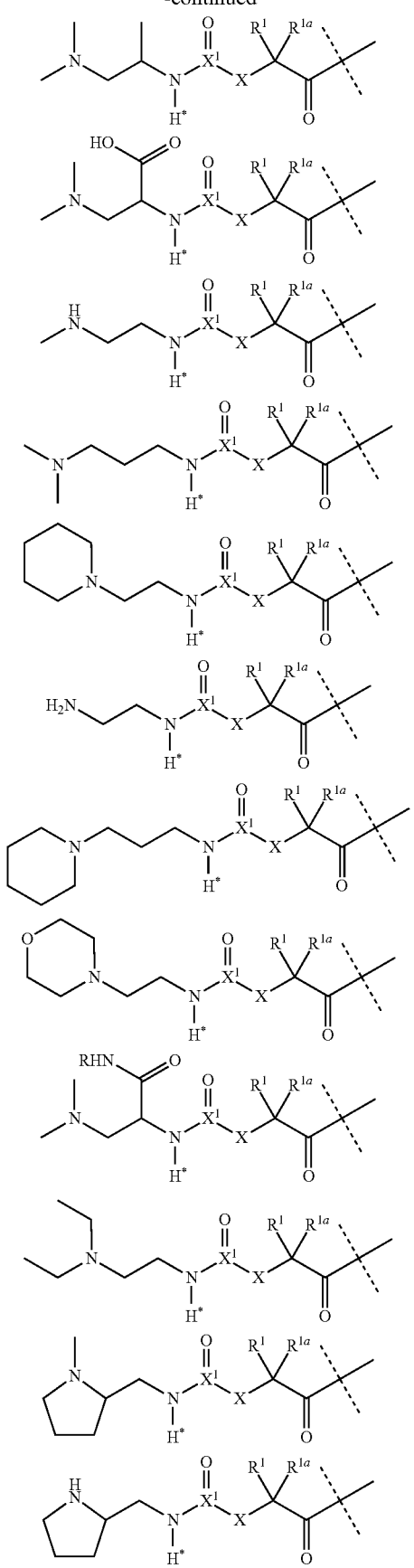
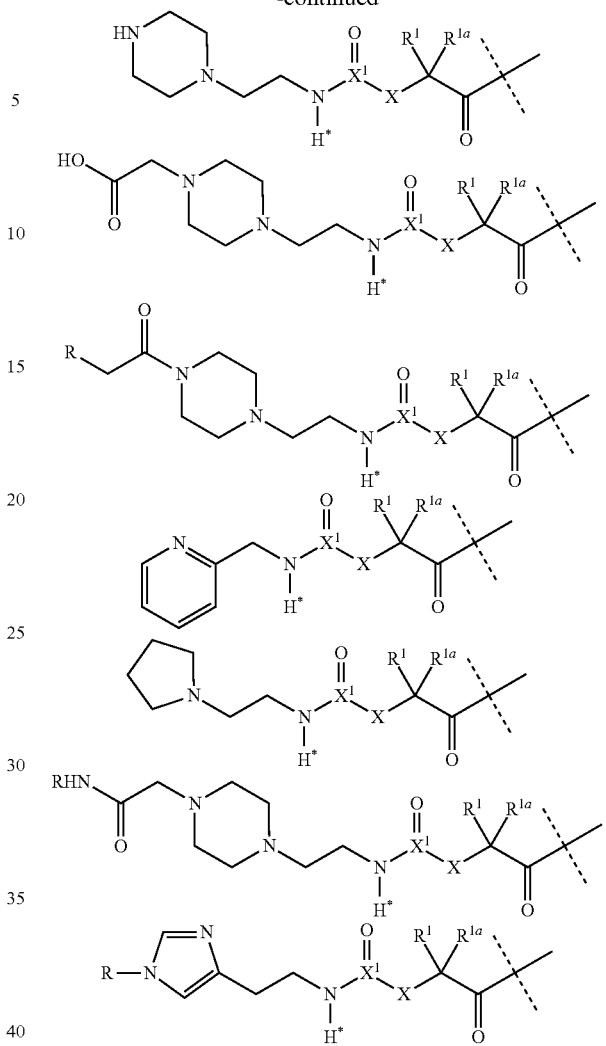
wherein:
R is H, or $C_{1-4}$ alkyl; and
Y is NH, O, or S.
6. The prodrug of claim 1;
wherein $L^1$ is selected from the group consisting of:
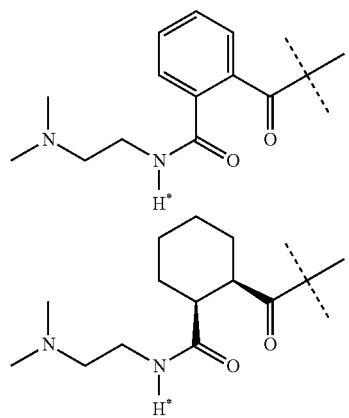

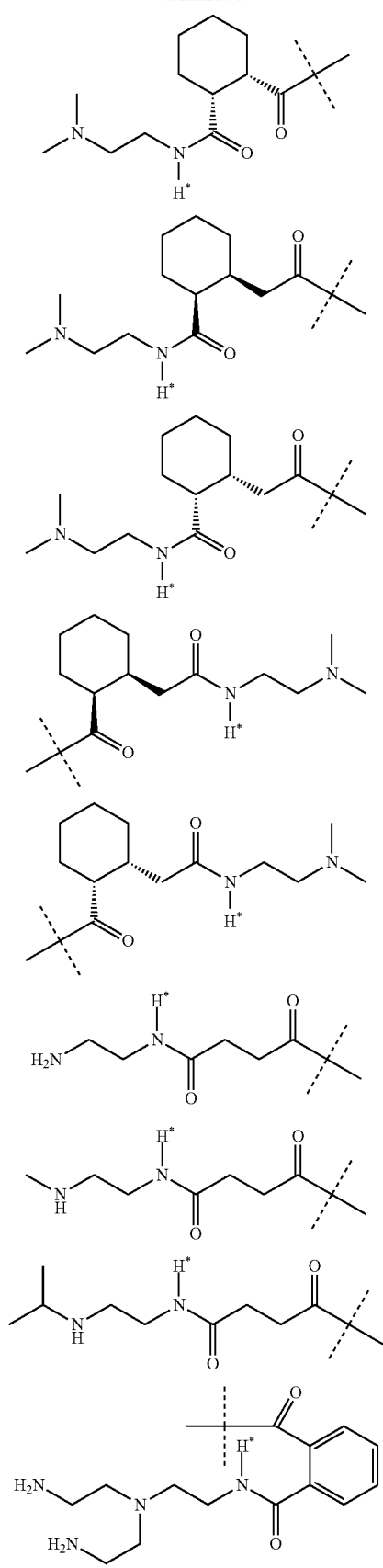
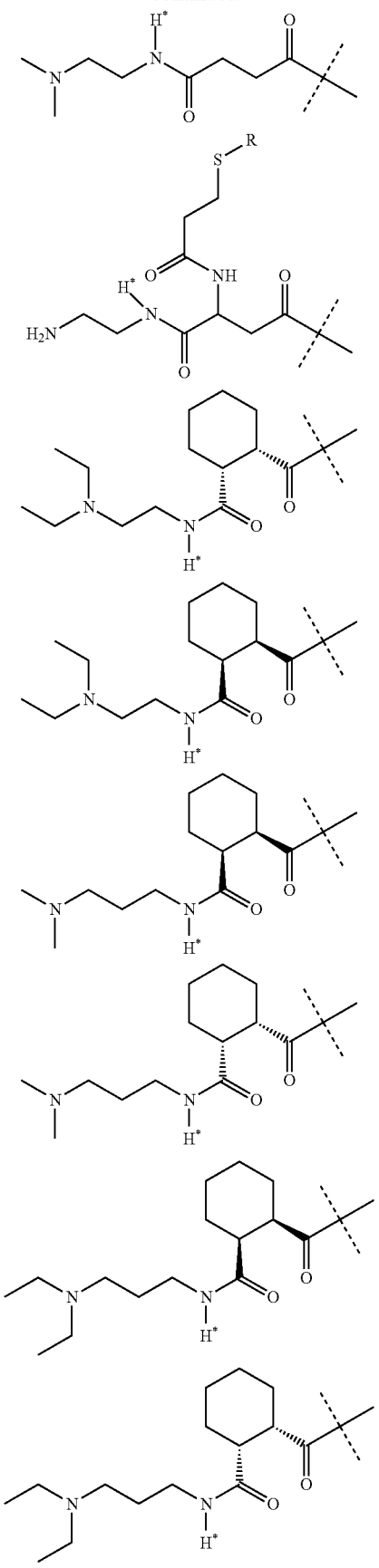

81
-continued
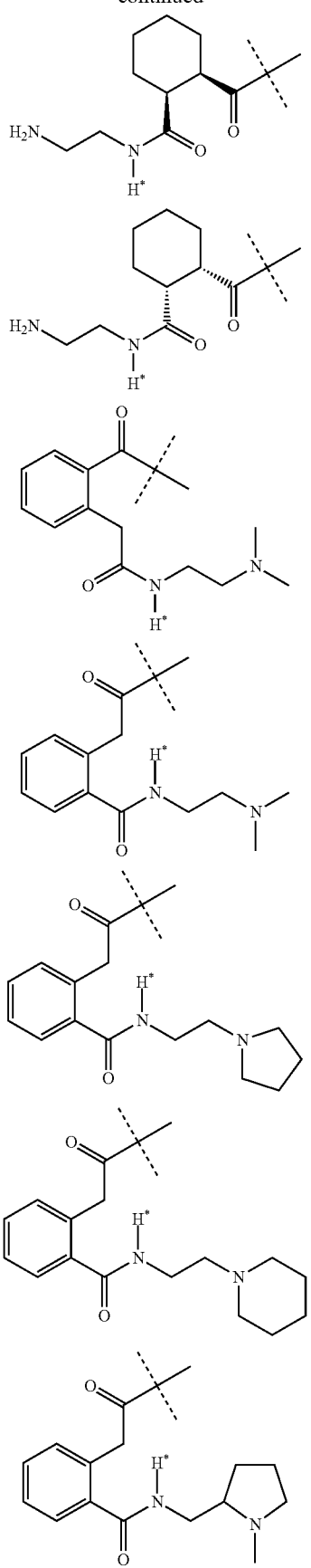
82
-continued
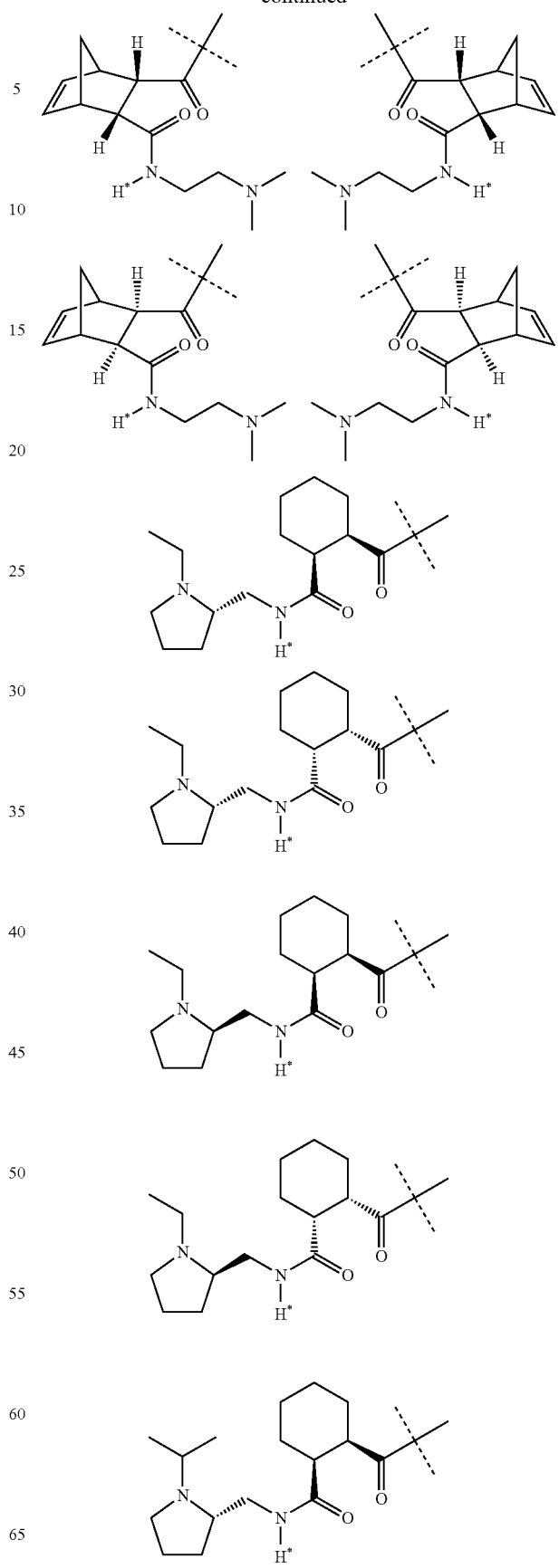

83
-continued
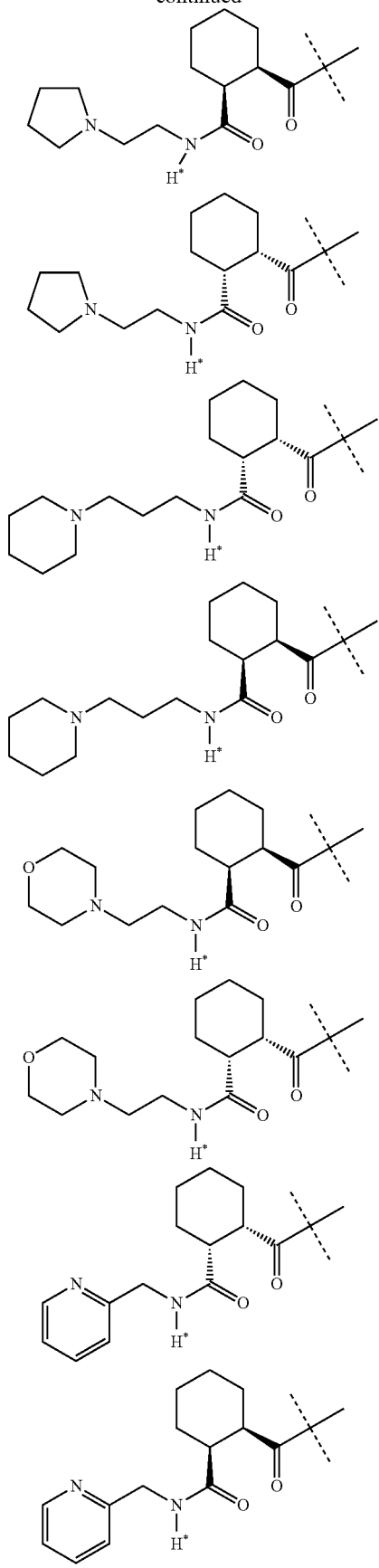
84
-continued
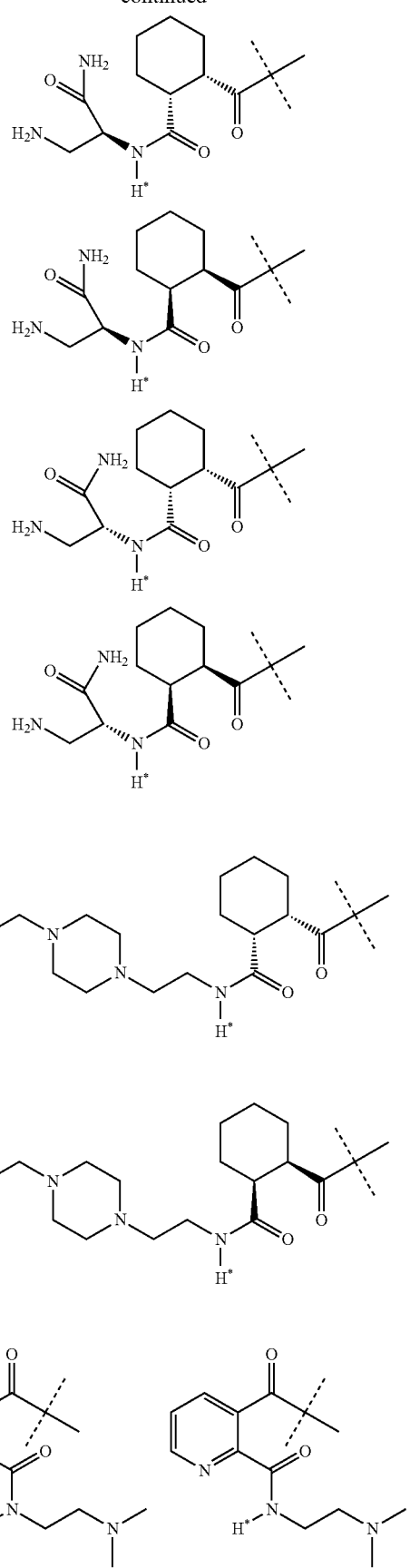

85
-continued
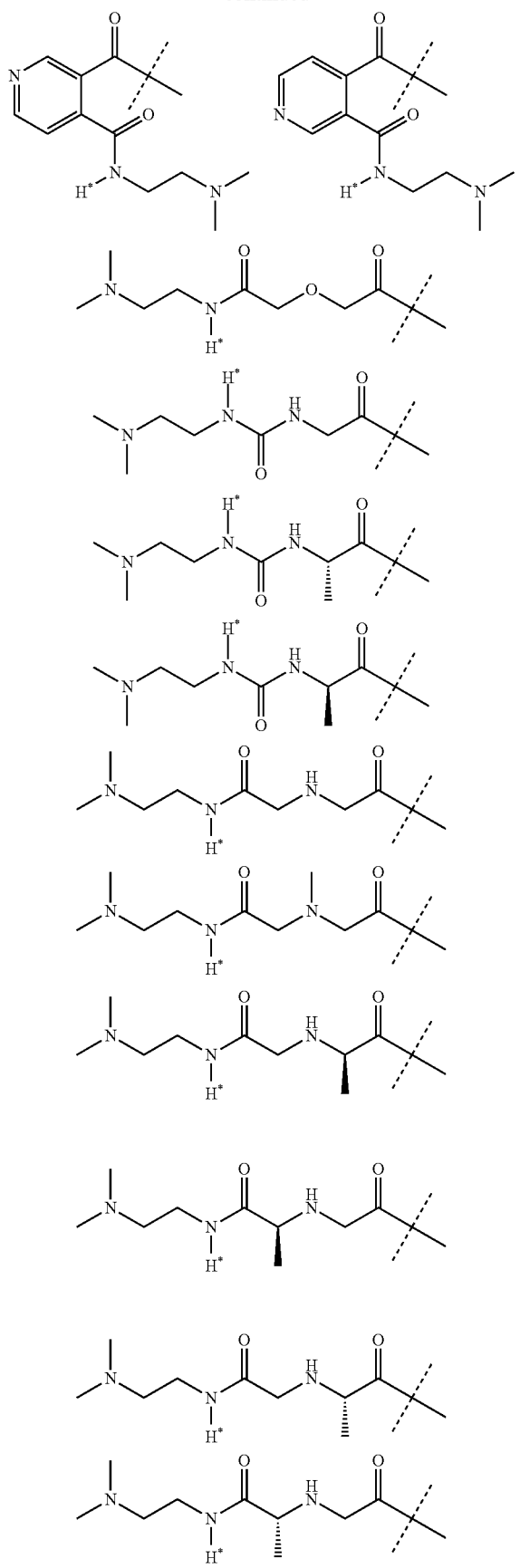
86
-continued
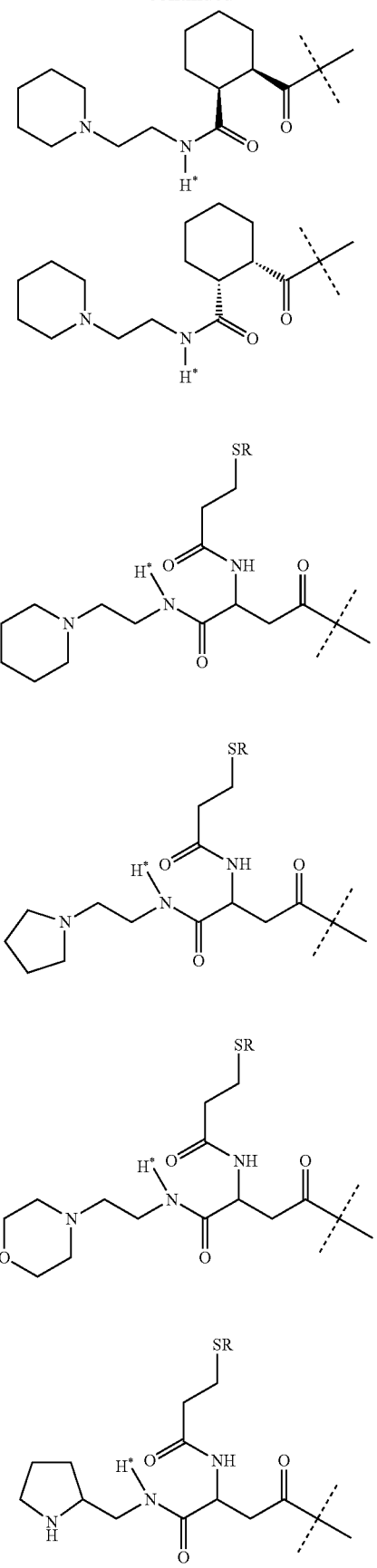

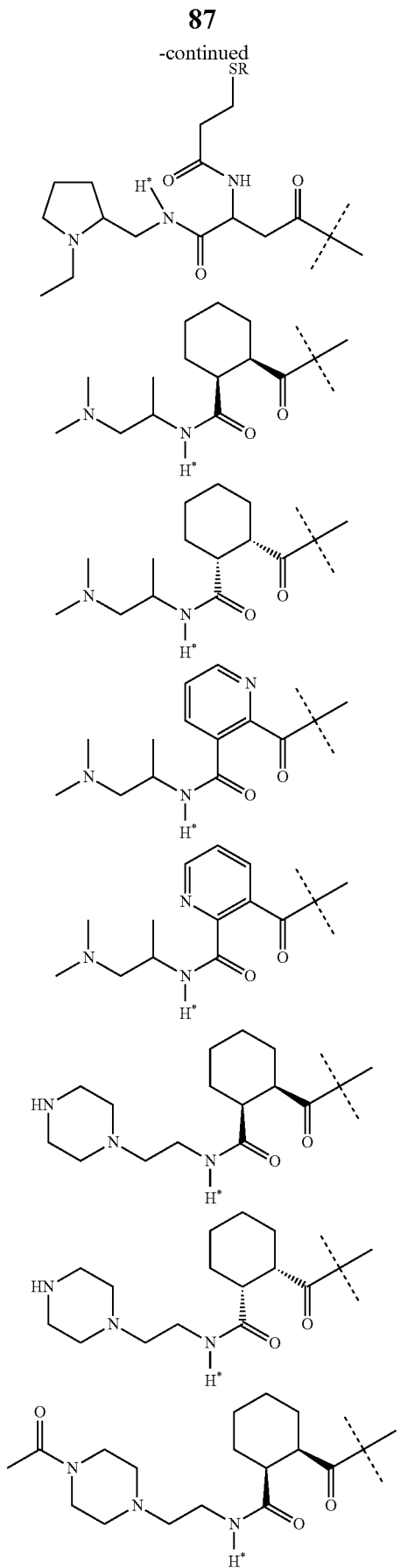

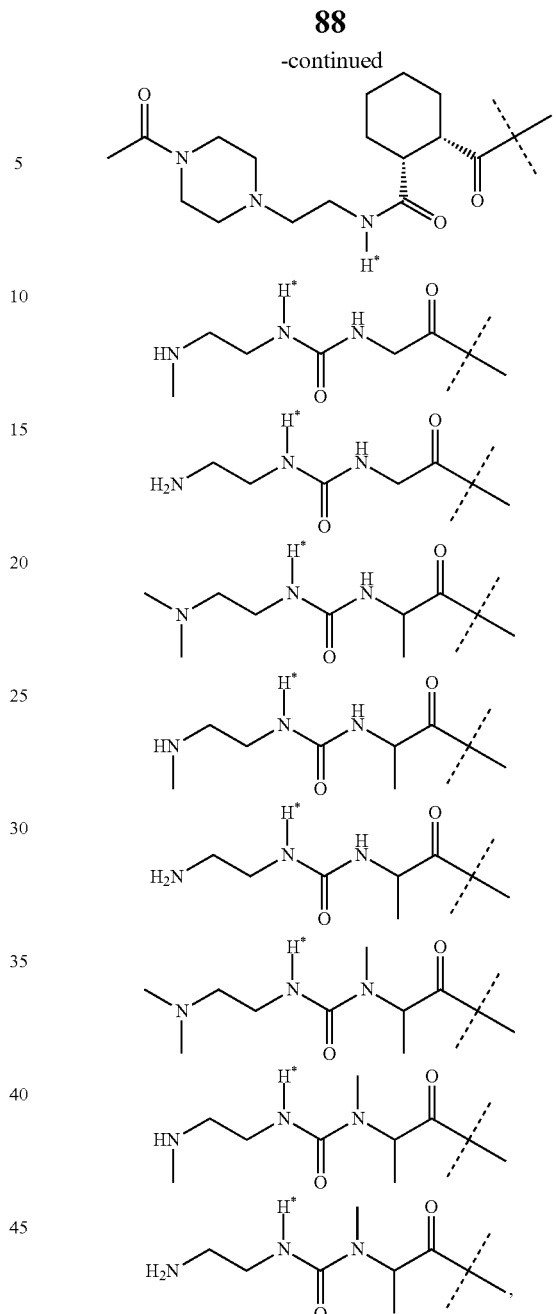

wherein R is H, or $C_{1-4}$ alkyl.

7. The prodrug of claim 1;
wherein:
  $L^2$ is a single chemical bond; or
  $L^2$-Z is selected from the group consisting of:
    $COOR^9$, $OR^9$, $C(O)R^9$, $C(O)N(R^9R^{9a})$, $S(O)_2N(R^9R^{9a})$, $S(O)N(R^9R^{9a})$, $S(O)_2R^9$, $S(O)R^9$, $N(R^9)S(O)_2N(R^{9a}R^{9b})$, $SR^9$, $N(R^9R^{9a})$, $OC(O)R^9$, $N(R^9)C(O)R^{9a}$, $N(R^9)S(O)_2R^{9a}$, $N(R^9)S(O)R^{9a}$, $N(R^9)C(O)OR^{9a}$, $N(R^9)C(O)N(R^{9a}R^{9b})$, $OC(O)N(R^9R^{9a})$, T, $C_{1-50}$ alkyl, $C_{2-50}$ alkenyl, and $C_{2-50}$ alkynyl;
    wherein T, $C_{1-50}$ alkyl, $C_{2-50}$ alkenyl, and $C_{2-50}$ alkynyl are optionally substituted with one or more $R^{10}$, which are the same or different; and
    wherein $C_{1-50}$ alkyl, $C_{2-50}$ alkenyl, and $C_{2-50}$ alkynyl are optionally interrupted by one or more groups selected from the group consisting of —T—, —C(O)O—, —O—, —C(O)—, —C(O)N
(R$^{11}$)—, —S(O)$_2$N(R$^{11}$)—, —S(O)N(R$^{11}$)—,
—S(O)$_2$—, —S(O)—, —N(R$^{11}$)S(O)$_2$N
(R$^{11a}$)—, —S—, —N(R$^{11}$)—, —OC(O)R$^{11}$,
—N(R$^{11}$)C(O)—, —N(R$^{11}$)S(O)$_2$—, —N(R$^{11}$)
S(O)—, —N(R$^{11}$)C(O)O—, —N(R$^{11}$)C(O)N
(R$^{11a}$)—, and —OC(O)N($^{R11}$R$^{11a}$); and wherein:
R$^9$, R$^{9a}$, and R$^{9b}$ are independently selected from the group consisting of:
H, Z, T, C$_{1-50}$ alkyl, C$_{2-50}$ alkenyl, and C$_{2-50}$ alkynyl;
wherein T, C$_{1-50}$ alkyl, C$_{2-50}$ alkenyl, and C$_{2-50}$ alkynyl are optionally substituted with one or more R$^{10}$, which are the same or different; and
wherein C$_{1-50}$ alkyl, C$_{2-50}$ alkenyl, and C$_{2-50}$ alkynyl are optionally interrupted by one or more groups selected from the group consisting of:
T, —C(O)O—, —O—, —C(O)—, —C(O)N
(R$^{11}$)—, —S(O)$_2$N(R$^{11}$)—, —S(O)N(R$^{11}$)—,
—S(O)$_2$—, —S(O)—, —N(R$^{11}$)S(O)$_2$N
(R$^{11a}$)—, —S—, —N(R$^{11}$)—, —OC(O)R$^{11}$,
—N(R$^{11}$)C(O)—, —N(R$^{11}$)S(O)$_2$—, —N(R$^{11}$)
C(O)O—, —N(R$^{11}$)C(O)N(R$^{11a}$)—, and —OC
(O)N(R$^{11}$R$^{11a}$);

T is selected from the group consisting of:
phenyl, naphthyl, indenyl, indanyl, tetralinyl, C$_{3-10}$ cycloalkyl, 4 to 7 membered heterocyclyl, and 9 to 11 membered heterobicyclyl;
wherein T is optionally substituted with one or more R$^{10}$, which are the same or different;

R$^{10}$ is selected from the group consisting of:
Z, halogen, CN, oxo (=O), COOR$^{12}$, OR$^{12}$, C(O)
R$^{12}$, C(O)N(R$^{12}$R$^{12a}$), S(O)$_2$N(R$^{12}$R$^{12a}$), S(O)N
(R$^{12}$R$^{12a}$), S(O)$_2$R$^{12}$, S(O)R$^{12}$, N(R$^{12}$)S(O)$_2$N
(R$^{12a}$R$^{12b}$), SR$^{12}$, N(R$^{12}$R$^{12a}$), NO$_2$; OC(O)R$^{12}$,
N(R$^{12}$)C(O)R$^{12a}$, N(R$^{12}$)S(O)$_2$R$^{12a}$, N(R$^{12}$)S(O)
R$^{12a}$, N(R$^{12}$)C(O)OR$^{12a}$, N(R$^{12}$)C(O)N
(R$^{12a}$R$^{12b}$)OC(O)N(R$^{12}$R$^{12a}$), and C$_{1-6}$ alkyl;
wherein C$_{1-6}$ alkyl is optionally substituted with one or more halogen, which are the same or different; and R$^{11}$, R$^{11a}$, R$^{12}$, R$^{12a}$, and R$^{12b}$ are independently selected from the group consisting of:
H, Z, or C$_{1-6}$ alkyl;
wherein C$^{1-6}$, alkyl is optionally substituted with one or more halogen, which are the same or different;
provided that one of R$^9$, R$^{9a}$, R$^{9b}$, R$^{10}$, R$^{11}$, R$^{11a}$, R$^{12}$, R$^{12a}$, and R$^{12b}$ is Z.

8. The prodrug of claim 1;
wherein L$^2$ is a C$_{1-20}$ alkyl chain, which is:
optionally interrupted by one or more groups independently selected from —O— and C(O)N(R$^{3aa}$); and
optionally substituted with one or more groups independently selected from OH and C(O)N(R$^{3aa}$R$^{3aaa}$); and
wherein R$^{3aa}$ and R$^{3aaa}$ are independently selected from the group consisting of H, and C$_{1-4}$ alkyl.

9. The prodrug of claim 1;
wherein L$^2$ has a molecular weight in the range of from 14 g/mol to 750 g/mol.

10. The prodrug of claim 1;
wherein L$^2$ is attached to Z via a terminal group selected from the group consisting of:

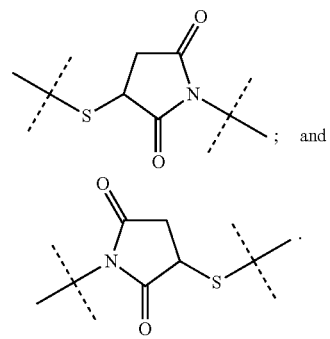
; and

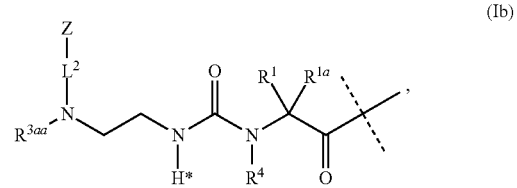
.

11. The prodrug of claim 1;
wherein L is represented by formula (Ia):

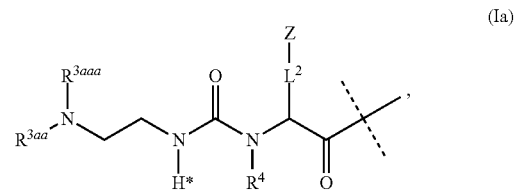
(Ia)

wherein R$^{3aa}$ and R$^{3aaa}$:
are independently selected from the group consisting of H and C$_{1-4}$ alkyl; or
are joined together with the nitrogen atom to which they are attached to form a 4 to 7 membered heterocycle.

12. The prodrug of claim 1;
wherein L is represented by formula (Ib):

(Ib)

wherein R$^{3aa}$ is H or C$_{1-4}$ alkyl.

13. The prodrug of claim 1;
wherein R$^1$ in formula (I) is L$^2$-Z.

14. The prodrug of claim 1;
wherein R$^3$ in formula (I) is L$^2$-Z.

15. The prodrug of claim 1;
wherein R$^3$ and R$^{3a}$ in formula (I) are joined together with the nitrogen atom to which they are attached to form a 4 to 7 membered heterocycle which is substituted with L$^2$-Z.

16. The prodrug of claim 1;
wherein D-H is a small molecule bioactive agent or a biopolymer.

17. The prodrug of claim 1;
wherein D-H is a biopolymer selected from the group of biopolymers consisting of proteins, polypeptides, oligonucleotides, and peptide nucleic acids.

18. The prodrug of claim 1;
wherein D-H is a polypeptide selected from the group of polypeptides consisting of:

ACTH, adenosine deaminase, agalsidase, alfa-1 antitrypsin (AAT), alfa-1 proteinase inhibitor (API), alteplase, amylins (amylin, symlin), anistreplase, ancrod serine protease, antibodies (monoclonal or polyclonal, and fragments or fusions), antithrombin III, antitrypsins, aprotinin, asparaginases, atosiban, biphalin, bivalirudin, bone-morphogenic proteins, bovine pancreatic trypsin inhibitor (BPTI), cadherin fragments, calcitonin (salmon), collagenase, complement C1 esterase inhibitor, conotoxins, cytokine receptor fragments, DNase, dynorphin A, endorphins, enfuvirtide, enkephalins, erythropoietins, exendins, factor VII, factor VIIa, factor VIII, factor VIIIa, factor IX, fibrinolysin, fibroblast growth factor (FGF), growth hormone releasing peptide 2 (GHRP2), fusion proteins, follicle-stimulating hormones, gramicidin, ghrelin, desacyl-ghrelin, granulocyte colony stimulating factor (G-CSF), galactosidase, glucagon, glucagon-like peptides, glucocerebrosidase, granulocyte macrophage colony stimulating factor (GM-CSF), human heat shock proteins (HSP), phospholipase-activating protein (PLAP), gonadotropin chorionic (hCG), hemoglobins, hepatitis B vaccines, hirudin, human serine protease inhibitor, hyaluronidases, idurnonidase, immune globulins, influenza vaccines, interleukins (1 alfa, 1 beta, 2, 3, 4, 6, 10, 11, 12, 13, 21), IL-1 receptor antagonist (thIL-1ra), insulins, insulin like growth factors, insulin-like growth factor binding protein (rhIGFBP), interferons (alfa 2a, alfa 2b, alfa 2c, beta 1a, beta 1b, gamma 1a, gamma 1b), intracellular adhesion molecule, keratinocyte growth factor (KGF), P-selectin glycoprotein ligand (PSGL), transforming growth factors, lactase, leptin, leuprolide, levothyroxine, luteinizing hormone, lyme vaccine, natriuretic peptides (ANP, BNP, CNP and fragments), neuropeptide Y, pancrelipase, pancreatic polypeptide, papain, parathyroid hormone, PDGF, pepsin, peptide YY, platelet activating factor acetylhydrolase (PAF-AH), prolactin, protein C, thymalfasin, octreotide, secretin, sermorelin, soluble tumor necorsis factor receptor (TNFR), superoxide dismutase (SOD), somatropins (growth hormone), somatoprim, somatostatin, streptokinase, sucrase, terlipressin, tetanus toxin fragment, tilactase, thrombins, thymosin, thyroid stimulating hormone, thyrotropin, tumor necrosis factor (TNF), TNF receptor-IgG Fc, tissue plasminogen activator (tPA), TSH, urodilatin, urate oxidase, urokinase, vaccines, vascular endothelial growth factor (VEGF), vasoactive intestinal peptide, vasopressin, ziconotide, lectin, and ricin.

19. The prodrug of claim 1;
wherein D-H is a protein prepared by recombinant DNA technologies.

20. The prodrug of claim 1;
wherein D-H is a protein selected from the group of proteins consisting of:
antibody fragments, single chain antigen binding proteins, catalytic antibodies, and fusion proteins.

21. The prodrug of claim 1;
wherein D-H is a small molecule bioactive agent selected from the group of agents consisting of:
central nervous system-active agents, anti-infective, anti-allergic, immunomodulating, anti-obesity, anticoagulants, antidiabetic, anti-neoplastic, antibacterial, anti-fungal, analgesic, contraceptive, anti-inflammatory, steroidal, vasodilating, vasoconstricting, and cardiovascular agents with at least one primary or secondary amino group.

22. The prodrug of claim 1;
wherein D-H is a small molecule bioactive agent selected from the group of agents consisting of:
acarbose, alaproclate, alendronate, amantadine, amikacin, amineptine, aminoglutethimide, amisulpride, amlodipine, amotosalen, amoxapine, amoxicillin, amphetamine, amphotericin B, ampicillin, amprenavir, amrinone, anileridine, apraclonidine, apramycin, articaine, atenolol, atomoxetine, avizafone, baclofen, benazepril, benserazide, benzocaine, betaxolol, bleomycin, bromfenac, brofaromine, carvedilol, cathine, cathinone, carbutamid, cefalexine, clinafloxacin, ciprofloxacin, deferoxamine, delavirdine, desipramine, daunorubicin, dexmethylphenidate, dexmethylphenidate, diaphenylsulfon, dizocilpine, dopamin, dobutamin, dorzolamide, doxorubicin, duloxetine, eflornithine, enalapril, epinephrine, epirubicin, ergoline, ertapenem, esmolol, enoxacin, ethambutol, fenfluramine, fenoldopam, fenoterol, fingolimod, flecainide, fluvoxamine, fosamprenavir, frovatriptan, furosemide, fluoexetine, gabapentin, gatifloxacin, gemiflocacin, gentamicin, grepafloxacin, hexylcaine, hydralazine, hydrochlorothiazide, icofungipen, idarubicin, imiquimod, inversine, isoproterenol, isradipine, kanamycin A, ketamin, labetalol, lamivudine, levobunolol, levodopa, levothyroxine, lisinopril, lomefloxacin, loracarbef, maprotiline, mefloquine, melphalan, memantine, meropenem, mesalazine, mescaline, methyldopa, methylenedioxymethamphetamine, metoprolol, milnacipran, mitoxantron, moxifloxacin, norepinephrine, norfloxacin, nortriptyline, neomycin B, nystatin, oseltamivir, pamidronic acid, paroxetine, pazufloxacin, pemetrexed, perindopril, phenmetrazine, phenelzine, pregabalin, procaine, pseudoephedrine, protriptyline, reboxetine, ritodrine, sabarubicin, salbutamol, serotonin, sertraline, sitagliptin, sotalol, spectinomycin, sulfadiazin, sulfamerazin, sertraline, sprectinomycin, sulfalen, sulfamethoxazol, tacrine, tamsulosin, terbutaline, timolol, tirofiban, tobramycin, tocainide, tosufloxacin, trandolapril, tranexamic acid, tranylcypromine, trimerexate, trovafloxacin, valaciclovir, valganciclovir, vancomycin, viomycin, viloxazine, and zalcitabine.

23. The prodrug of claim 1;
wherein Z is a polymer of at least 500 Da or a $C_{8-18}$ alkyl group.

24. The prodrug of claim 1;
wherein Z is selected from the group of optionally crosslinked polymers consisting of:
poly(propylene glycol), poly(ethylene glycol), dextran, chitosan, hyaluronic acid, alginate, xylan, mannan, carrageenan, agarose, cellulose, starch, hydroxyalkyl starch (HAS), poly(vinyl alcohols), poly(oxazolines), poly(anhydrides), poly(ortho esters), poly(carbonates), poly(urethanes), poly(acrylic acids), poly(acrylamides), poly(acrylates), poly(methacrylates), poly (organophosphazenes), polyoxazoline, poly (siloxanes), poly(amides), poly(vinylpyrrolidone), poly(cyanoacrylates), poly(esters), poly(iminocarbonates), poly(amino acids), collagen, gelatin, hydrogel, a blood plasma protein, and copolymers thereof.

25. The prodrug of claim 1;
wherein Z is a protein.

26. The prodrug of claim 1;
wherein Z is a protein selected from the group consisting of albumin, transferrin, and immunoglobulin.

27. The prodrug of claim 1;
wherein Z is a linear or branched poly(ethylene glycol) with a molecular weight from 2,000 Da to 150,000 Da.

28. The prodrug of claim 1;
wherein:
D-H is a GLP-1 receptor agonist; and
Z is a hydrogel.

29. The prodrug of claim 28;
wherein the GLP-1 receptor agonist is Exendin-4.

30. The prodrug of claim 28;
wherein in formula (I):
X is $N(R^4)$;
$X^1$ is C; and
$X^3$ is O.

31. The prodrug of claim 1;
wherein D-H is a GLP-1 receptor agonist;
wherein L is represented by formula (Ia):

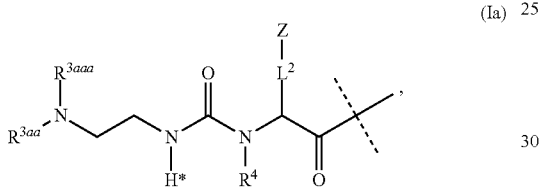

wherein $R^{3aa}$ and $R^{3aaa}$:
are independently selected from the group consisting of H and $C_{1-4}$ alkyl; or
are joined together with the nitrogen atom to which they are attached to form a 4 to 7 membered heterocycle; and
wherein Z is a hydrogel.

32. A prodrug precursor comprising:
a compound of formula Act-L;
wherein:
Act is a leaving group; and
L is a non-biologically active linker moiety $L^1$ which comprises an amine-containing nucleophile, and which is represented by formula (I):

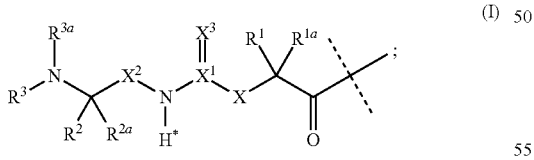

wherein:
the dashed line indicates the attachment to the nitrogen of the biologically active moiety by forming an amide bond;
X is $C(R^4R^{4a})$, $N(R^4)$, O, $C(R^4R^{4a})$—$C(R^5R^{5a})$—, $C(R^5R^{5a})$—$C(R^4R^{4a})$, $C(R^4R^{4a})$—$N(R^6)$, $N(R^6)$—$C(R^4R^{4a})$, $(R^4R^{4a})$—O, or O—C$(R^4R^{4a})$;
$X^1$ is C, or S(O);
$X^2$ is $C(R^7R^{7a})$, or $C(R^7R^{7a})$—$C(R^8R^{8a})$;
$X^3$ is O, S, or N—CN;

$R^1$; $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, and $R^{8a}$ are independently selected from the group consisting of H, and $C_{1-4}$ alkyl;
optionally, one or more of the pairs $R^{1a}/R^{4a}$, $R^{1a}/R^{5a}$, $R^{4a}/R^{5a}$, and $R^{7a}/R^{8a}$ form a chemical bond;
optionally, one or more of the pairs $R^1/R^{1a}$, $R^2/R^{2a}$, $R^4/R^{4a}$, $R^5/R^{5a}$, $R^7/R^{7a}$, and $R^8/R^{8a}$ are joined together with the atom to which they are attached to form a $C_{3-7}$ cycloalkyl, or 4 to 7 membered heterocyclyl;
optionally, one or more of the pairs $R^1/R^4$, $R^1/R^5$, $R^1/R^6$, $R^4/R^5$, $R^4/R^6$, $R^7/R^8$, and $R^2/R^3$ are joined together with the atoms to which they are attached to form a ring A;
optionally, $R^3/R^{3a}$ are joined together with the nitrogen atom to which they are attached to form a 4 to 7 membered heterocycle;
A is selected from the group consisting of:
phenyl, naphthyl, indenyl, indanyl, tetralinyl, $C_{3-10}$ cycloalkyl, 4 to 7 membered heterocyclyl, and 9 to 11 membered heterobicyclyl; and
—$N(R^3R^{3a})$ is the amine-containing nucleophile;
wherein $L^1$ is substituted with one to four groups $L^2$-Z and optionally further substituted, provided that the hydrogen marked with the asterisk in formula (I) is not replaced by a substituent, and wherein one or more further optional substituents are independently selected from the group consisting of:
halogen, CN, $COOR^9$, $OR^9$, $C(O)R^9$, $C(O)N(R^9R^{9a})$, $S(O)_2N(R^9R^{9a})$, $S(O)N(R^9R^{9a})$, $S(O)_2R^9S(O)R^9$, $N(R^9)S(O)_2N(R^{9a}R^{9b})$, $SR^9$, $N(R^9R^{9a})$, $NO_2$, $OC(O)R^9$, $N(R^9)C(O)R^{9a}$, $N(R^9)S(O)_2$, $R^{9a}$, $N(R^9)S(O)R^{9a}$, $N(R^9)C(O)OR^{9a}$, $N(R^9)C(O)N(R^{9a}R^{9b})$, $OC(O)N(R^9R^{9a})$, T, $C_{1-50}$ alkyl, $C_{2-50}$ alkenyl, and $C_{2-50}$ alkynyl;
wherein T $C_{1-50}$ alkyl, $C_{2-50}$ alkenyl, and $C_{2-50}$ alkynyl are optionally substituted with one or more $R^{10}$, which are the same or different;
wherein $C_{1-50}$ alkyl, $C_{2-50}$ alkenyl, and $C_{2-50}$ alkynyl are optionally interrupted by one or more groups selected from the group consisting of:
T, —C(O)O—, —O—, —C(O)—, —C(O)N$(R^{11})$—, —S(O)$_2$N$(R^{11})$—, —S(O)N$(R^{11})$—, —S(O)$_2$—, —S(O)—, —N$(R^{11})$S(O)$_2$N$(R^{11a})$—, —S—, —N$(R^{11})$—, —OC(O)$R^{11}$,— N$(R^{11})$C(O)—, —N$(R^{11})$S(O)$_2$—, —N$(R^{11})$S(O)—, —N$(R^{11})$C(O)O—, —N$(R^{11})$C(O)N$(R^{11a})$—, and —OC(O)N$(R^{11}R^{11a})$;
wherein $R^9$, $R^{9a}$, $R^{9b}$ are independently selected from the group consisting of:
H, T, $C_{1-50}$ alkyl, $C_{2-50}$ alkenyl, and $C_{2-50}$ alkynyl;
wherein T, $C_{1-50}$ alkyl, $C_{2-50}$ alkenyl, and $C_{2-50}$ alkynyl are optionally substituted with one or more $R^{10}$, which are the same or different; and
wherein $C_{1-50}$ alkyl, $C_{2-50}$ alkenyl, and $C_{2-50}$ alkynyl are optionally interrupted by one or more groups selected from the group consisting of:
T, —C(O)O—, —O—, —C(O)—, —C(O)N$(R^{11})$—, —S(O)$_2$N$(R^{11})$—, —S(O)N$(R^{11})$—, —S(O)$_2$—, —S(O)—, —N$(R^{11})$S(O)$_2$N$(R^{11a})$—, —S—, —N$(R^{11})$—OC(O)$R^{11}$, —N$(R^{11})$C(O)—, —N$(R^{11})$S(O)$_2$—, —N$(R^{11})$S(O)—, —N$(R^{11})$C(O)—, —N$(R^{11})$C(O)N$(R^{11a})$—, and —OC(O)N$(R^{11}R^{11a})$;

wherein T is selected from the group consisting of:
phenyl, naphthyl, indeny, indanyl, tetralinyl, $C_{3-10}$ cycloalkyl, 4 to 7 membered heterocyclyl, and 9 to 11 membered heterobicyclyl;
wherein T is optionally substituted with one or more $R^{10}$, which are the same or different;
wherein $R^{10}$ is:
halogen, CN, oxo (=O), $COOR^{12}$, $OR^{12}$, $C(O)R^{12}$, $C(O)N(R^{12}R^{12a})$, $S(O)_2N(R^{12}R^{12a})S(O)N(R^{12}R^{12a})S(O)$ $R^{12}$, $S(O)R^{12}$, $N(R^{12})S(O)_2N(R^{12a}R^{12b})$, $SR^{12}$, $N(R^{12}R^{12a})$, $NO_2$, $OC(O)R^{12}$, $N(R^{12})C(O)R^{12a}$, $N(R^{12})S(O)_2R^{12a}$, $N(R^{12})S(O)R^{12a}$, $N(R^{12})C(O)OR^{12a}$, $N(R^{12})C(O)N(R^{12a}R^{12b})$, $OC(O)N(R^{12}R^{12a})$, or $C_{1-6}$ alkyl;
wherein $C_{1-6}$ alkyl is optionally substituted with one or more halogen, which are the same or different; and
wherein $R^{11}$, $R^{11a}$, $R^{12}$, $R^{12a}$, and $R^{12b}$ are independently selected from the group consisting of; H and $C_{1-6}$ alkyl;
wherein $C_{1-6}$ alkyl is optionally substituted with one or more halogen, which are the same or different;
wherein $L^2$ is a single chemical bond or a spacer; and
wherein Z is a carrier group.

33. The prodrug precursor of claim 32;
wherein Act is chloride, bromide, fluoride, nitrophenoxy, imidazolyl, N-hydroxysuccinimidyl, N-hydroxybenzotriazolyl, N-hydroxyazobenzotriazolyl, pentafluorophenoxy, 2-thiooxo-thiazolidinyl, or N-hydroxysillfosuccinimidyl.

34. A pharmaceutical composition comprising:
a prodrug of claim 1 or a pharmaceutical salt thereof; and
a pharmaceutically acceptable excipient.

35. A method comprising:
administering the prodrug of claim 1.

36. A method comprising:
administering the pharmaceutical composition of claim 34.

37. The prodrug of claim 1;
wherein D-H is a GLP-1 receptor agonist; and
wherein L is represented by formula (Ib):

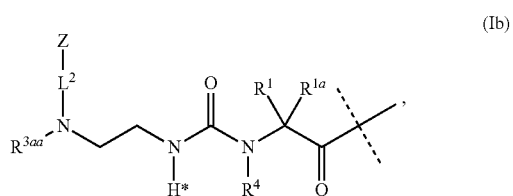

(Ib)

wherein:
$R^{3aa}$ is H or $C_{1-4}$ alkyl; and
Z is a hydrogel.

* * * * *